US007935791B2

(12) United States Patent
Fung et al.

(10) Patent No.: US 7,935,791 B2

(45) Date of Patent: May 3, 2011

(54) ANTAGONIST ANTI-NOTCH3 ANTIBODIES AND THEIR USE IN THE PREVENTION AND TREATMENT OF NOTCH3-RELATED DISEASES

(75) Inventors: Sek Chung Fung, Houston, TX (US); Kang Li, San Diego, CA (US); Yucheng Li, San Diego, CA (US); Sanjaya Singh, Sandy Hook, CT (US); Bin-Bing Stephen Zhou, Hohokus, NJ (US)

(73) Assignee: Genentech, Inc., South San Francisco, CA (US)

( * ) Notice: Subject to any disclaimer, the term of this patent is extended or adjusted under 35 U.S.C. 154(b) by 162 days.

(21) Appl. No.: 11/958,099

(22) Filed: Dec. 17, 2007

(65) Prior Publication Data

US 2008/0226621 A1 Sep. 18, 2008

Related U.S. Application Data

(60) Provisional application No. 60/879,218, filed on Jan. 6, 2007, provisional application No. 60/875,597, filed on Dec. 18, 2006.

(51) Int. Cl.
*C07K 16/30* (2006.01)

(52) U.S. Cl. ............... 530/387.1; 530/387.3; 530/387.7; 530/387.9; 530/388.22; 530/388.8; 530/391.3

(58) Field of Classification Search .................. 530/350, 530/387.1, 387.3, 387.9, 388.1, 388.22, 387.7, 530/388.8, 391.3

See application file for complete search history.

(56) References Cited

U.S. PATENT DOCUMENTS

| | | | |
|---|---|---|---|
| 5,648,464 | A | 7/1997 | Artavanis-Tsakonas et al. |
| 5,780,300 | A | 7/1998 | Artavanis-Tsakonas et al. |
| 5,786,158 | A | 7/1998 | Artavanis-Tsakonas et al. |
| 5,789,195 | A | 8/1998 | Artavanis-Tsakonas et al. |
| 6,083,904 | A | 7/2000 | Artavanis-Tsakonas et al. |
| 6,090,922 | A | 7/2000 | Artavanis-Tsakonas et al. |
| 6,149,902 | A | 11/2000 | Artavanis-Tsakonas et al. |
| 6,436,650 | B1 | 8/2002 | Artavanis-Tsakonas et al. |
| 6,692,919 | B1 | 2/2004 | Artavanis-Tsakonas et al. |
| 2002/0151487 | A1 | 10/2002 | Nickoloff et al. |
| 2003/0186290 | A1 | 10/2003 | Tournier-Lasserve et al. |
| 2004/0058443 | A1 | 3/2004 | Artavanis-Tsakonas et al. |
| 2004/0242482 | A1 | 12/2004 | Gehring et al. |
| 2005/0112121 | A1 | 5/2005 | Artavanis-Tsakonas et al. |
| 2005/0158859 | A1 | 7/2005 | Artavanis-Tsakonas et al. |
| 2005/0208027 | A1 | 9/2005 | Conboy et al. |
| 2006/0002924 | A1 | 1/2006 | Bodmer et al. |
| 2007/0003983 | A1 | 1/2007 | Artavanis-Tsakonas et al. |
| 2008/0107648 | A1 | 5/2008 | Noguera et al. |
| 2008/0118520 | A1 | 5/2008 | Li et al. |
| 2008/0131908 | A1 | 6/2008 | Li et al. |

FOREIGN PATENT DOCUMENTS

| | | | |
|---|---|---|---|
| FR | 2 777 285 | A1 | 10/1999 |
| WO | 95/15982 | | 6/1995 |
| WO | 00/20576 | | 4/2000 |
| WO | 2006/068822 | A1 | 6/2000 |
| WO | 02/24221 | A2 | 3/2002 |
| WO | 2006/015375 | A2 | 2/2006 |
| WO | 2006/017173 | A1 | 2/2006 |
| WO | 2006/053063 | A2 | 5/2006 |
| WO | 2008/057144 | A2 | 5/2008 |
| WO | 2008/150525 | A1 | 12/2008 |

OTHER PUBLICATIONS

Jiang et al. (J. Biol. Chem. Feb. 11, 2005; 280 (6): 4656-4662).*
Stancoviski et al. (Proceedings of the National Academy of Science USA. 1991; 88: 8691-8695).*
Li et al. (J. Biol. Chem. Mar. 21, 2008; 283 (12): 8046-8054).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Rudikoff et al. (Proc. Natl. Acad. Sci. USA. 1982; 79 (6): 1979-1983).*
Winkler et al. (J. Immunol. Oct. 15, 2000; 165 (8): 4505-4514).*
Chien et al. (Proc. Natl. Acad. Sci. USA. Jul. 1989; 86 (14): 5532-5536).*
Caldas et al. (Mol. Immunol. May 2003; 39 (15): 941-952).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Riemer et al. (Mol. Immunol. 2005; 42: 1121-1124).*
Pettersen et al. (J. Immunol. Jun. 15, 1999; 162 (12): 7031-7040).*
Vajdos et al. (J. Mol. Biol. Jul. 5, 2002; 320 (2): 415-428).*
Heller et al., "Amino Acids at the Site of V.-J. Recombination Not Encoded by Germline Sequences" *Journal of Experimental Medicine* 166:637-646 (1987).
Joutel et al., "skin biopay immunostaining with a Notch3 monoclonal antibody for CADASIL Diagnosis" *Lancet* 358:2049-2051 (2001).
Jurynczyk et al., "Notch3 Inhibition in Myelin-Reactive T Cells Down-Regulates Protein Kinase Cθ and Attenuates Experimental Autoimmune Encephalomyelitis" *Journal of Immunology* 180 (4): 2634-2640 (2008).
Li et al., "Modulation of Notch Signaling by Antibodies Specific for the Extracellular Negative Regulatory Region of NOTCH3" *Journal of Biolgoical Chemistry* 283 (12):8046-8054 (Mar. 21, 2008).
Rao et al., "K Chain Variable Regions from Three Galactan Binding Myeloma Proteins" *Biochemistry* 17 (25) :5555-5559 (1978).
Rudikoff et al., "K chain joining segments and structural diversity of antibody combining sites" *Proc. Natl. Acad. Sci. USA* 77(7) :4270-4274 (1980).
Allenspach et al., "Notch signaling in cancer" *Cancer Biol Ther*. 1(5) :466-76 (2002).

(Continued)

*Primary Examiner* — Stephen L Rawlings

(74) *Attorney, Agent, or Firm* — Danielle M. Pasqualone

(57) ABSTRACT

The present invention relates to antagonist antibodies that specifically bind to Notch 3 and inhibit its activation. The present invention includes antibodies binding to a conformational epitope comprising the first Lin12 domain and the second dimerization domain. The present invention also includes uses of these antibodies to treat or prevent Notch 3 related diseases or disorders.

11 Claims, 27 Drawing Sheets

OTHER PUBLICATIONS

Anastasi et al., "Expression of activated Notch3 in transgenic mice enhances generation of T regulatory cells and protects against experimental autoimmune diabetes" *J Immunol.* 171(9) :4504-11 (Nov. 2003).
Androutsellis-Theotokis et al., "Notch signalling regulates stem cell numbers in vitro and in vivo" *Nature* 442:823-6 (Aug. 2006).
Artavanis-Tsakonas et al., "Notch Signaling" *Science* 268:225-232 (Apr. 14, 1995).
Artavanis-Tsakonas et al., "Notch Signaling: Cell Fate Control and Signal Integration in Development" *Science* 284:770-776 (1999).
Aster et al., "The folding and structural integrity of the first LIN-12 module of human Notch1 are calcium-dependent" *Biochemistry* 38(15) :4736-42 (Apr. 1999).
Bellavia et al., "Combined expression of pTalpha and Notch3 in T cell leukemia identifies the requirement of preTCR for leukemogenesis" *Proc Natl Acad Sci U S A.* 99(5):3788-93 (Mar. 2002).
Bocchetta et al., "Notch-1 induction, a novel activity of SV40 required for growth of SV40-transformed human mesothelial cells" *Oncogene* 22(1):81-9 (Jan. 2003).
Bolos et al., "Notch signaling in development and cancer" *Endocr Rev.* 28(3):339-63 (May 2007).
Bray, "Notch signalling: a simple pathway becomes complex" *Nat Rev Mol Cell Biol.* 7(9):678-89 (Sep. 2006).
Buchler et al., "The Notch signaling pathway is related to neurovascular progression of pancreatic cancer" *Ann Surg.* 242(6):791-800 (Dec. 2005).
Chiba, "Notch signaling in stem cell systems" *Stem Cells* 24(11):2437-47 (Nov. 2006).
Coffman et al., "Expression of an extracellular deletion of Xotch diverts cell fate in *Xenopus embryos*" *Cell* 73(4):659-71 (May 1993).
Davies et al., "Affinity improvement of single antibody VH domains: residues in all three hypervariable regions affect antigen binding" *Immunotechnology* 2:169-179 (1996).
Domenga et al., "Notch3 is required for arterial identity and maturation of vascular smooth muscle cells" *Genes Dev.* 18(22):2730-5 (Nov. 2004).
Ellisen et al., "TAN-1, the human homolog of the *Drosophila* notch gene, is broken by chromosomal translocations in T lymphoblastic neoplasms" *Cell* 66(4):649-61 (Aug. 1991).
Fan et al., "Notch pathway inhibition depletes stem-like cells and blocks engraftment in embryonal brain tumors" *Cancer Research* 66(15):7445-52 (Aug. 2006).
Flynn et al., "The role of Notch receptor expression in bile duct development and disease" *J Pathol.* 204(1):55-64 (Sep. 2004).
Fre et al., "Notch signals control the fate of immature progenitor cells in the intestine" *Nature* 435:964-8 (Jun. 2005).
Gordon et al., "Structural basis for autoinhibition of Notch" *Nat Struct Mol Biol.* 14(4):295-300 (Apr. 2007).
Haruki et al., "Dominant-negative Notch3 receptor inhibits mitogen-activated protein kinase pathway and the growth of human lung cancers" *Cancer Research* 65(9):3555-61 (May 2005).
Hedvat et al., "Insights into extramedullary tumour cell growth revealed by expression profiling of human plasmacytomas and multiple myeloma" *Br J Haematol.* 122(5):728-44 (Sep. 2003).
Holt et al., "Domain antibodies: proteins for therapy" *Trends Biotechnol.* 21(11):484-490 (Nov. 2003).
Houde et al., "Overexpression of the NOTCH ligand JAG2 in malignant plasma cells from multiple myeloma patients and cell lines" *Blood* 104(12):3697-704 (Dec. 2004).
Hu et al., "Overexpression of activated murine Notch1 and Notch3 in transgenic mice blocks mammary gland development and induces mammary tumors" *Am J Pathol.* 168(3):973-90 (Mar. 2006).
Jang et al., "Notch signaling as a target in multimodality cancer therapy" *Curr Opin Mol Ther.* 2(1):55-65 (Feb. 2000).
Joutel et al., "Notch signalling pathway and human diseases" *Semin Cell Dev Biol.* 9(6):619-25 (Dec. 1998).
Joutel et al., "Notch3 mutations in CADASIL, a hereditary adult-onset condition causing stroke and dementia" *Nature* 383:707-10 (Oct. 1996).
Jundt et al., "Jagged1—induced Notch signaling drives proliferation of multiple myeloma cells" *Blood* 103(9):3511-5 (May 2004).
Kadesch, "Notch signaling: a dance of proteins changing partners" *Exp Cell Res.* 260(1):1-8 (Oct. 2000).
Kidd et al., "Sequence of the notch locus of *Drosophila melanogaster*: relationship of the encoded protein to mammalian clotting and growth factors" *Mol Cell Biol.* 6(9):3094-108 (Sep. 1986).
Kopczynski et al., "Delta, a *Drosophila* neurogenic gene, is transcriptionally complex and encodes a protein related to blood coagulation factors and epidermal growth factor of vertebrates" *Genes Dev.* 2:1723-35 (1988).
Leong et al., "Recent insights into the role of Notch signaling in tumorigenesis" *Blood* 107(6):2223-33 (Mar. 2006).
Lu et al., "Selection of potential markers for epithelial ovarian cancer with gene expression arrays and recursive descent partition analysis" *Clin Cancer Res.* 10(10):3291-300. (May 2004).
Mailhos et al., "Delta4, an Endothelial Specific Notch Ligand Expressed at Sites of Physiological and Tumor Angiogenesis" *Differentiation* 69:135-144 (2001).
Malecki et al., "Leukemia-associated mutations within the NOTCH1 heterodimerization domain fall into at least two distinct mechanistic classes" *Mol Cell Biol.* 26(12):4642-51 (Jun. 2006).
Nam et al., "Notch signaling as a therapeutic target" *Curr Opin Chem Biol.* 6(4):501-9 (Aug. 2002).
Park et al., "Notch3 gene amplification in ovarian cancer" *Cancer Research* 66(12):6312-8 (Jun. 2006).
Reya et al., "Stem cells, cancer, and cancer stem cells" *Nature* 414:105-11 (2001).
Sanchez-Irizarry et al., "Notch subunit heterodimerization and prevention of ligand-independent proteolytic activation depend, respectively, on a novel domain and the LNR repeats" *Mol Cell Biol.* 24(21):9265-73 (2004).
Screpanti et al., "Notch, a unifying target in T-cell acute lymphoblastic leukemia?" *Trends Mol Med.* 9(1):30-5 (Jan. 2003).
Shimizu et al., "Physical interaction of Delta1, Jagged1, and Jagged2 with Notch1 and Notch 3 receptors" *Biochem Biophys Res Commun.* 276(1):385-9 (Sep. 2000).
Sullivan and Bicknell, "New molecular pathways in angiogenesis" *British Journal of Cancer* 89(2):228-231 (Jul. 21, 2003).
Sweeney et al., "Notch 1 and 3 receptor signaling modulates vascular smooth muscle cell growth, apoptosis, and migration via a CBF-1/RBP-Jk dependent pathway" *FASEB J.* 18(12):1421-3 (Sep. 2004).
Swiatek et al., "Notch1 is essential for postimplantation development in mice" *Genes Dev.* 8(6):707-19 (Mar. 1994).
Taichman et al., "Notch1 and Jagged1 expression by the developing pulmonary vasculature" *Dev Dyn.* 225(2):166-75 (Oct. 2002).
Thelu et al., "Notch signalling is linked to epidermal cell differentiation level in basal cell carcinoma, psoriasis and wound healing" *BMC Dermatol.* 2:7 (Apr. 2002).
Vacca et al., "Notch3 and pre-TCR interaction unveils distinct NF-kappaB pathways in T-cell development and leukemia" *EMBO Journal* 25(5):1000-8 (Mar. 2006).
van Es et al., "Notch/gamma-secretase inhibition turns proliferative cells in intestinal crypts and adenomas into goblet cells" *Nature* 435:959-63 (Jun. 2005).
van Limpt et al., "Phox2B mutations and the Delta-Notch pathway in neuroblastoma" *Cancer Lett.* 228:59-63 (Oct. 2005).
Vardar et al., "Nuclear magnetic resonance structure of a prototype Lin12-Notch repeat module from human Notch1" *Biochemistry* 42(23):7061-7 (Jun. 2003).
Von Boehmer, "Notch in lymphopoiesis and T cell polarization" *Nat Immunol.* 6(7):641-2 (Jul. 2005).
Weijzen et al., "Activation of Notch-1 signaling maintains the neoplastic phenotype in human Ras-transformed cells" *Nat Med.* 8(9):979-986 (Sep. 2002).

Weng et al., "Activating mutations of NOTCH1 in human T cell acute lymphoblastic leukemia" *Science* 306(5694):269-271 (Oct. 8, 2004).
Wharton et al., "Nucleotide sequence from the neurogenic locus notch implies a gene product that shares homology with proteins containing EGF-like repeats" *Cell* 43:567-81 (Dec. 1985).
Xu et al., "Regions of *Drosophila* Notch that contribute to ligand binding and the modulator influence of Fringe" *J Biol Chem*. 280(34):30158-65 (Aug. 2005).
Yabe et al., "Immunohistological localization of Notch receptors and their ligands Delta and jagged in synovial tissues of rheumatoid arthritis" *J Orthop Sci*. 10(6):589-94 (Nov. 2005).
Yochem et al., "The Caenorhabditis elegans lin-12 gene encodes a transmembrane protein with overall similarity to *Drosophila* Notch" *Nature* 335:547-50 (Oct. 1988).
Zeng et al., "Crosstalk between tumor and endothelial cells promotes tumor angiogenesis by MAPK activation of Notch signaling" *Cancer Cell* 8(1):13-23 (Jul. 2005).
Zweidler-McKay et al., "Notch signaling is a potent inducer of growth arrest and apoptosis in a wide range of B-cell malignancies" *Blood* 106(12):3898-906 (Dec. 2005).
GenBank Accession No. AF471251.1; Scamurra; Oct. 11, 2003.
Talora et al., "Specific down-modulation of Notch1 signaling in cervical cancer cells is required for sustained HPV-E6/E7 expression and late steps of malignant transformation" *Genes & Development* 16(17):2252-2263 (2002).

* cited by examiner

FIGURE 1:

Amino Acid Sequence of Human Notch 3 (NP_ 000426)

1 MGPGARGRRR RRRPMSPPPP PPPVRALPLL LLLAGPGAAA PPCLDGSPCA NGGRCTQLPS
61 REAACLCPPG WVGERCQLED PCHSGPCAGR GVCQSSVVAG TARFSCRCPR GFRGPDCSLP
121 DPCLSSPCAH GARCSVGPDG RFLCSCPPGY QGRSCRSDVD ECRVGEPCRH GGTCLNTPGS
181 FRCQCPAGYT GPLCENPAVP CAPSPCRNGG TCRQSGDLTY DCACLPGFEG QNCEVNVDDC
241 PGHRCLNGGT CVDGVNTYNC QCPPEWTGQF CTEDVDECQL QPNACHNGGT CFNTLGGHSC
301 VCVNGWTGES CSQNIDDCAT AVCFHGATCH DRVASFYCAC PMGKTGLLCH LDDACVSNPC
361 HEDAICDTNP VNGRAICTCP PGFTGGACDQ DVDECSIGAN PCEHLGRCVN TQGSFLCQCG
421 RGYTGPRCET DVNECLSGPC RNQATCLDRI GQFTCICMAG FTGTYCEVDI DECQSSPCVN
481 GGVCKDRVNG FSCTCPSGFS GSTCQLDVDE CASTPCRNGA KCVDQPDGYE CRCAEGFEGT
541 LCDRNVDDCS PDPCHHGRCV DGIASFSCAC APGYTGTRCE SQVDECRSQP CRHGGKCLDL
601 VDKYLCRCPS GTTGVNCEVN IDDCASNPCT FGVCRDGINR YDCVCQPGFT GPLCNVEINE
661 CASSPCGEGG SCVDGENGFR CLCPPGSLPP LCLPPSHPCA HEPCSHGICY DAPGGFRCVC
721 EPGWSGPRCS QSLARDACES QPCRAGGTCS SDGMGFHCTC PPGVQGRQCE LLSPCTPNPC
781 EHGGRCESAP GQLPVCSCPQ GWQGPRCQQD VDECAGPAPC GPHGICTNLA GSFSCTCHGG
841 YTGPSCDQDI NDCDPNPCLN GGSCQDGVGS FSCSCLPGFA GPRCARDVDE CLSNPCGPGT
901 CTDHVASFTC TCPPGYGGFH CEQDLPDCSP SSCFNGGTCV DGVNSFSCLC RPGYTGAHCQ
961 HEADPCLSRP CLHGGVCSAA HPGFRCTCLE SFTGPQCQTL VDWCSRQPCQ NGGRCVQTGA
1021 YCLCPPGWSG RLCDIRSLPC REAAAQIGVR LEQLCQAGGQ CVDEDSSHYC VCPEGRTGSH
1081 CEQEVDPCLA QPCQHGGTCR GYMGGYMCEC LPGYNGDNCE DDVDECASQP CQHGGSCIDL
1141 VARYLCSCPP GTLGVLCEIN EDDCGPGPPL DSGPRCLHNG TCVDLVGGFR CTCPPGYTGL
1201 RCEADINECR SGACHAAHTR DCLQDPGGGF RCLCHAGFSG PRCQTVLSPC ESQPCQHGGQ
1261 CRPSPGPGGG LTFTCHCAQP FWGPRCERVA RSCRELQCPV GVPCQQTPRG PRCACPPGLS
1321 GPSCRSFPGS PPGASNASCA AAPCLHGGSC RPAPLAPFFR CACAQGWTGP RCEAPAAAPE
1381 VSE*EPRCPRA ACQAKRGDQR CDRECNSPGC GWDGGDCSLS VGDPWRQCEA LQCWRLFNNS*
*1441 RCDPACSSPA CLYDNFDCHA GGRERTCNPV YEKYCADHFA DGRCDQGCNT EECGWDGLDC*
*1501 ASE*VPALLAR GVLVLTVLLP PEELLRSSAD FLQRLSAILR TSLRFRLDAH GQAMVFPYHR
1561 PSPGSEPRAR RELAPEVIGS VVMLEIDNRL CLQSPENDHC FPDAQSAADY LGALSAVERL
1621 DFPYPLRDVR GEPLEPPEPS VPLLPLLVAG AVLLLVILVL GVMVARRKRE HSTLWFPEGF
1681 SLHKDVASGH KGRREPVGQD ALGMKNMAKG ESLMGEVATD WMDTECPEAK RLKVEEPGMG
1741 AEEAVDCRQW TQHHLVAADI RVAPAMALTP PQGDADADGM DVNVRGPDGF TPLMLASFCG
1801 GALEPMPTEE DEADDTSASI ISDLICQGAQ LGARTDRTGE TALHLAARYA RADAAKRLLD
1861 AGADTNAQDH SGRTPLHTAV TADAQGVFQI LIRNRSTDLD ARMADGSTAL ILAARLAVEG
1921 MVEELIASHA DVNAVDELGK SALHWAAAVN NVEATLALLK NGANKDMQDS KEETPLFLAA
1981 REGSYEAAKL LLDHFANREI TDHLDRLPRD VAQERLHQDI VRLLDQPSGP RSPPGPHGLG
2041 PLLCPPGAFL PGLKAAQSGS KKSRRPPGKA GLGPQGPRGR GKKLTLACPG PLADSSVTLS
2101 PVDSLDSPRP FGGPPASPGG FPLEGPYAAA TATAVSLAQL GGPGRAGLGR QPPGGCVLSL
2161 GLLNPVAVPL DWARLPPPAP PGPSFLLPLA PGPQLLNPGT PVSPQERPPP YLAVPGHGEE
2221 YPVAGAHSSP PKARFLRVPS EHPYLTPSPE SPEHWASPSP PSLSDWSEST PSPATATGAM
2281 ATTTGALPAQ PLPLSVPSSL AQAQTQLGPQ PEVTPKRQVL A (SEQ ID NO 1)

FIGURE 2

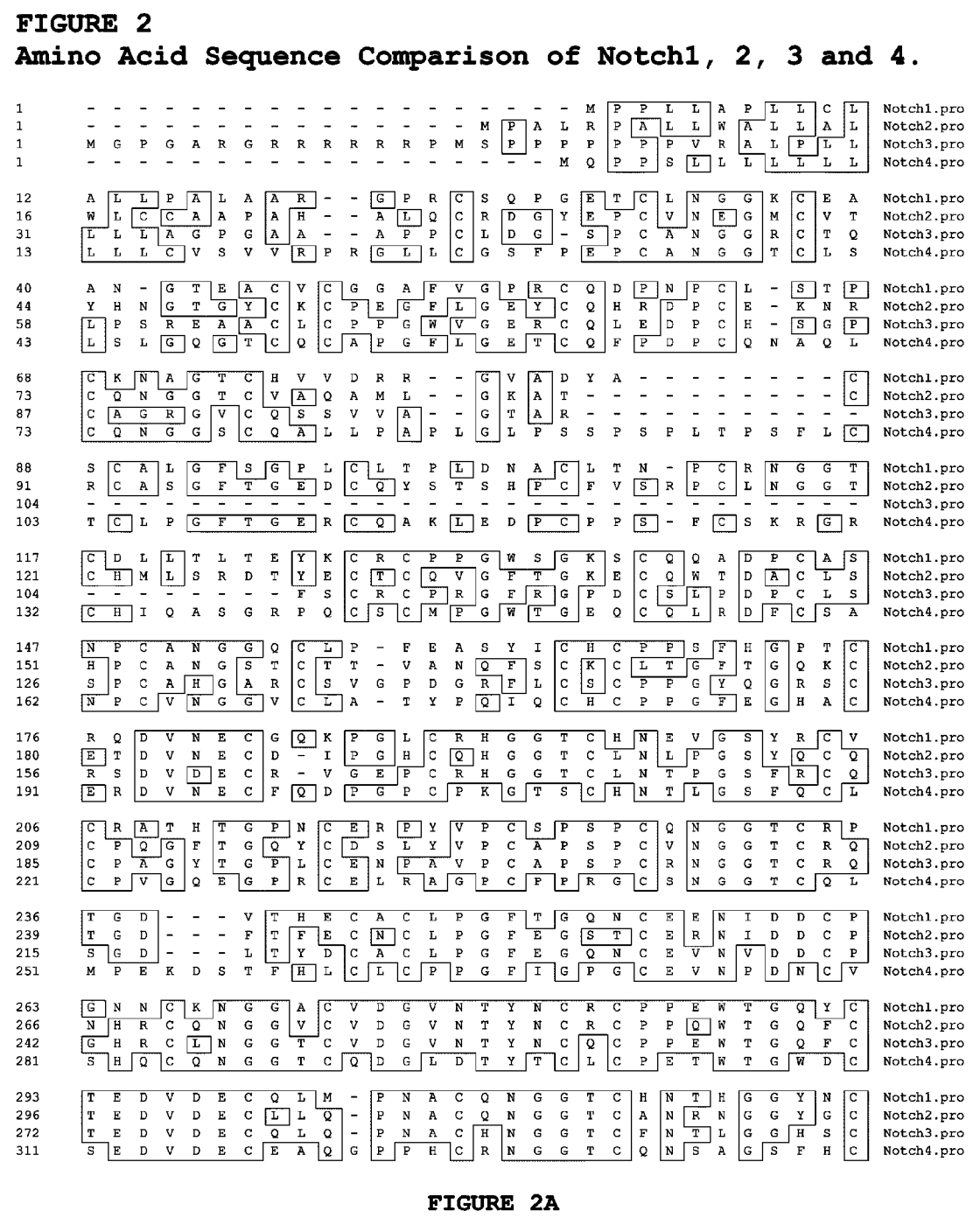

Amino Acid Sequence Comparison of Notch1, 2, 3 and 4.

```
1    - - - - - - - - - - - - - - - - - - - M P P L L A P L L C L   Notch1.pro
1    - - - - - - - - - - - - - - - M P A L R P A L L W A L L A L   Notch2.pro
1    M G P G A R G R R R R R R P M S P P P P P P P V R A L P L L   Notch3.pro
1    - - - - - - - - - - - - - - - - - - M Q P P S L L L L L L L   Notch4.pro

12   A L L P A L A A R - - G P R C S Q P G E T C L N G G K C E A   Notch1.pro
16   W L C C A A P A H - - A L Q C R D G Y E P C V N E G M C V T   Notch2.pro
31   L L L A G P G A A - - A P P C L D G - S P C A N G G R C T Q   Notch3.pro
13   L L L C V S V V R P R G L L C G S F P E P C A N G G T C L S   Notch4.pro

40   A N - G T E A C V C G G A F V G P R C Q D P N P C L - S T P   Notch1.pro
44   Y H N G T G Y C K C P E G F L G E Y C Q H R D P C E - K N R   Notch2.pro
58   L P S R E A A C L C P P G W V G E R C Q L E D P C H - S G P   Notch3.pro
43   L S L G Q G T C Q C A P G F L G E T C Q F P D P C Q N A Q L   Notch4.pro

68   C K N A G T C H V V D R R - - G V A D Y A - - - - - - - - C   Notch1.pro
73   C Q N G G T C V A Q A M L - - G K A T - - - - - - - - - - C   Notch2.pro
87   C A G R G V C Q S S V V A - - G T A R - - - - - - - - - - -   Notch3.pro
73   C Q N G G S C Q A L L P A P L G L P S S P S P L T P S F L C   Notch4.pro

88   S C A L G F S G P L C L T P L D N A C L T N - P C R N G G T   Notch1.pro
91   R C A S G F T G E D C Q Y S T S H P C F V S R P C L N G G T   Notch2.pro
104  - - - - - - - - - - - - - - - - - - - - - - - - - - - - - -   Notch3.pro
103  T C L P G F T G E R C Q A K L E D P C P P S - F C S K R G R   Notch4.pro

117  C D L L T L T E Y K C R C P P G W S G K S C Q Q A D P C A S   Notch1.pro
121  C H M L S R D T Y E C T C Q V G F T G K E C Q W T D A C L S   Notch2.pro
104  - - - - - - - - F S C R C P R G F R G P D C S L P D P C L S   Notch3.pro
132  C H I Q A S G R P Q C S C M P G W T G E Q C Q L R D F C S A   Notch4.pro

147  N P C A N G G Q C L P - F E A S Y I C H C P P S F H G P T C   Notch1.pro
151  H P C A N G S T C T T - V A N Q F S C K C L T G F T G Q K C   Notch2.pro
126  S P C A H G A R C S V G P D G R F L C S C P P G Y Q G R S C   Notch3.pro
162  N P C V N G G V C L A - T Y P Q I Q C H C P P G F E G H A C   Notch4.pro

176  R Q D V N E C G Q K P G L C R H G G T C H N E V G S Y R C V   Notch1.pro
180  E T D V N E C D - I P G H C Q H G G T C L N L P G S Y Q C Q   Notch2.pro
156  R S D V D E C R - V G E P C R H G G T C L N T P G S F R C Q   Notch3.pro
191  E R D V N E C F Q D P G P C P K G T S C H N T L G S F Q C L   Notch4.pro

206  C R A T H T G P N C E R P Y V P C S P S P C Q N G G T C R P   Notch1.pro
209  C P Q G F T G Q Y C D S L Y V P C A P S P C V N G G T C R Q   Notch2.pro
185  C P A G Y T G P L C E N P A V P C A P S P C R N G G T C R Q   Notch3.pro
221  C P V G Q E G P R C E L R A G P C P P R G C S N G G T C Q L   Notch4.pro

236  T G D - - - V T H E C A C L P G F T G Q N C E E N I D D C P   Notch1.pro
239  T G D - - - F T F E C N C L P G F E G S T C E R N I D D C P   Notch2.pro
215  S G D - - - L T Y D C A C L P G F E G Q N C E V N V D D C P   Notch3.pro
251  M P E K D S T F H L C L C P P G F I G P G C E V N P D N C V   Notch4.pro

263  G N N C K N G G A C V D G V N T Y N C R C P P E W T G Q Y C   Notch1.pro
266  N H R C Q N G G V C V D G V N T Y N C R C P P Q W T G Q F C   Notch2.pro
242  G H R C L N G G T C V D G V N T Y N C Q C P P E W T G Q F C   Notch3.pro
281  S H Q C Q N G G T C Q D G L D T Y T C L C P E T W T G W D C   Notch4.pro

293  T E D V D E C Q L M - P N A C Q N G G T C H N T H G G Y N C   Notch1.pro
296  T E D V D E C L L Q - P N A C Q N G G T C A N R N G G Y G C   Notch2.pro
272  T E D V D E C Q L Q - P N A C H N G G T C F N T L G G H S C   Notch3.pro
311  S E D V D E C E A Q G P P H C R N G G T C Q N S A G S F H C   Notch4.pro
```

FIGURE 2A

```
322 V C V N G W T G E D C S E N I D D C A S A A C F H G A T C H Notch1.pro
325 V C V N G W S G D D C S E N I D D C A F A S C T P G S T C I Notch2.pro
301 V C V N G W T G E S C S Q N I D D C A T A V C F H G A T C H Notch3.pro
341 V C V S G W G G T S C E E N L D D C I A A T C A P G S T C I Notch4.pro

352 D R V A S F Y C E C P H G R T G L L C H L N D A C I S N P C Notch1.pro
355 D R V A S F S C M C P E G K A G L L C H L D D A C I S N P C Notch2.pro
331 D R V A S F Y C A C P M G K T G L L C H L D D A C V S N P C Notch3.pro
371 D R V G S F S C L C P P G R T G L L C H L E D M C L S Q P C Notch4.pro

382 N E G S N C D T N P V N G K A I C T C P S G Y T G P A C S Q Notch1.pro
385 H K G A L C D T N P L N G Q Y I C T C P Q G Y K G A D C T E Notch2.pro
361 H E D A I C D T N P V N G R A I C T C P P G F T G G A C D Q Notch3.pro
401 H G D A Q C S T N P L T G S T L C L C Q P G Y S G P T C H Q Notch4.pro

412 D V D E C S L G - - - A N P C E H A G K C I N T L G S F E C Notch1.pro
415 D V D E C A M A N - - S N P C E H A G K C V N T D G A F H C Notch2.pro
391 D V D E C S I G - - - A N P C E H L G R C V N T Q G S F L C Notch3.pro
431 D L D E C L M A Q Q G P S P C E H G G S C L N T P G S F N C Notch4.pro

439 Q C L Q G Y T G P R C E I D V N E C V S N P C Q N D A T C L Notch1.pro
443 E C L K G Y A G P R C E M D I N E C H S D P C Q N D A T C L Notch2.pro
418 Q C G R G Y T G P R C E T D V N E C L S G P C R N Q A T C L Notch3.pro
461 L C P P G Y T G S R C E A D H N E C L S Q P C H P G S T C L Notch4.pro

469 D Q I G E F Q C I C M P G Y E G V H C E V N T D E C A S S P Notch1.pro
473 D K I G G F T C L C M P G F K G V H C E L E I N E C Q S N P Notch2.pro
448 D R I G Q F T C I C M A G F T G T Y C E V D I D E C Q S S P Notch3.pro
491 D L L A T F H C L C P P G L E G Q L C E V E T N E C A S A P Notch4.pro

499 C L H N G R C L D K I N E F Q C E C P T G F T G H L C Q Y D Notch1.pro
503 C V N N G Q C V D K V N R F Q C L C P P G F T G P V C Q I D Notch2.pro
478 C V N G G V C K D R V N G F S C T C P S G F S G S T C Q L D Notch3.pro
521 C L N H A D C H D L L N G F Q C I C L P G F S G T R C E E D Notch4.pro

529 V D E C A S T P C K N G A K C L D G P N T Y T C V C T E G Y Notch1.pro
533 I D D C S S T P C L N G A K C I D H P N G Y E C Q C A T G F Notch2.pro
508 V D E C A S T P C R N G A K C V D Q P D G Y E C R C A E G F Notch3.pro
551 I D E C R S S P C A N G G Q C Q D Q P - - - - - - - - - - - Notch4.pro

559 T G T H C E V D I D E C D P D P C H Y G S C K D G V A T F T Notch1.pro
563 T G V L C E E N I D N C D P D P C H H G Q C Q D G I D S Y T Notch2.pro
538 E G T L C D R N V D D C S P D P C H H G R C V D G I A S F S Notch3.pro
570 - - - - - - - - - - - - - - - - - - - - - - - - - - G A F H Notch4.pro

589 C L C R P G Y T G H H C E T N I N E C S S Q P C R H G G T C Notch1.pro
593 C I C N P G Y M G A I C S D Q I D E C Y S S P C L N D G R C Notch2.pro
568 C A C A P G Y T G T R C E S Q V D E C R S Q P C R H G G K C Notch3.pro
574 C K C L P G F E G P R C Q T E V D E C L S D P C P V G A S C Notch4.pro

619 Q D R D N A Y L C F C L K G T T G P N C E I N L D D C A S S Notch1.pro
623 I D L V N G Y Q C N C Q P G T S G V N C E I N F D D C A S N Notch2.pro
598 L D L V D K Y L C R C P S G T T G V N C E V N I D D C A S N Notch3.pro
604 L D L P G A F F C L C P S - - - - - - - - - - - - - - - - - Notch4.pro

649 P C D S G T C L D K I D G Y E C A C E P G Y T G S M C N I N Notch1.pro
653 P C I H G I C M D G I N R Y S C V C S P G F T G Q R C N I D Notch2.pro
628 P C T F G V C R D G I N R Y D C V C Q P G F T G P L C N V E Notch3.pro
617 - - - - - - - - - - - - - - - - - - - G F T G Q L C E V P Notch4.pro
```

FIGURE 2B

```
679   I D E C A G N P C H N G G T C E D G I N G F T C R C P E G Y   Notch1.pro
683   I D E C A S N P C R K G A T C I N G V N G F R C I C P E G P   Notch2.pro
658   I N E C A S S P C G E G G S C V D G E N G F R C L C P P G S   Notch3.pro
627   L - - C A P N L C Q P K Q I C K D Q K D K A N C L C P D G -   Notch4.pro

709   H D P T C L S E V N E C N S N P C V H G A C R D S L N G Y K   Notch1.pro
713   H H P S C Y S Q V N E C L S N P C I H G N C T G G L S G Y K   Notch2.pro
688   L P P L C L P P S H P C A H E P C S H G I C Y D A P G G F R   Notch3.pro
654   - S P G C A P P E D N C T - - - C H H G H C Q R S S - - - -   Notch4.pro

739   C D C D P G W S G T N C - - D I N N N E C E S N P C V N G G   Notch1.pro
743   C L C D A G W V G I N C - - E V D K N E C L S N P C Q N G G   Notch2.pro
718   C V C E P G W S G P R C S Q S L A R D A C E S Q P C R A G G   Notch3.pro
676   C V C D V G W T G P E C - - E A E L G G C I S A P C A H G G   Notch4.pro

767   T C K D M T S G Y V C T C R E G F S G P N C Q T N I N E C A   Notch1.pro
771   T C D N L V N G Y R C T C K K G F K G Y N C Q V N I D E C A   Notch2.pro
748   T C S S D G M G F H C T C P P G V Q G R Q C E L - - - - - -   Notch3.pro
704   T C Y P Q P S G Y N C T C P T - - - - - - - - - - - - - - -   Notch4.pro

797   S N P C L N Q G T C I D D V A G Y K C N C L L P Y T G A T C   Notch1.pro
801   S N P C L N Q G T C F D D I S G Y T C H C V L P Y T G K N C   Notch2.pro
772   - - - - - - - - - - - - - - - - - - - - - - - - - - - - - -   Notch3.pro
719   - - - - - - - - - - - - - - - - - - - - - - - - - - - - - -   Notch4.pro

827   E V V L A P C A P S P C R N G G E C R Q S E D Y E S F S C V   Notch1.pro
831   Q T V L A P C S P N P C E N A A V C K E S P N F E S Y T C L   Notch2.pro
772   - - - L S P C T P N P C E H G G R C E S A P G - Q L P V C S   Notch3.pro
719   - - - - - - - - - - - - - - - - - - - - - - - - - - - - - -   Notch4.pro

857   C P T G W Q A G Q T C E V D I N E C V L - S P C R H G A S C   Notch1.pro
861   C A P G W Q G - Q R C T I D I D E C I S - K P C M N H G L C   Notch2.pro
798   C P Q G W Q G - P R C Q Q D V D E C A G P A P C G P H G I C   Notch3.pro
719   - - - - - - - - - - - - - - - - - - - - - - - - - - - - - -   Notch4.pro

886   Q N T H G G Y R C H C Q A G Y S G R N C E T D I D D C R P N   Notch1.pro
889   H N T Q G S Y M C E C P P G F S G M D C E E D I D D C L A N   Notch2.pro
827   T N L A G S F S C T C H G G Y T G P S C D Q D I N D C D P N   Notch3.pro
719   - - - - - - - - - - - - - G Y T G P T C S E E M T A C H S G   Notch4.pro

916   P C H N G G S C T D G I N T A F C D C L P G F R G T F C E E   Notch1.pro
919   P C Q N G G S C M D G V N T F S C L C L P G F T G D K C Q T   Notch2.pro
857   P C L N G G S C Q D G V G S F S C S C L P G F A G P R C A R   Notch3.pro
736   P C L N G G S C N P S P G G Y Y C T C P P S H T G P Q C Q T   Notch4.pro

946   D I N E C A S D P C R N G A N C T D C V D S Y T C T C P A G   Notch1.pro
949   D M N E C L S E P C K N G G T C S D Y V N S Y T C K C Q A G   Notch2.pro
887   D V D E C L S N P C G P G - T C T D H V A S F T C T C P P G   Notch3.pro
766   S T D Y C V S A P C - - - - - - - - - - - - - - - - - - - -   Notch4.pro

976   F S G I H C E N N T P D C T E S S C F N G G T C V D G I N S   Notch1.pro
979   F D G V H C E N N I N E C T E S S C F N G G T C V D G I N S   Notch2.pro
916   Y G G F H C E Q D L P D C S P S S C F N G G T C V D G V N S   Notch3.pro
776   - - - - - - - - - - - - - - - - - - F N G G T C V N R P G T   Notch4.pro

1006  F T C L C P P G F T G S Y C Q H D V N - E C D S Q P C L H G   Notch1.pro
1009  F S C L C P V G F T G S F C L H E I N - E C S S H P C L N E   Notch2.pro
946   F S C L C R P G Y T G A H C Q H E A D - P C L S R P C L H G   Notch3.pro
788   F S C L C A M G F Q G P R C E G K L R P S C A D S P C R N R   Notch4.pro
```

FIGURE 2C

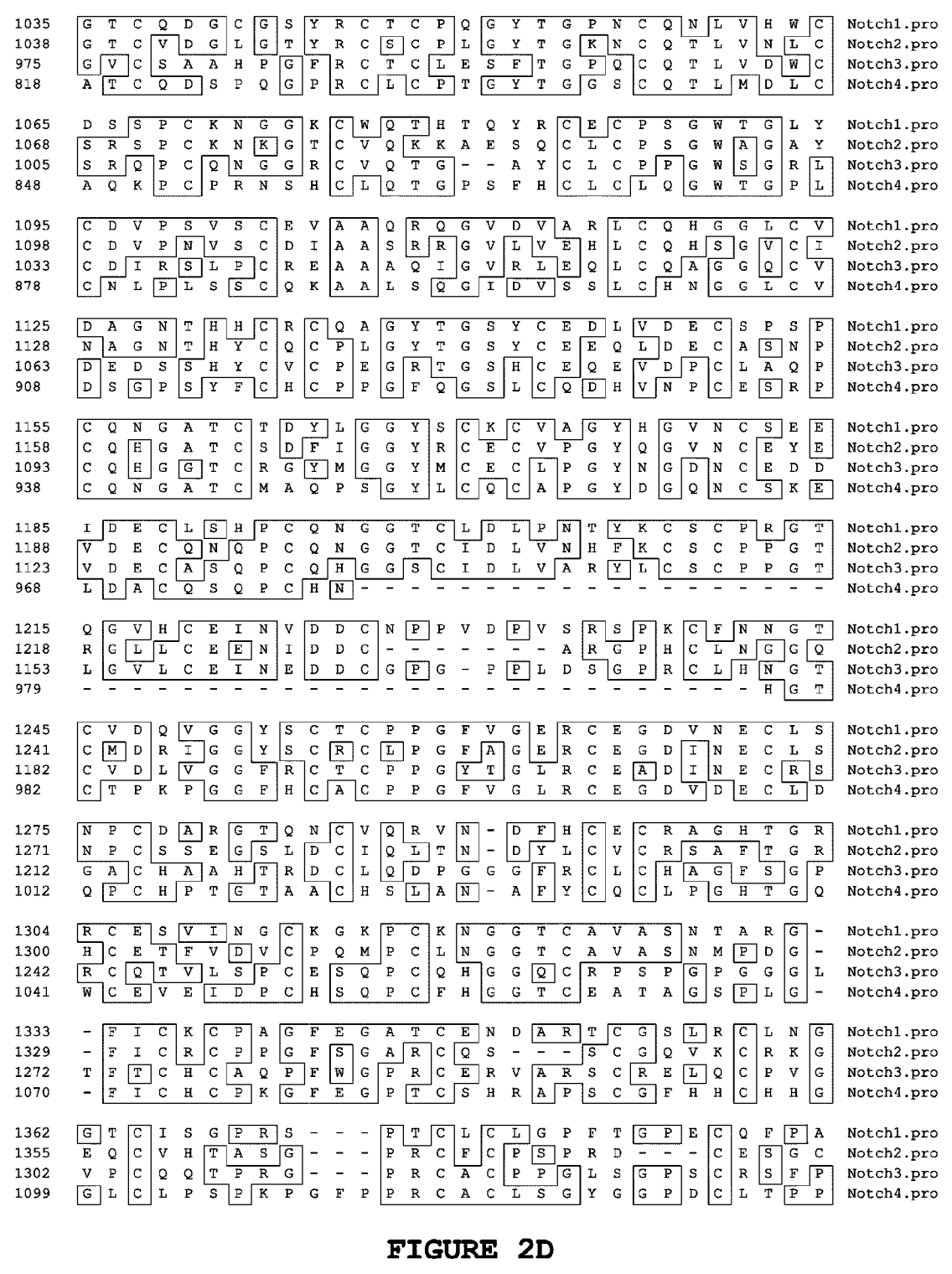

```
1035  G T C Q D G C G S Y R C T C P Q G Y T G P N C Q N L V H W C  Notch1.pro
1038  G T C V D G L G T Y R C S C P L G Y T G K N C Q T L V N L C  Notch2.pro
975   G V C S A A H P G F R C T C L E S F T G P Q C Q T L V D W C  Notch3.pro
818   A T C Q D S P Q G P R C L C P T G Y T G G S C Q T L M D L C  Notch4.pro

1065  D S S P C K N G G K C W Q T H T Q Y R C E C P S G W T G L Y  Notch1.pro
1068  S R S P C K N K G T C V Q K K A E S Q C L C P S G W A G A Y  Notch2.pro
1005  S R Q P C Q N G G R C V Q T G - - A Y C L C P P G W S G R L  Notch3.pro
848   A Q K P C P R N S H C L Q T G P S F H C L C L Q G W T G P L  Notch4.pro

1095  C D V P S V S C E V A A Q R Q G V D V A R L C Q H G G L C V  Notch1.pro
1098  C D V P N V S C D I A A S R R G V L V E H L C Q H S G V C I  Notch2.pro
1033  C D I R S L P C R E A A A Q I G V R L E Q L C Q A G G Q C V  Notch3.pro
878   C N L P L S S C Q K A A L S Q G I D V S S L C H N G G L C V  Notch4.pro

1125  D A G N T H H C R C Q A G Y T G S Y C E D L V D E C S P S P  Notch1.pro
1128  N A G N T H Y C Q C P L G Y T G S Y C E E Q L D E C A S N P  Notch2.pro
1063  D E D S S H Y C V C P E G R T G S H C E Q E V D P C L A Q P  Notch3.pro
908   D S G P S Y F C H C P P G F Q G S L C Q D H V N P C E S R P  Notch4.pro

1155  C Q N G A T C T D Y L G G Y S C K C V A G Y H G V N C S E E  Notch1.pro
1158  C Q H G A T C S D F I G G Y R C E C V P G Y Q G V N C E Y E  Notch2.pro
1093  C Q H G G T C R G Y M G G Y M C E C L P G Y N G D N C E D D  Notch3.pro
938   C Q N G A T C M A Q P S G Y L C Q C A P G Y D G Q N C S K E  Notch4.pro

1185  I D E C L S H P C Q N G G T C L D L P N T Y K C S C P R G T  Notch1.pro
1188  V D E C Q N Q P C Q N G G T C I D L V N H F K C S C P P G T  Notch2.pro
1123  V D E C A S Q P C Q H G G S C I D L V A R Y L C S C P P G T  Notch3.pro
968   L D A C Q S Q P C H N - - - - - - - - - - - - - - - - - - -  Notch4.pro

1215  Q G V H C E I N V D D C N P P V D P V S R S P K C F N N G T  Notch1.pro
1218  R G L L C E E N I D D C - - - - - - - A R G P H C L N G G Q  Notch2.pro
1153  L G V L C E I N E D D C G P G - P P L D S G P R C L H N G T  Notch3.pro
979   - - - - - - - - - - - - - - - - - - - - - - - - - - - H G T  Notch4.pro

1245  C V D Q V G G Y S C T C P P G F V G E R C E G D V N E C L S  Notch1.pro
1241  C M D R I G G Y S C R C L P G F A G E R C E G D I N E C L S  Notch2.pro
1182  C V D L V G G F R C T C P P G Y T G L R C E A D I N E C R S  Notch3.pro
982   C T P K P G G F H C A C P P G F V G L R C E G D V D E C L D  Notch4.pro

1275  N P C D A R G T Q N C V Q R V N - D F H C E C R A G H T G R  Notch1.pro
1271  N P C S S E G S L D C I Q L T N - D Y L C V C R S A F T G R  Notch2.pro
1212  G A C H A A H T R D C L Q D P G G G F R C L C H A G F S G P  Notch3.pro
1012  Q P C H P T G T A A C H S L A N - A F Y C Q C L P G H T G Q  Notch4.pro

1304  R C E S V I N G C K G K P C K N G G T C A V A S N T A R G -  Notch1.pro
1300  H C E T F V D V C P Q M P C L N G G T C A V A S N M P D G -  Notch2.pro
1242  R C Q T V L S P C E S Q P C Q H G G Q C R P S P G P G G G L  Notch3.pro
1041  W C E V E I D P C H S Q P C F H G G T C E A T A G S P L G -  Notch4.pro

1333  - F I C K C P A G F E G A T C E N D A R T C G S L R C L N G  Notch1.pro
1329  - F I C R C P P G F S G A R C Q S - - - S C G Q V K C R K G  Notch2.pro
1272  T F T C H C A Q P F W G P R C E R V A R S C R E L Q C P V G  Notch3.pro
1070  - F I C H C P K G F E G P T C S H R A P S C G F H H C H H G  Notch4.pro

1362  G T C I S G P R S - - - P T C L C L G P F T G P E C Q F P A  Notch1.pro
1355  E Q C V H T A S G - - - P R C F C P S P R D - - - C E S G C  Notch2.pro
1302  V P C Q Q T P R G - - - P R C A C P P G L S G P S C R S F P  Notch3.pro
1099  G L C L P S P K P G F P P R C A C L S G Y G G P D C L T P P  Notch4.pro
```

FIGURE 2D

```
1389  S S P - - - - - - C L G G N P C Y N Q G T C E P T S - - E S  Notch1.pro
1379  A S - - - - - - - - - - - S P C Q H G G S C H P Q R - - Q P  Notch2.pro
1329  G S P P G A S N A S C A A A P C L H G G S C R P A P - - L A  Notch3.pro
1129  A P K G - - - - - C G P P S P C L Y N G S C S E T T G L G G  Notch4.pro

1411  P F Y R C L C P A K F N G L L C H I L D Y S F G G G A G R D  Notch1.pro
1396  P Y Y S C Q C A P P F S G S R C E L Y T - - - - - - - - - -  Notch2.pro
1357  P F F R C A C A Q G W T G P R C E A P A - - - - - - - - - A  Notch3.pro
1154  P G F R C S C P H S S P G P R C Q K P G - - - - - - - - - -  Notch4.pro

1441  I P P P L I E E A C E L P E C Q E D A G N K V C S L Q C N N  Notch1.pro
1416  A P P S T P P A T C L S Q Y C A D K A R D G V C D E A C N S  Notch2.pro
1378  A P E V S E E P R C P R A A C Q A K R G D Q R C D R E C N S  Notch3.pro
1174  - - - - A K G - - - - - - - C E G R S G D G A C D A G C S G  Notch4.pro

1471  H A C G W D G G D C S L N F N D P W K N C T Q S L Q C W K Y  Notch1.pro
1446  H A C Q W D G G D C S L T M E N P W A N C S S P L P C W D Y  Notch2.pro
1408  P G C G W D G G D C S L S V G D P W R Q C - E A L Q C W R L  Notch3.pro
1193  P G G N W D G G D C S L G V P D P W K G C P S H S R C W L L  Notch4.pro

1501  F S D G H C D S Q C N S A G C L F D G F D C Q R A - - E G Q  Notch1.pro
1476  I N N - Q C D E L C N T V E C L F D N F E C Q G N - - S K T  Notch2.pro
1437  F N N S R C D P A C S S P A C L Y D N F D C H A G G R E R T  Notch3.pro
1223  F R D G Q C H P Q C D S E E C L F D G Y D C E T P - - - P A  Notch4.pro

1529  C N P L Y D Q Y C K D H F S D G H C D Q G C N S A E C E W D  Notch1.pro
1503  C K - - Y D K Y C A D H F K D N H C D Q G C N S E E C G W D  Notch2.pro
1467  C N P V Y E K Y C A D H F A D G R C D Q G C N T E E C G W D  Notch3.pro
1250  C T P A Y D Q Y C H D H F H N G H C E K G C N T A E C G W D  Notch4.pro

1559  G L D C A E H V P E R L A A G T L V V V V L M P P E Q L R N  Notch1.pro
1531  G L D C A A D Q P E N L A E G T L V I V V L M P P E Q L L Q  Notch2.pro
1497  G L D C A S E V P A L L A R G V L V L T V L L P P E E L L R  Notch3.pro
1280  G G D C R P E D G D P E W G P S L A L L V V L S P P A L D Q  Notch4.pro

1589  S S F H F L R E L S R V L H T N V V F K R D A H G Q Q M I F  Notch1.pro
1561  D A R S F L R A L G T L L H T N L R I K R D S Q G E L M V Y  Notch2.pro
1527  S S A D F L Q R L S A I L R T S L R F R L D A H G Q A M V F  Notch3.pro
1310  Q L F A L A R V L S L T L R V G L W V R K D R D G R D M V Y  Notch4.pro

1619  P Y Y G R E E E L R K H P I K R A A E G W A A P D A L L G Q  Notch1.pro
1591  P Y Y G E K S A A M K K - - - - - - - - Q - - - - - - - - R  Notch2.pro
1557  P Y H R P S P G S E P R - - - - - - - - - - - - - - - - - -  Notch3.pro
1340  P Y P G A R A E E K L G - - - - - - - - G T R D P T Y Q E R  Notch4.pro

1649  V K A S L L P G G S E G G R R R R E L D P M D V R G S I V Y  Notch1.pro
1605  M T R R S L P G E - - - - - - - Q E - - - Q E V A G S K V F  Notch2.pro
1569  A R R E L A P - - - - - - - - - - - - - - - E V I G S V V M  Notch3.pro
1362  A A P Q T Q P L G - - - - - - - - K E T D S L S A G F V V V  Notch4.pro

1679  L E I D N R Q C V Q - - A S S Q C F Q S A T D V A A F L G A  Notch1.pro
1625  L E I D N R Q C V Q - - D S D H C F K N T D A A A A L L A S  Notch2.pro
1584  L E I D N R L C L Q S P E N D H C F P D A Q S A A D Y L G A  Notch3.pro
1384  M G V D L S R C G P D H P A S R C P W D P G L L L R F L A A  Notch4.pro

1707  L A S L G S L N - - I P Y K I E A V Q S E T V E P P P P - -  Notch1.pro
1653  H A I Q G T L S - - Y P - - L V S V V S E S L T P - - - - -  Notch2.pro
1614  L S A V E R L D - - F P Y P L R D V R G E P L E P P E - - -  Notch3.pro
1414  M A A V G A L E P L L P G P L L A V H P H A G T A P P A N Q  Notch4.pro
```

FIGURE 2E

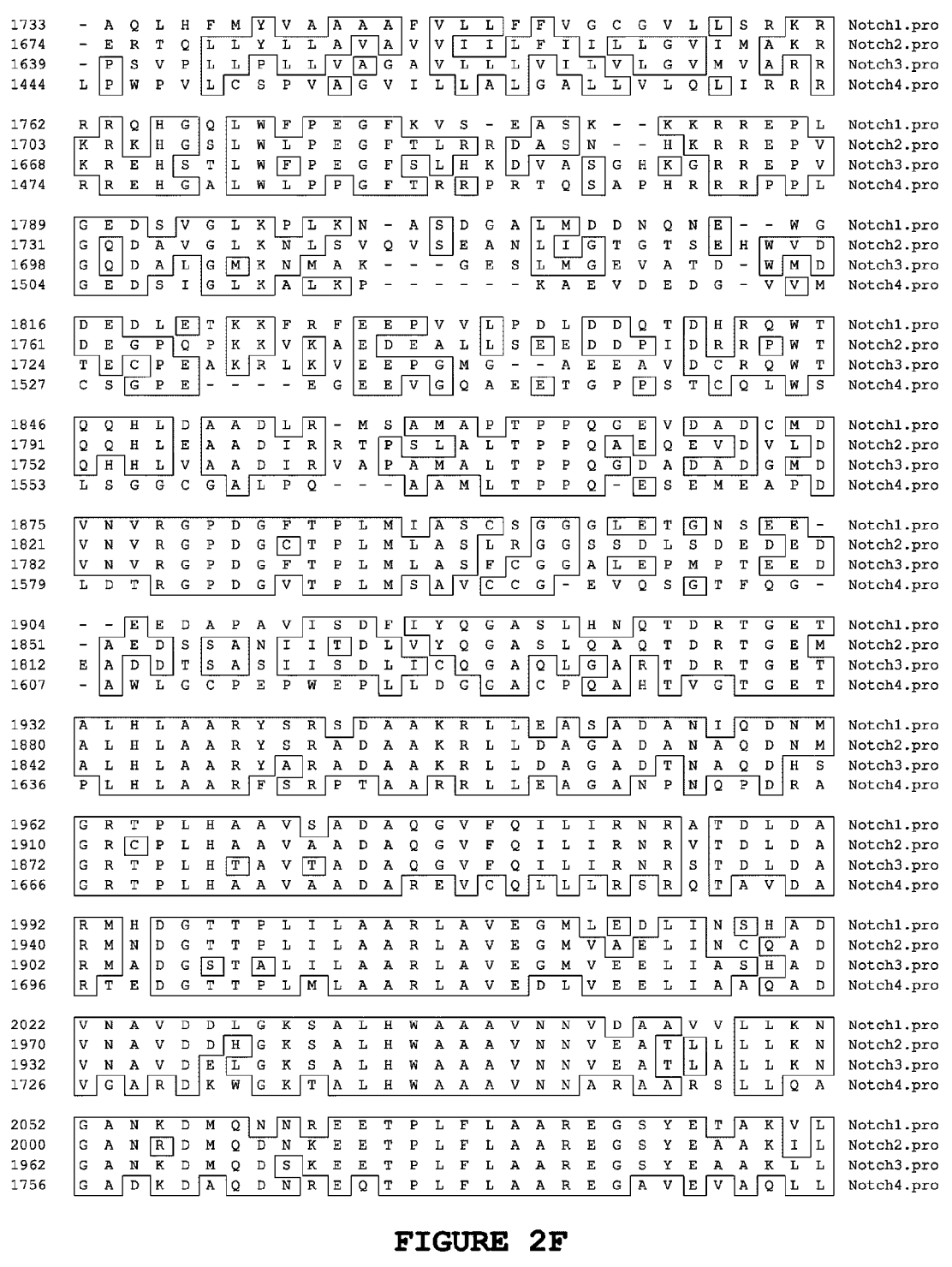

```
1733  - A Q L H F M Y V A A A A F V L L F F V G C G V L L S R K R  Notch1.pro
1674  - E R T Q L L Y L L A V A V V I I L F I I L L G V I M A K R  Notch2.pro
1639  - P S V P L L P L L V A G A V L L L V I L V L G V M V A R R  Notch3.pro
1444  L P W P V L C S P V A G V I L L A L G A L L V L Q L I R R R  Notch4.pro

1762  R R Q H G Q L W F P E G F K V S - E A S K - - K K R R E P L  Notch1.pro
1703  K R K H G S L W L P E G F T L R R D A S N - - H K R R E P V  Notch2.pro
1668  K R E H S T L W F P E G F S L H K D V A S G H K G R R E P V  Notch3.pro
1474  R R E H G A L W L P P G F T R R P R T Q S A P H R R R P P L  Notch4.pro

1789  G E D S V G L K P L K N - A S D G A L M D D N Q N E - - W G  Notch1.pro
1731  G Q D A V G L K N L S V Q V S E A N L I G T G T S E H W V D  Notch2.pro
1698  G Q D A L G M K N M A K - - - G E S L M G E V A T D - W M D  Notch3.pro
1504  G E D S I G L K A L K P - - - - - - K A E V D E D G - V V M  Notch4.pro

1816  D E D L E T K K F R F E E P V V L P D L D D Q T D H R Q W T  Notch1.pro
1761  D E G P Q P K K V K A E D E A L L S E E D D P I D R R P W T  Notch2.pro
1724  T E C P E A K R L K V E E P G M G - - A E E A V D C R Q W T  Notch3.pro
1527  C S G P E - - - - E G E E V G Q A E E T G P P S T C Q L W S  Notch4.pro

1846  Q Q H L D A A D L R - M S A M A P T P P Q G E V D A D C M D  Notch1.pro
1791  Q Q H L E A A D I R R T P S L A L T P P Q A E Q E V D V L D  Notch2.pro
1752  Q H H L V A A D I R V A P A M A L T P P Q G D A D A D G M D  Notch3.pro
1553  L S G G C G A L P Q - - - A A M L T P P Q - E S E M E A P D  Notch4.pro

1875  V N V R G P D G F T P L M I A S C S G G G L E T G N S E E -  Notch1.pro
1821  V N V R G P D G C T P L M L A S L R G G S S D L S D E D E D  Notch2.pro
1782  V N V R G P D G F T P L M L A S F C G G A L E P M P T E E D  Notch3.pro
1579  L D T R G P D G V T P L M S A V C C G - E V Q S G T F Q G -  Notch4.pro

1904  - - E E D A P A V I S D F I Y Q G A S L H N Q T D R T G E T  Notch1.pro
1851  - A E D S S A N I I T D L V Y Q G A S L Q A Q T D R T G E M  Notch2.pro
1812  E A D D T S A S I I S D L I C Q G A Q L G A R T D R T G E T  Notch3.pro
1607  - A W L G C P E P W E P L L D G G A C P Q A H T V G T G E T  Notch4.pro

1932  A L H L A A R Y S R S D A A K R L L E A S A D A N I Q D N M  Notch1.pro
1880  A L H L A A R Y S R A D A A K R L L D A G A D A N A Q D N M  Notch2.pro
1842  A L H L A A R Y A R A D A A K R L L D A G A D T N A Q D H S  Notch3.pro
1636  P L H L A A R F S R P T A A R R L L E A G A N P N Q P D R A  Notch4.pro

1962  G R T P L H A A V S A D A Q G V F Q I L I R N R A T D L D A  Notch1.pro
1910  G R C P L H A A V A A D A Q G V F Q I L I R N R V T D L D A  Notch2.pro
1872  G R T P L H T A V T A D A Q G V F Q I L I R N R S T D L D A  Notch3.pro
1666  G R T P L H A A V A A D A R E V C Q L L L R S R Q T A V D A  Notch4.pro

1992  R M H D G T T P L I L A A R L A V E G M L E D L I N S H A D  Notch1.pro
1940  R M N D G T T P L I L A A R L A V E G M V A E L I N C Q A D  Notch2.pro
1902  R M A D G S T A L I L A A R L A V E G M V E E L I A S H A D  Notch3.pro
1696  R T E D G T T P L M L A A R L A V E D L V E E L I A A Q A D  Notch4.pro

2022  V N A V D D L G K S A L H W A A A V N N V D A A V V L L K N  Notch1.pro
1970  V N A V D D H G K S A L H W A A A V N N V E A T L L L L K N  Notch2.pro
1932  V N A V D E L G K S A L H W A A A V N N V E A T L A L L K N  Notch3.pro
1726  V G A R D K W G K T A L H W A A A V N N A R A A R S L L Q A  Notch4.pro

2052  G A N K D M Q N N R E E T P L F L A A R E G S Y E T A K V L  Notch1.pro
2000  G A N R D M Q D N K E E T P L F L A A R E G S Y E A A K I L  Notch2.pro
1962  G A N K D M Q D S K E E T P L F L A A R E G S Y E A A K L L  Notch3.pro
1756  G A D K D A Q D N R E Q T P L F L A A R E G A V E V A Q L L  Notch4.pro
```

FIGURE 2F

```
2082 L D H F A N R D I T D H M D R L P R D I A Q E R M H H D I V Notch1.pro
2030 L D H F A N R D I T D H M D R L P R D V A R D R M H H D I V Notch2.pro
1992 L D H F A N R E I T D H L D R L P R D V A Q E R L H Q D I V Notch3.pro
1786 L G L G A A R E L R D Q A G L A P A D V A H Q R N H W D L L Notch4.pro

2112 R L L D E Y N L V R S P Q L H G A P L G G T P T L S P P L C Notch1.pro
2060 R L L D E Y N V T P S P - - P G T V L - - T S A L S P V I C Notch2.pro
2022 R L L D Q P S G P R S P - - P G P H G - - - - - L G P L L C Notch3.pro
1816 T L L E G A G P P E A R - - - - - - - - - - - - - - - - - - Notch4.pro

2142 S P N G Y L G S L K P G V Q G - K K V R K P S S K - - - - - Notch1.pro
2086 G P N R S F L S L K H T P M G - K K S R R P S A K S T M P T Notch2.pro
2045 P P G A F L P G L K A A Q S G S K K S R R P P G K - - - - - Notch3.pro
1828 - - - - - - - - - H K A T P G R E A G P F P R A R - - - - - Notch4.pro

2166 G L A C G S K E A K D L K - A R R K K S Q D G K G C L L D S Notch1.pro
2115 S L P N L A K E A K D A K G S R R K K S L S E K V Q L S E S Notch2.pro
2070 - - - - A G L G P Q G P R G R G K K L T L A C P G P L A D S Notch3.pro
1844 - - - - - - - - - - - - - - - - - - - T - - - - - - - - - V Notch4.pro

2195 S G M L S P V D S L E S P H G Y L S D V A S P P L L P S P - Notch1.pro
2145 S V T L S P V D S L E S P H T Y V S D T T S S P M I T S P G Notch2.pro
2096 S V T L S P V D S L D S P R P F G G P P A S P G G F P - - - Notch3.pro
1846 S V S V P P H G G G A L P R C R T L S A G A G P R G G - - - Notch4.pro

2224 F Q Q S P S V P L N H L P G M P D T H L G I G H L N V A A K Notch1.pro
2175 I L Q A S P N P M L A T A A P P A P V H A Q H A L S F S N L Notch2.pro
2123 - - - - - - - - - - - - - - - - - - L E G P Y A A A T A T A Notch3.pro
1873 - - - - - - - - - - - - - - - - - - - - G A C L Q A R T W S Notch4.pro

2254 P E M A A L G G G G R L A F E T G P P R L S H L P V A S G T Notch1.pro
2205 H E M Q P L A H G A S T V L P S V S Q L L S H H H I V S - - Notch2.pro
2135 V S L A Q L G G P G R A G L G R Q P P - - - - - - - - - - - Notch3.pro
1883 V D L A A R G G G A Y S H C R S L S G - - - - - - - - - - - Notch4.pro

2284 S T V L G S S S G G A L N F T V G G S T S L N G Q C E W L S Notch1.pro
2233 - - - P G S G S A G S L S R - - - - L H P V P V P A D W M N Notch2.pro
2154 - - - - - G G C V L S L G L - - - - L N P V A V P L D W A R Notch3.pro
1902 - - - - - V G A G G - - - - - - - - G - - - - - - - - - - - Notch4.pro

2314 R L Q S G M V P N Q Y N P L R G S V A P G P L S T Q A P S L Notch1.pro
2256 R M E V N E T - - Q Y N E M F G M V L A P A E G T H P G - - Notch2.pro
2175 - - - - - - - - - - - - - - - - L P P P A P P G P S - - - - Notch3.pro
1908 - - - - - - - - - - - - - - - - - - - P T P R G R R - - - - Notch4.pro

2344 Q H G M V G P L H S S L A A S A L S Q M M S Y Q G L P S T R Notch1.pro
2282 - - - - - - - - - I A - - P - - - - - - - - - - - - - Q S R Notch2.pro
2185 - - - - - - - - - - - - - - - - - - - - - - - - - - F L L P Notch3.pro
1915 - - - - - - - - - - - - - - - - - - - - - - - - - - - - - - Notch4.pro

2374 L A T Q P H L V Q T Q Q V Q P Q N L Q M Q Q Q N L Q P A N I Notch1.pro
2288 P P E G K H I T T P R E P L P P - I V T F Q - - L I P K - - Notch2.pro
2189 L A P G P Q L L N P G T P V S P - - - - - - - - - - - - - - Notch3.pro
1915 - - - - - - - F S A G M R G P R - - - - - - - - - - - - - - Notch4.pro

2404 Q Q Q Q S L Q P P P P P P Q P H L G V S S A A S G H L G R S Notch1.pro
2313 - - - G S I A Q P A G A P Q P Q S T C P P A V A G P L P T M Notch2.pro
2205 - - - - Q E R P P P Y L A V P G H G E E Y P V A G - - - - - Notch3.pro
1924 - - - - - - - P N P A I M R G R Y G V A A G R G G - - - - - Notch4.pro
```

FIGURE 2G

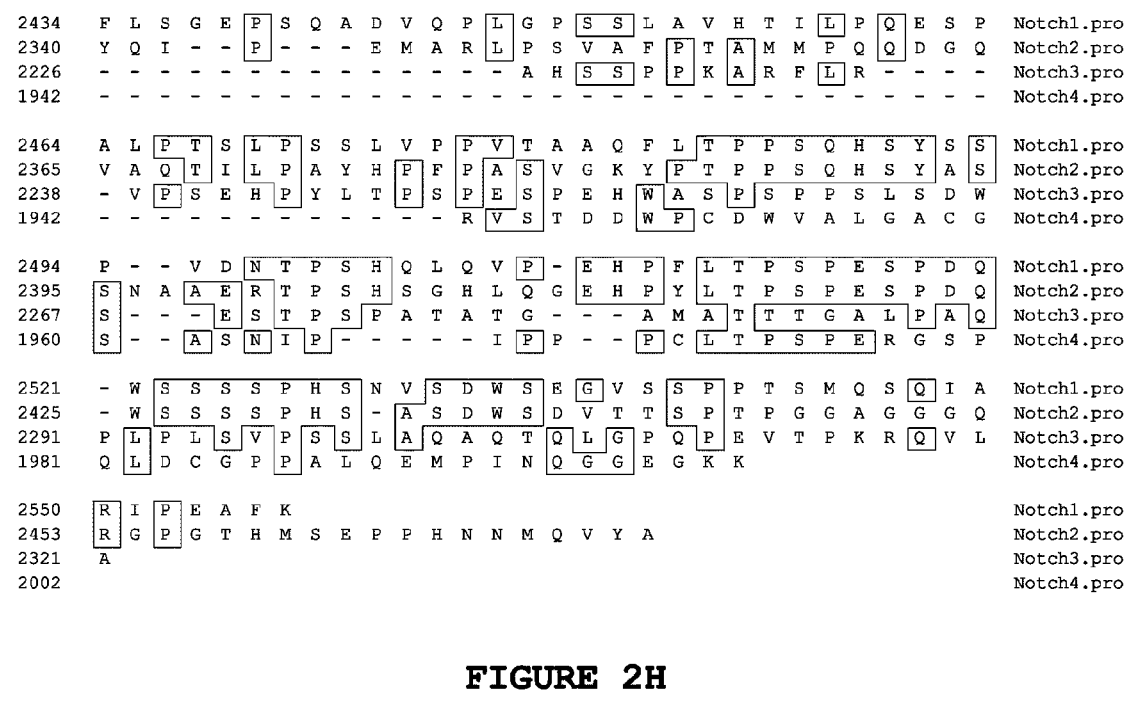

```
2434  F L S G E P S Q A D V Q P L G P S S L A V H T I L P Q E S P  Notch1.pro
2340  Y Q I - - P - - - E M A R L P S V A F P T A M M P Q Q D G Q  Notch2.pro
2226  - - - - - - - - - - - - - - A H S S P P K A R F L R - - - -  Notch3.pro
1942  - - - - - - - - - - - - - - - - - - - - - - - - - - - - - -  Notch4.pro

2464  A L P T S L P S S L V P P V T A A Q F L T P P S Q H S Y S S  Notch1.pro
2365  V A Q T I L P A Y H P F P A S V G K Y P T P P S Q H S Y A S  Notch2.pro
2238  - V P S E H P Y L T P S P E S P E H W A S P S P P S L S D W  Notch3.pro
1942  - - - - - - - - - - - - R V S T D D W P C D W V A L G A C G  Notch4.pro

2494  P - - V D N T P S H Q L Q V P - E H P F L T P S P E S P D Q  Notch1.pro
2395  S N A A E R T P S H S G H L Q G E H P Y L T P S P E S P D Q  Notch2.pro
2267  S - - - E S T P S P A T A T G - - - A M A T T T G A L P A Q  Notch3.pro
1960  S - - A S N I P - - - - - I P P - - P C L T P S P E R G S P  Notch4.pro

2521  - W S S S S P H S N V S D W S E G V S S P P T S M Q S Q I A  Notch1.pro
2425  - W S S S S P H S - A S D W S D V T T S P T P G G A G G G Q  Notch2.pro
2291  P L P L S V P S S L A Q A Q T Q L G P Q P E V T P K R Q V L  Notch3.pro
1981  Q L D C G P P A L Q E M P I N Q G G E G K K                  Notch4.pro

2550  R I P E A F K                                                Notch1.pro
2453  R G P G T H M S E P P H N N M Q V Y A                        Notch2.pro
2321  A                                                            Notch3.pro
2002                                                               Notch4.pro
```

FIGURE 2H

Figure 3: Statistics of amino acid sequence alignment for Notch 1-4.

Percent Identity

Divergence

| | 1 | 2 | 3 | 4 | | |
|---|---|---|---|---|---|---|
| 1 | | 56.1 | 52.7 | 42.6 | 1 | Notch1 |
| 2 | 64.9 | | 52.7 | 42.5 | 2 | Notch2 |
| 3 | 73.0 | 72.9 | | 43.4 | 3 | Notch3 |
| 4 | 102.0 | 102.4 | 99.3 | | 4 | Notch4 |
| | 1 | 2 | 3 | 4 | | |

FIGURE 4A mAb 256A-4 heavy chain variable region sequence:

EVQLVESGGGLVQPGGSLKLSCAASGFTFSHYYMSWVRQTPEKRLEWVAYISNGGGRTD
CDR-H1 CDR-H2

YPDSVKGRFTISRDNAKNTLHLQMSSLKSEDTAMYYCTRLDYFGGSPYFDYWGQGTTLT
CDR-H3

VSSA (SEQ ID NO: 2)

FIGURE 4B mAb 256A-4 light chain (kappa) variable region sequence

EIVLTQSPAITAASLGQKVTITCSASSSVSYMHWYQQKSGTSPKPWIYEISKLASGVPP
CDR-L1 CDR-L2

RFSGSGSGTSYSLTISSMEAEDAAIYYCQQWNYPLITFGSGTKLEIKRADAAPTV
CDR-L3

(SEQ ID NO: 3)

FIGURE 5A mAb 256A-8 heavy chain variable region sequence

EVQLVESGGGLVQPGGSLKLSCAASGFTFSHYYMSWVRQTPEKRLEWVAYINSGGGRTD
CDR-H1 CDR-H2

YPDSVKGRFTISRDNAKNTLHLQMSSLKSEDTAMYYCARLDYYGGSPYFDYWGQGTTLT
CDR-H3

VSSA (SEQ ID NO: 4)

FIGURE 5B mAb 256A-8 light chain (kappa) variable region sequence

EIVLTQSPAITAASLGQKVTITCSASSSVSYMHWYQQKSGTSPKPWIYEISKLASGVPA
CDR-L1 CDR-L2

RFSGSGSGTSYSLTISSMEAEDAAIYYCQQWNYPLITFGSGTKLEIKRADAAPTV
CDR-L3

(SEQ ID NO: 5)

ANTI-NOTCH 3 ANTIBODY INHIBITION OF JAGGED 1

ANTI-NOTCH 3 ANTIBODY INHIBITION OF JAGGED 2

ANTI-NOTCH 3 ANTIBODY INHIBITION OF DELTA-4

FIGURE 14A

| | | |
|---|---|---|
| 1 | A T G G G T C C A G G T G C A A G A G G | N3-leader Engineered. |
| 1 | A T G G G G C C G G G G G C C C G T G G | N3-leader NCBI.s |
| 21 | T A G A A G G C G T A G A A G G A G A C | N3-leader Engineered. |
| 21 | C C G C C G C C G C C G C C G T C G C C | N3-leader NCBI.s |
| 41 | C A A T G A G C C C A C C T C C T C C G | N3-leader Engineered. |
| 41 | C G A T G T C G C C G C C A C C G C C A | N3-leader NCBI.s |
| 61 | C C A C C T C C A G T G A G A G C A C T | N3-leader Engineered. |
| 61 | C C G C C A C C C G T G C G G G C G C T | N3-leader NCBI.s |
| 81 | G C C T T T G C T G T T G C T G C T G G | N3-leader Engineered. |
| 81 | G C C C C T G C T G C T G C T G C T A G | N3-leader NCBI.s |
| 101 | C T G G A C C T G G T G C A G C A G C T | N3-leader Engineered. |
| 101 | C G G G G C C G G G G G C T G C A G C C | N3-leader NCBI.s |
| 121 | C C T C C T T G C C T G G A C | N3-leader Engineered. |
| 121 | C C C C C T T G C C T G G A C | N3-leader NCBI.s |

FIGURE 16: Summary of subdomain swap and amino acid (aa) cluster swap sequence in first LIN12 domain and Mab binding strength in ELISA assays

| Expression constructs | SEQ ID NO | Wild type and swapped sequences of Notch3 1st LIN12 (L1) domain | 256A-4 | 256A-8 | G3 | % diff |
|---|---|---|---|---|---|---|
| Notch3-L1 | 9 | EPRCPRAACQAKRGDQRCDRECNSPGCGWDGGDCSLSVG | +++ | +++ | - | 0 |
| L1-sub1 | 10 | -EACELPE------------------------------- | +++ | +++ | - | 15.34 |
| L1-sub2 | 11 | ----------EDAGNKVCS-------------------- | - | - | - | 17.95 |
| L1-sub3 | 12 | -------------------LQCNNHACGWDGGDCSLNFN | - | - | - | 20.51 |
| L1-aa swap1 | 13 | ----------EDA-------------------------- | + | - | - | 7.69 |
| L1-aa swap2 | 14 | --------------NKV---------------------- | ++ | + | - | 7.69 |
| L1-aa swap3 | 15 | ------------------SLQ------------------ | - | - | - | 7.69 |
| L1-aa swap4 | 16 | ------------------------NHA------------ | +++ | +++ | - | 7.69 |
| L1-aa swap5 | 17 | ------------------------------------NFN | - | - | - | 7.69 |

In these ELISA experiments, binding of Mab 256A-4 and 256A-8 to Notch3-LD/Fc (L1) was used as positive standard, i.e. 100% binding. Binding read-out to swap recombinant proteins were compared to that of positive standard. +++ : >50% of standard binding; ++: 10-40% of standard binding; +: 10% to minimum positive signal. -: no binding, i.e. Mab G3 mean binding read-out +/- 3 X standard error. Mab G3 is a human IgG1 control Mab used as negative control.

FIGURE 17: Summary of subdomain swap and amino acid (aa) cluster swap sequence in second dimerization domain and Mab binding strength in ELISA assays

| Expression constructs | SEQ ID NO | Wild type and swapped sequences of Notch3 2nd dimerization (D2) domain | 256A-4 | 256A-8 | G3 | % diff |
|---|---|---|---|---|---|---|
| Notch3-D2 | 18 | ELAPEVIGSVVMLEIDNRLCLQSPENDHCFPDAQSAADYLGALSAVERLDFPYPLRDVRGEPLEPPEPS | +++ | +++ | - | 0 |
| D2-sub1 | 19 | ----DVRGSIVY--------------------------------------------------------- | - | - | - | 5.80 |
| D2-aa swap1 | 20 | ----DVR-------------------------------------------------------------- | - | - | - | 2.90 |
| D2-aa swap2 | 21 | ---------IVY--------------------------------------------------------- | +++ | +++ | - | 2.90 |
| D2-sub2 | 22 | ------------------QCVQAAASSQ----------------------------------------- | +++ | +++ | - | 11.59 |
| D2-sub3 | 23 | ------------------------------QSARTAAAF------------------------------ | +++ | +++ | - | 10.14 |
| D2-sub4 | 24 | -------------------------------------------ASLGSLNI------------------ | - | - | - | 10.14 |
| D2-aa swap3 | 25 | -------------------------------------------ASL----------------------- | +++ | +++ | - | 4.35 |
| D2-aa swap4 | 26 | ----------------------------------------------GS--------------------- | +++ | +++ | - | 2.90 |
| D2-aa swap5 | 27 | -------------------------------------------------NI------------------ | +++ | +++ | - | 2.90 |
| D2-sub5 | 28 | -----------------------------------------------------KIEAVQSETVEPPA-- | ++ | + | - | 13.04 |
| D2-aa swap6 | 29 | -----------------------------------------------------KIE------------- | - | - | - | 4.35 |
| D2-aa swap7 | 30 | --------------------------------------------------------AVQS--------- | +++ | +++ | - | 4.35 |
| D2-aa swap8 | 31 | -------------------------------------------------------------TVEPPA-- | +++ | +++ | - | 4.35 |

In these ELISA experiments, binding of Mab 256A-4 and 256A-8 to Notch3-LD/Fc (D2) was used as positive standard, i.e. 100% binding. Binding read-out to swap recombinant proteins were compared to that of positive standard. +++ : >50% of standard binding; ++: 10-40% of standard binding; +: 10% to minimum positive signal. -: no binding, i.e. Mab G3 mean binding read-out +/- 3 X standard error. Mab G3 is a human IgG1 control Mab used as negative control.

FIGURE 18: SCHEMATIC OF EPITOPE BINDING
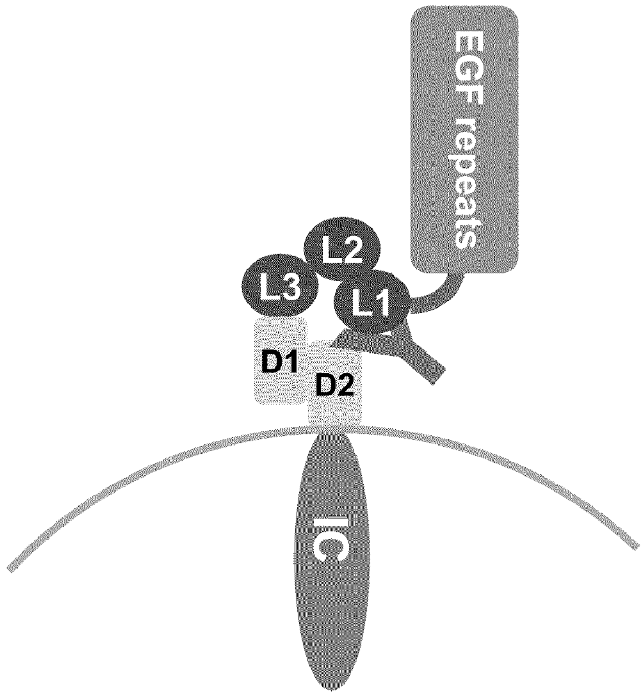
Notch3

SEQUENCE LISTING

<160> NUMBER OF SEQ ID NOS: 48

<210> SEQ ID NO 1
<211> LENGTH: 2321
<212> TYPE: PRT
<213> ORGANISM: Homo sapiens

<400> SEQUENCE: 1

```
Met Gly Pro Gly Ala Arg Gly Arg Arg Arg Arg Arg Arg Pro Met Ser
1               5                   10                  15

Pro Pro Pro Pro Pro Pro Pro Val Arg Ala Leu Pro Leu Leu Leu Leu
            20                  25                  30

Leu Ala Gly Pro Gly Ala Ala Ala Pro Pro Cys Leu Asp Gly Ser Pro
        35                  40                  45

Cys Ala Asn Gly Gly Arg Cys Thr Gln Leu Pro Ser Arg Glu Ala Ala
    50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
        115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
        355                 360                 365
```

-continued

```
Asn Pro Val Asn Gly Arg Ala Ile Cys Thr Cys Pro Pro Gly Phe Thr
    370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
        435                 440                 445

Arg Ile Gly Gln Phe Thr Cys Ile Cys Met Ala Gly Phe Thr Gly Thr
    450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
        515                 520                 525

Tyr Glu Cys Arg Cys Ala Glu Gly Phe Glu Gly Thr Leu Cys Asp Arg
    530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
        595                 600                 605

Pro Ser Gly Thr Thr Gly Val Asn Cys Glu Val Asn Ile Asp Asp Cys
    610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
        675                 680                 685

Pro Pro Leu Cys Leu Pro Pro Ser His Pro Cys Ala His Glu Pro Cys
    690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
        755                 760                 765

Cys Glu Leu Leu Ser Pro Cys Thr Pro Asn Pro Cys Glu His Gly Gly
    770                 775                 780

Arg Cys Glu Ser Ala Pro Gly Gln Leu Pro Val Cys Ser Cys Pro Gln
```

-continued

```
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
        835                 840                 845

Asp Ile Asn Asp Cys Asp Pro Asn Pro Cys Leu Asn Gly Gly Ser Cys
    850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
        915                 920                 925

Ser Pro Ser Ser Cys Phe Asn Gly Gly Thr Cys Val Asp Gly Val Asn
    930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu  Val Asp Trp Cys Ser  Arg Gln Pro
        995                 1000                1005

Cys Gln  Asn Gly Gly Arg Cys  Val Gln Thr Gly Ala  Tyr Cys Leu
    1010                 1015                 1020

Cys Pro  Pro Gly Trp Ser Gly  Arg Leu Cys Asp Ile  Arg Ser Leu
    1025                 1030                 1035

Pro Cys  Arg Glu Ala Ala Ala  Gln Ile Gly Val Arg  Leu Glu Gln
    1040                 1045                 1050

Leu Cys  Gln Ala Gly Gly Gln  Cys Val Asp Glu Asp  Ser Ser His
    1055                 1060                 1065

Tyr Cys  Val Cys Pro Glu Gly  Arg Thr Gly Ser His  Cys Glu Gln
    1070                 1075                 1080

Glu Val  Asp Pro Cys Leu Ala  Gln Pro Cys Gln His  Gly Gly Thr
    1085                 1090                 1095

Cys Arg  Gly Tyr Met Gly Gly  Tyr Met Cys Glu Cys  Leu Pro Gly
    1100                 1105                 1110

Tyr Asn  Gly Asp Asn Cys Glu  Asp Asp Val Asp Glu  Cys Ala Ser
    1115                 1120                 1125

Gln Pro  Cys Gln His Gly Gly  Ser Cys Ile Asp Leu  Val Ala Arg
    1130                 1135                 1140

Tyr Leu  Cys Ser Cys Pro Pro  Gly Thr Leu Gly Val  Leu Cys Glu
    1145                 1150                 1155

Ile Asn  Glu Asp Asp Cys Gly  Pro Gly Pro Pro Leu  Asp Ser Gly
    1160                 1165                 1170

Pro Arg  Cys Leu His Asn Gly  Thr Cys Val Asp Leu  Val Gly Gly
    1175                 1180                 1185

Phe Arg  Cys Thr Cys Pro Pro  Gly Tyr Thr Gly Leu  Arg Cys Glu
    1190                 1195                 1200
```

-continued

```
Ala Asp Ile Asn Glu Cys Arg Ser Gly Ala Cys His Ala Ala His
    1205                1210                1215

Thr Arg Asp Cys Leu Gln Asp Pro Gly Gly Gly Phe Arg Cys Leu
    1220                1225                1230

Cys His Ala Gly Phe Ser Gly Pro Arg Cys Gln Thr Val Leu Ser
    1235                1240                1245

Pro Cys Glu Ser Gln Pro Cys Gln His Gly Gly Gln Cys Arg Pro
    1250                1255                1260

Ser Pro Gly Pro Gly Gly Gly Leu Thr Phe Thr Cys His Cys Ala
    1265                1270                1275

Gln Pro Phe Trp Gly Pro Arg Cys Glu Arg Val Ala Arg Ser Cys
    1280                1285                1290

Arg Glu Leu Gln Cys Pro Val Gly Val Pro Cys Gln Gln Thr Pro
    1295                1300                1305

Arg Gly Pro Arg Cys Ala Cys Pro Pro Gly Leu Ser Gly Pro Ser
    1310                1315                1320

Cys Arg Ser Phe Pro Gly Ser Pro Pro Gly Ala Ser Asn Ala Ser
    1325                1330                1335

Cys Ala Ala Ala Pro Cys Leu His Gly Gly Ser Cys Arg Pro Ala
    1340                1345                1350

Pro Leu Ala Pro Phe Phe Arg Cys Ala Cys Ala Gln Gly Trp Thr
    1355                1360                1365

Gly Pro Arg Cys Glu Ala Pro Ala Ala Ala Pro Glu Val Ser Glu
    1370                1375                1380

Glu Pro Arg Cys Pro Arg Ala Ala Cys Gln Ala Lys Arg Gly Asp
    1385                1390                1395

Gln Arg Cys Asp Arg Glu Cys Asn Ser Pro Gly Cys Gly Trp Asp
    1400                1405                1410

Gly Gly Asp Cys Ser Leu Ser Val Gly Asp Pro Trp Arg Gln Cys
    1415                1420                1425

Glu Ala Leu Gln Cys Trp Arg Leu Phe Asn Asn Ser Arg Cys Asp
    1430                1435                1440

Pro Ala Cys Ser Ser Pro Ala Cys Leu Tyr Asp Asn Phe Asp Cys
    1445                1450                1455

His Ala Gly Gly Arg Glu Arg Thr Cys Asn Pro Val Tyr Glu Lys
    1460                1465                1470

Tyr Cys Ala Asp His Phe Ala Asp Gly Arg Cys Asp Gln Gly Cys
    1475                1480                1485

Asn Thr Glu Glu Cys Gly Trp Asp Gly Leu Asp Cys Ala Ser Glu
    1490                1495                1500

Val Pro Ala Leu Leu Ala Arg Gly Val Leu Val Leu Thr Val Leu
    1505                1510                1515

Leu Pro Pro Glu Glu Leu Leu Arg Ser Ser Ala Asp Phe Leu Gln
    1520                1525                1530

Arg Leu Ser Ala Ile Leu Arg Thr Ser Leu Arg Phe Arg Leu Asp
    1535                1540                1545

Ala His Gly Gln Ala Met Val Phe Pro Tyr His Arg Pro Ser Pro
    1550                1555                1560

Gly Ser Glu Pro Arg Ala Arg Arg Glu Leu Ala Pro Glu Val Ile
    1565                1570                1575

Gly Ser Val Val Met Leu Glu Ile Asp Asn Arg Leu Cys Leu Gln
    1580                1585                1590

Ser Pro Glu Asn Asp His Cys Phe Pro Asp Ala Gln Ser Ala Ala
    1595                1600                1605
```

-continued

```
Asp Tyr  Leu Gly Ala Leu Ser  Ala Val Glu Arg Leu  Asp Phe Pro
    1610                 1615                 1620

Tyr Pro  Leu Arg Asp Val Arg  Gly Glu Pro Leu Glu  Pro Pro Glu
    1625                 1630                 1635

Pro Ser  Val Pro Leu Leu Pro  Leu Leu Val Ala Gly  Ala Val Leu
    1640                 1645                 1650

Leu Leu  Val Ile Leu Val Leu  Gly Val Met Val Ala  Arg Arg Lys
    1655                 1660                 1665

Arg Glu  His Ser Thr Leu Trp  Phe Pro Glu Gly Phe  Ser Leu His
    1670                 1675                 1680

Lys Asp  Val Ala Ser Gly His  Lys Gly Arg Arg Glu  Pro Val Gly
    1685                 1690                 1695

Gln Asp  Ala Leu Gly Met Lys  Asn Met Ala Lys Gly  Glu Ser Leu
    1700                 1705                 1710

Met Gly  Glu Val Ala Thr Asp  Trp Met Asp Thr Glu  Cys Pro Glu
    1715                 1720                 1725

Ala Lys  Arg Leu Lys Val Glu  Glu Pro Gly Met Gly  Ala Glu Glu
    1730                 1735                 1740

Ala Val  Asp Cys Arg Gln Trp  Thr Gln His His Leu  Val Ala Ala
    1745                 1750                 1755

Asp Ile  Arg Val Ala Pro Ala  Met Ala Leu Thr Pro  Pro Gln Gly
    1760                 1765                 1770

Asp Ala  Asp Ala Asp Gly Met  Asp Val Asn Val Arg  Gly Pro Asp
    1775                 1780                 1785

Gly Phe  Thr Pro Leu Met Leu  Ala Ser Phe Cys Gly  Gly Ala Leu
    1790                 1795                 1800

Glu Pro  Met Pro Thr Glu Glu  Asp Glu Ala Asp Asp  Thr Ser Ala
    1805                 1810                 1815

Ser Ile  Ile Ser Asp Leu Ile  Cys Gln Gly Ala Gln  Leu Gly Ala
    1820                 1825                 1830

Arg Thr  Asp Arg Thr Gly Glu  Thr Ala Leu His Leu  Ala Ala Arg
    1835                 1840                 1845

Tyr Ala  Arg Ala Asp Ala Ala  Lys Arg Leu Leu Asp  Ala Gly Ala
    1850                 1855                 1860

Asp Thr  Asn Ala Gln Asp His  Ser Gly Arg Thr Pro  Leu His Thr
    1865                 1870                 1875

Ala Val  Thr Ala Asp Ala Gln  Gly Val Phe Gln Ile  Leu Ile Arg
    1880                 1885                 1890

Asn Arg  Ser Thr Asp Leu Asp  Ala Arg Met Ala Asp  Gly Ser Thr
    1895                 1900                 1905

Ala Leu  Ile Leu Ala Ala Arg  Leu Ala Val Glu Gly  Met Val Glu
    1910                 1915                 1920

Glu Leu  Ile Ala Ser His Ala  Asp Val Asn Ala Val  Asp Glu Leu
    1925                 1930                 1935

Gly Lys  Ser Ala Leu His Trp  Ala Ala Ala Val Asn  Asn Val Glu
    1940                 1945                 1950

Ala Thr  Leu Ala Leu Leu Lys  Asn Gly Ala Asn Lys  Asp Met Gln
    1955                 1960                 1965

Asp Ser  Lys Glu Glu Thr Pro  Leu Phe Leu Ala Ala  Arg Glu Gly
    1970                 1975                 1980

Ser Tyr  Glu Ala Ala Lys Leu  Leu Leu Asp His Phe  Ala Asn Arg
    1985                 1990                 1995

Glu Ile  Thr Asp His Leu Asp  Arg Leu Pro Arg Asp  Val Ala Gln
```

2000 2005 2010

Glu Arg Leu His Gln Asp Ile Val Arg Leu Leu Asp Gln Pro Ser
2015 2020 2025

Gly Pro Arg Ser Pro Pro Gly Pro His Gly Leu Gly Pro Leu Leu
2030 2035 2040

Cys Pro Pro Gly Ala Phe Leu Pro Gly Leu Lys Ala Ala Gln Ser
2045 2050 2055

Gly Ser Lys Lys Ser Arg Arg Pro Pro Gly Lys Ala Gly Leu Gly
2060 2065 2070

Pro Gln Gly Pro Arg Gly Arg Gly Lys Lys Leu Thr Leu Ala Cys
2075 2080 2085

Pro Gly Pro Leu Ala Asp Ser Ser Val Thr Leu Ser Pro Val Asp
2090 2095 2100

Ser Leu Asp Ser Pro Arg Pro Phe Gly Gly Pro Pro Ala Ser Pro
2105 2110 2115

Gly Gly Phe Pro Leu Glu Gly Pro Tyr Ala Ala Ala Thr Ala Thr
2120 2125 2130

Ala Val Ser Leu Ala Gln Leu Gly Gly Pro Gly Arg Ala Gly Leu
2135 2140 2145

Gly Arg Gln Pro Pro Gly Gly Cys Val Leu Ser Leu Gly Leu Leu
2150 2155 2160

Asn Pro Val Ala Val Pro Leu Asp Trp Ala Arg Leu Pro Pro Pro
2165 2170 2175

Ala Pro Pro Gly Pro Ser Phe Leu Leu Pro Leu Ala Pro Gly Pro
2180 2185 2190

Gln Leu Leu Asn Pro Gly Thr Pro Val Ser Pro Gln Glu Arg Pro
2195 2200 2205

Pro Pro Tyr Leu Ala Val Pro Gly His Gly Glu Glu Tyr Pro Val
2210 2215 2220

Ala Gly Ala His Ser Ser Pro Pro Lys Ala Arg Phe Leu Arg Val
2225 2230 2235

Pro Ser Glu His Pro Tyr Leu Thr Pro Ser Pro Glu Ser Pro Glu
2240 2245 2250

His Trp Ala Ser Pro Ser Pro Pro Ser Leu Ser Asp Trp Ser Glu
2255 2260 2265

Ser Thr Pro Ser Pro Ala Thr Ala Thr Gly Ala Met Ala Thr Thr
2270 2275 2280

Thr Gly Ala Leu Pro Ala Gln Pro Leu Pro Leu Ser Val Pro Ser
2285 2290 2295

Ser Leu Ala Gln Ala Gln Thr Gln Leu Gly Pro Gln Pro Glu Val
2300 2305 2310

Thr Pro Lys Arg Gln Val Leu Ala
2315 2320

<210> SEQ ID NO 2
<211> LENGTH: 122
<212> TYPE: PRT
<213> ORGANISM: Artificial sequence
<220> FEATURE:
<223> OTHER INFORMATION: HEAVY CHAIN VARIABLE REGION OF MAB 256A-4

<400> SEQUENCE: 2

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Ser His Tyr
20 25 30

```
Tyr Met Ser Trp Val Arg Gln Thr Pro Glu Lys Arg Leu Glu Trp Val
        35                  40                  45

Ala Tyr Ile Ser Asn Gly Gly Gly Arg Thr Asp Tyr Pro Asp Ser Val
    50                  55                  60

Lys Gly Arg Phe Thr Ile Ser Arg Asp Asn Ala Lys Asn Thr Leu His
65                  70                  75                  80

Leu Gln Met Ser Ser Leu Lys Ser Glu Asp Thr Ala Met Tyr Tyr Cys
                85                  90                  95

Thr Arg Leu Asp Tyr Phe Gly Gly Ser Pro Tyr Phe Asp Tyr Trp Gly
            100                 105                 110

Gln Gly Thr Thr Leu Thr Val Ser Ser Ala
        115                 120


<210> SEQ ID NO 3
<211> LENGTH: 114
<212> TYPE: PRT
<213> ORGANISM: Artificial sequence
<220> FEATURE:
<223> OTHER INFORMATION: LIGHT CHAIN VARIABLE REGION OF MAB 256 A-4

<400> SEQUENCE: 3

Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Ser Val Ser Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Pro Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Ile Thr
                85                  90                  95

Phe Gly Ser Gly Thr Lys Leu Glu Ile Lys Arg Ala Asp Ala Ala Pro
            100                 105                 110

Thr Val


<210> SEQ ID NO 4
<211> LENGTH: 122
<212> TYPE: PRT
<213> ORGANISM: Artificial sequence
<220> FEATURE:
<223> OTHER INFORMATION: HEAVY CHAIN VARIABLE REGION OF MAB 256 A-8

<400> SEQUENCE: 4

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser His Tyr
            20                  25                  30

Tyr Met Ser Trp Val Arg Gln Thr Pro Glu Lys Arg Leu Glu Trp Val
        35                  40                  45

Ala Tyr Ile Asn Ser Gly Gly Gly Arg Thr Asp Tyr Pro Asp Ser Val
    50                  55                  60

Lys Gly Arg Phe Thr Ile Ser Arg Asp Asn Ala Lys Asn Thr Leu His
65                  70                  75                  80

Leu Gln Met Ser Ser Leu Lys Ser Glu Asp Thr Ala Met Tyr Tyr Cys
                85                  90                  95
```

```
Ala Arg Leu Asp Tyr Tyr Gly Gly Ser Pro Tyr Phe Asp Tyr Trp Gly
            100                 105                 110

Gln Gly Thr Thr Leu Thr Val Ser Ser Ala
        115                 120


<210> SEQ ID NO 5
<211> LENGTH: 114
<212> TYPE: PRT
<213> ORGANISM: Artificial sequence
<220> FEATURE:
<223> OTHER INFORMATION: LIGHT CHAIN VARIABLE REGION OF MAB 256 A-8

<400> SEQUENCE: 5

Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Ser Val Ser Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Ile Thr
                85                  90                  95

Phe Gly Ser Gly Thr Lys Leu Glu Ile Lys Arg Ala Asp Ala Ala Pro
            100                 105                 110

Thr Val


<210> SEQ ID NO 6
<211> LENGTH: 45
<212> TYPE: PRT
<213> ORGANISM: Artificial sequence
<220> FEATURE:
<223> OTHER INFORMATION: MODIFIED NOTCH 3 LEADER SEQUENCE

<400> SEQUENCE: 6

Met Gly Pro Gly Ala Arg Gly Arg Arg Arg Arg Arg Arg Pro Met Ser
1               5                   10                  15

Pro Pro Pro Pro Pro Pro Pro Val Arg Ala Leu Pro Leu Leu Leu Leu
            20                  25                  30

Leu Ala Gly Pro Gly Ala Ala Ala Pro Pro Cys Leu Asp
        35                  40                  45


<210> SEQ ID NO 7
<211> LENGTH: 55
<212> TYPE: DNA
<213> ORGANISM: Artificial sequence
<220> FEATURE:
<223> OTHER INFORMATION: OLIGONUCLEOTIDE PRIMER

<400> SEQUENCE: 7

gctcgagctc gtgggaaaat accgtgggaa aatgaaccgt gggaaaatct cgtgg          55


<210> SEQ ID NO 8
<211> LENGTH: 35
<212> TYPE: DNA
<213> ORGANISM: Artificial sequence
<220> FEATURE:
<223> OTHER INFORMATION: OLIGONUCLEOTIDE PRIMER

<400> SEQUENCE: 8
```

gctcgagatt ttcccacgag attttcccac ggttc 35

<210> SEQ ID NO 9
<211> LENGTH: 39
<212> TYPE: PRT
<213> ORGANISM: Artificial sequence
<220> FEATURE:
<223> OTHER INFORMATION: NOTCH 3 LIN 12 DOMAIN

<400> SEQUENCE: 9

```
Glu Pro Arg Cys Pro Arg Ala Ala Cys Gln Ala Lys Arg Gly Asp Gln
1               5                   10                  15

Arg Cys Asp Arg Glu Cys Asn Ser Pro Gly Cys Gly Trp Asp Gly Gly
            20                  25                  30

Asp Cys Ser Leu Ser Val Gly
        35
```

<210> SEQ ID NO 10
<211> LENGTH: 39
<212> TYPE: PRT
<213> ORGANISM: Artificial sequence
<220> FEATURE:
<223> OTHER INFORMATION: NOTCH 3/ NOTCH1 LIN 12 DOMAIN SWAP (FIG 16 L1-SUB1)

<400> SEQUENCE: 10

```
Glu Glu Ala Cys Glu Leu Pro Glu Cys Gln Ala Lys Arg Gly Asp Gln
1               5                   10                  15

Arg Cys Asp Arg Glu Cys Asn Ser Pro Gly Cys Gly Trp Asp Gly Gly
            20                  25                  30

Asp Cys Ser Leu Ser Val Gly
        35
```

<210> SEQ ID NO 11
<211> LENGTH: 39
<212> TYPE: PRT
<213> ORGANISM: Artificial sequence
<220> FEATURE:
<223> OTHER INFORMATION: NOTCH 3 / NOTCH 1 LIN 12 DOMAIN SWAP (FIG. 16 L1-SUB2)

<400> SEQUENCE: 11

```
Glu Pro Arg Cys Pro Arg Ala Ala Cys Gln Glu Asp Ala Gly Asn Lys
1               5                   10                  15

Val Cys Ser Arg Glu Cys Asn Ser Pro Gly Cys Gly Trp Asp Gly Gly
            20                  25                  30

Asp Cys Ser Leu Ser Val Gly
        35
```

<210> SEQ ID NO 12
<211> LENGTH: 39
<212> TYPE: PRT
<213> ORGANISM: Artificial sequence
<220> FEATURE:
<223> OTHER INFORMATION: NOTCH 3 / NOTCH 1 LIN 12 DOMAIN SWAP (FIG. 16 L1-SUB3)

<400> SEQUENCE: 12

```
Glu Pro Arg Cys Pro Arg Ala Ala Cys Gln Ala Lys Arg Gly Asp Gln
1               5                   10                  15

Arg Cys Asp Leu Gln Cys Asn Asn His Ala Cys Gly Trp Asp Gly Gly
            20                  25                  30

Asp Cys Ser Leu Asn Phe Asn
        35
```

<210> SEQ ID NO 13
<211> LENGTH: 39
<212> TYPE: PRT
<213> ORGANISM: Artificial sequence
<220> FEATURE:
<223> OTHER INFORMATION: NOTCH 3/ NOTCH 1 LIN12 AMINO ACID SWAP (FIG 16
L1-AA SWAP 1)

<400> SEQUENCE: 13

```
Glu Pro Arg Cys Pro Arg Ala Ala Cys Gln Glu Asp Ala Gly Asp Gln
1               5                   10                  15

Arg Cys Asp Arg Glu Cys Asn Ser Pro Gly Cys Gly Trp Asp Gly Gly
            20                  25                  30

Asp Cys Ser Leu Ser Val Gly
        35
```

<210> SEQ ID NO 14
<211> LENGTH: 39
<212> TYPE: PRT
<213> ORGANISM: Artificial sequence
<220> FEATURE:
<223> OTHER INFORMATION: NOTCH 3/ NOTCH 1 LIN12 AMINO ACID SWAP (FIG 16
L1-AA SWAP 2)

<400> SEQUENCE: 14

```
Glu Pro Arg Cys Pro Arg Ala Ala Cys Gln Ala Lys Arg Gly Asn Lys
1               5                   10                  15

Val Cys Asp Arg Glu Cys Asn Ser Pro Gly Cys Gly Trp Asp Gly Gly
            20                  25                  30

Asp Cys Ser Leu Ser Val Gly
        35
```

<210> SEQ ID NO 15
<211> LENGTH: 39
<212> TYPE: PRT
<213> ORGANISM: Artificial sequence
<220> FEATURE:
<223> OTHER INFORMATION: NOTCH 3/ NOTCH 1 LIN12 AMINO ACID SWAP (FIG 16
L1-AA SWAP 3)

<400> SEQUENCE: 15

```
Glu Pro Arg Cys Pro Arg Ala Ala Cys Gln Ala Lys Arg Gly Asp Gln
1               5                   10                  15

Arg Cys Ser Leu Gln Cys Asn Ser Pro Gly Cys Gly Trp Asp Gly Gly
            20                  25                  30

Asp Cys Ser Leu Ser Val Gly
        35
```

<210> SEQ ID NO 16
<211> LENGTH: 39
<212> TYPE: PRT
<213> ORGANISM: Artificial sequence
<220> FEATURE:
<223> OTHER INFORMATION: NOTCH 3/ NOTCH 1 LIN12 AMINO ACID SWAP (FIG 16
L1-AA SWAP 4)

<400> SEQUENCE: 16

```
Glu Pro Arg Cys Pro Arg Ala Ala Cys Gln Ala Lys Arg Gly Asp Gln
1               5                   10                  15

Arg Cys Asp Arg Glu Cys Asn Asn His Ala Cys Gly Trp Asp Gly Gly
            20                  25                  30

Asp Cys Ser Leu Ser Val Gly
        35
```

-continued

<210> SEQ ID NO 17
<211> LENGTH: 39
<212> TYPE: PRT
<213> ORGANISM: Artificial sequence
<220> FEATURE:
<223> OTHER INFORMATION: NOTCH 3/ NOTCH 1 LIN12 AMINO ACID SWAP (FIG 16 L1-AA SWAP 5)

<400> SEQUENCE: 17

```
Glu Pro Arg Cys Pro Arg Ala Ala Cys Gln Ala Lys Arg Gly Asp Gln
1               5                   10                  15

Arg Cys Asp Arg Glu Cys Asn Ser Pro Gly Cys Gly Trp Asp Gly Gly
            20                  25                  30

Asp Cys Ser Leu Asn Phe Asn
        35
```

<210> SEQ ID NO 18
<211> LENGTH: 69
<212> TYPE: PRT
<213> ORGANISM: Artificial sequence
<220> FEATURE:
<223> OTHER INFORMATION: NOTCH 3 DIMERIZATION DOMAIN 2 (FIG 17 D2)

<400> SEQUENCE: 18

```
Glu Leu Ala Pro Glu Val Ile Gly Ser Val Val Met Leu Glu Ile Asp
1               5                   10                  15

Asn Arg Leu Cys Leu Gln Ser Pro Glu Asn Asp His Cys Phe Pro Asp
            20                  25                  30

Ala Gln Ser Ala Ala Asp Tyr Leu Gly Ala Leu Ser Ala Val Glu Arg
        35                  40                  45

Leu Asp Phe Pro Tyr Pro Leu Arg Asp Val Arg Gly Glu Pro Leu Glu
    50                  55                  60

Pro Pro Glu Pro Ser
65
```

<210> SEQ ID NO 19
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN SWAP (FIG 17 D2-SUB1)

<400> SEQUENCE: 19

```
Glu Leu Ala Pro Asp Val Arg Gly Ser Ile Val Tyr Leu Glu Ile Asp
1               5                   10                  15

Asn Arg Leu Cys Leu Gln Ser Pro Glu Asn Asp His Cys Phe Pro Asp
            20                  25                  30

Ala Gln Ser Ala Ala Asp Tyr Leu Gly Ala Leu Ser Ala Val Glu Arg
        35                  40                  45

Leu Asp Phe Pro Tyr Pro Leu Arg Asp Val Arg Gly Glu Pro Leu Glu
    50                  55                  60

Pro Pro Glu Pro Ser
65
```

<210> SEQ ID NO 20
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN SWAP (FIG 17 D2-SUB2)

<400> SEQUENCE: 20

Glu Leu Ala Pro Glu Val Ile Gly Ser Val Val Met Leu Glu Ile Asp
1 5 10 15

Asn Arg Gln Cys Val Gln Ala Ala Ala Ser Ser Gln Cys Phe Pro Asp
20 25 30

Ala Gln Ser Ala Ala Asp Tyr Leu Gly Ala Leu Ser Ala Val Glu Arg
35 40 45

Leu Asp Phe Pro Tyr Pro Leu Arg Asp Val Arg Gly Glu Pro Leu Glu
50 55 60

Pro Pro Glu Pro Ser
65

<210> SEQ ID NO 21
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN SWAP (FIG 17 D2-SUB3)

<400> SEQUENCE: 21

Glu Leu Ala Pro Glu Val Ile Gly Ser Val Val Met Leu Glu Ile Asp
1 5 10 15

Asn Arg Leu Cys Leu Gln Ser Pro Glu Asn Asp His Cys Phe Gln Ser
20 25 30

Ala Thr Asp Ala Ala Ala Phe Leu Gly Ala Leu Ser Ala Val Glu Arg
35 40 45

Leu Asp Phe Pro Tyr Pro Leu Arg Asp Val Arg Gly Glu Pro Leu Glu
50 55 60

Pro Pro Glu Pro Ser
65

<210> SEQ ID NO 22
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN SWAP (FIG 17 D2-SUB4)

<400> SEQUENCE: 22

Glu Leu Ala Pro Glu Val Ile Gly Ser Val Val Met Leu Glu Ile Asp
1 5 10 15

Asn Arg Leu Cys Leu Gln Ser Pro Glu Asn Asp His Cys Phe Pro Asp
20 25 30

Ala Gln Ser Ala Ala Asp Tyr Leu Gly Ala Leu Ala Ser Leu Gly Ser
35 40 45

Leu Asn Ile Pro Tyr Pro Leu Arg Asp Val Arg Gly Glu Pro Leu Glu
50 55 60

Pro Pro Glu Pro Ser
65

<210> SEQ ID NO 23
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN SWAP (FIG 17 D2-SUB5)

<400> SEQUENCE: 23

```
Glu Leu Ala Pro Glu Val Ile Gly Ser Val Val Met Leu Glu Ile Asp
1               5                   10                  15

Asn Arg Leu Cys Leu Gln Ser Pro Glu Asn Asp His Cys Phe Pro Asp
            20                  25                  30

Ala Gln Ser Ala Ala Asp Tyr Leu Gly Ala Leu Ser Ala Val Glu Arg
        35                  40                  45

Leu Asp Phe Pro Tyr Lys Ile Glu Ala Val Gln Ser Glu Thr Val Glu
    50                  55                  60

Pro Pro Ala Pro Ser
65


<210> SEQ ID NO 24
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN AMINO ACID
      SWAP (FIG 17 D2-AA SWAP1)

<400> SEQUENCE: 24

Glu Leu Ala Pro Asp Val Arg Gly Ser Val Val Met Leu Glu Ile Asp
1               5                   10                  15

Asn Arg Leu Cys Leu Gln Ser Pro Glu Asn Asp His Cys Phe Pro Asp
            20                  25                  30

Ala Gln Ser Ala Ala Asp Tyr Leu Gly Ala Leu Ser Ala Val Glu Arg
        35                  40                  45

Leu Asp Phe Pro Tyr Pro Leu Arg Asp Val Arg Gly Glu Pro Leu Glu
    50                  55                  60

Pro Pro Glu Pro Ser
65


<210> SEQ ID NO 25
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN AMINO ACID
      SWAP (FIG 17 D2-AA SWAP2)

<400> SEQUENCE: 25

Glu Leu Ala Pro Glu Val Ile Gly Ser Ile Val Tyr Leu Glu Ile Asp
1               5                   10                  15

Asn Arg Leu Cys Leu Gln Ser Pro Glu Asn Asp His Cys Phe Pro Asp
            20                  25                  30

Ala Gln Ser Ala Ala Asp Tyr Leu Gly Ala Leu Ser Ala Val Glu Arg
        35                  40                  45

Leu Asp Phe Pro Tyr Pro Leu Arg Asp Val Arg Gly Glu Pro Leu Glu
    50                  55                  60

Pro Pro Glu Pro Ser
65


<210> SEQ ID NO 26
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN AMINO ACID
      SWAP (FIG 17 D2-AA SWAP3)

<400> SEQUENCE: 26

Glu Leu Ala Pro Glu Val Ile Gly Ser Val Val Met Leu Glu Ile Asp
```

-continued

```
1               5                   10                  15

Asn Arg Leu Cys Leu Gln Ser Pro Glu Asn Asp His Cys Phe Pro Asp
            20                  25                  30

Ala Gln Ser Ala Ala Asp Tyr Leu Gly Ala Leu Ala Ser Leu Glu Arg
        35                  40                  45

Leu Asp Phe Pro Tyr Pro Leu Arg Asp Val Arg Gly Glu Pro Leu Glu
    50                  55                  60

Pro Pro Glu Pro Ser
65


<210> SEQ ID NO 27
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN AMINO ACID
      SWAP (FIG 17 D2-AA SWAP4)

<400> SEQUENCE: 27

Glu Leu Ala Pro Glu Val Ile Gly Ser Val Val Met Leu Glu Ile Asp
1               5                   10                  15

Asn Arg Leu Cys Leu Gln Ser Pro Glu Asn Asp His Cys Phe Pro Asp
            20                  25                  30

Ala Gln Ser Ala Ala Asp Tyr Leu Gly Ala Leu Ser Ala Val Gly Ser
        35                  40                  45

Leu Asp Phe Pro Tyr Pro Leu Arg Asp Val Arg Gly Glu Pro Leu Glu
    50                  55                  60

Pro Pro Glu Pro Ser
65


<210> SEQ ID NO 28
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN AMINO ACID
      SWAP (FIG 17 D2-AA SWAP5)

<400> SEQUENCE: 28

Glu Leu Ala Pro Glu Val Ile Gly Ser Val Val Met Leu Glu Ile Asp
1               5                   10                  15

Asn Arg Leu Cys Leu Gln Ser Pro Glu Asn Asp His Cys Phe Pro Asp
            20                  25                  30

Ala Gln Ser Ala Ala Asp Tyr Leu Gly Ala Leu Ser Ala Val Glu Arg
        35                  40                  45

Leu Asn Ile Pro Tyr Pro Leu Arg Asp Val Arg Gly Glu Pro Leu Glu
    50                  55                  60

Pro Pro Glu Pro Ser
65


<210> SEQ ID NO 29
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN AMINO ACID
      SWAP (FIG 17 D2-AA SWAP6)

<400> SEQUENCE: 29

Glu Leu Ala Pro Glu Val Ile Gly Ser Val Val Met Leu Glu Ile Asp
1               5                   10                  15
```

-continued

```
Asn Arg Leu Cys Leu Gln Ser Pro Glu Asn Asp His Cys Phe Pro Asp
            20                  25                  30

Ala Gln Ser Ala Ala Asp Tyr Leu Gly Ala Leu Ser Ala Val Glu Arg
        35                  40                  45

Leu Asp Phe Pro Tyr Lys Ile Glu Asp Val Arg Gly Glu Pro Leu Glu
    50                  55                  60

Pro Pro Glu Pro Ser
65


<210> SEQ ID NO 30
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN AMINO ACID
      SWAP (FIG 17 D2-AA SWAP7)

<400> SEQUENCE: 30

Glu Leu Ala Pro Glu Val Ile Gly Ser Val Val Met Leu Glu Ile Asp
1               5                   10                  15

Asn Arg Leu Cys Leu Gln Ser Pro Glu Asn Asp His Cys Phe Pro Asp
            20                  25                  30

Ala Gln Ser Ala Ala Asp Tyr Leu Gly Ala Leu Ser Ala Val Glu Arg
        35                  40                  45

Leu Asp Phe Pro Tyr Pro Leu Arg Ala Val Gln Ser Glu Pro Leu Glu
    50                  55                  60

Pro Pro Glu Pro Ser
65


<210> SEQ ID NO 31
<211> LENGTH: 69
<212> TYPE: PRT
<213> ORGANISM: Artificial sequence
<220> FEATURE:
<223> OTHER INFORMATION: NOTCH 3/ NOTCH 1 DIMERIZATION DOMAIN AMINO ACID
      SWAP (FIG 17 D2-AA SWAP8)

<400> SEQUENCE: 31

Glu Leu Ala Pro Glu Val Ile Gly Ser Val Val Met Leu Glu Ile Asp
1               5                   10                  15

Asn Arg Leu Cys Leu Gln Ser Pro Glu Asn Asp His Cys Phe Pro Asp
            20                  25                  30

Ala Gln Ser Ala Ala Asp Tyr Leu Gly Ala Leu Ser Ala Val Glu Arg
        35                  40                  45

Leu Asp Phe Pro Tyr Pro Leu Arg Asp Val Arg Gly Glu Thr Val Glu
    50                  55                  60

Pro Pro Ala Pro Ser
65


<210> SEQ ID NO 32
<211> LENGTH: 10
<212> TYPE: PRT
<213> ORGANISM: Artificial sequence
<220> FEATURE:
<223> OTHER INFORMATION: CDR-H1 OF MAB 256A-4

<400> SEQUENCE: 32

Gly Phe Thr Phe Ser His Tyr Tyr Met Ser
1               5                   10


<210> SEQ ID NO 33
<211> LENGTH: 12
```

-continued

```
<212> TYPE: PRT
<213> ORGANISM: Artificial sequence
<220> FEATURE:
<223> OTHER INFORMATION: CDR-H2 OF MAB 256A-4

<400> SEQUENCE: 33

Ile Ser Asn Gly Gly Gly Arg Thr Asp Tyr Pro Asp
1               5                   10


<210> SEQ ID NO 34
<211> LENGTH: 13
<212> TYPE: PRT
<213> ORGANISM: Artificial sequence
<220> FEATURE:
<223> OTHER INFORMATION: CDR-H3 OF MAB 256A-4

<400> SEQUENCE: 34

Arg Leu Asp Tyr Phe Gly Gly Ser Pro Tyr Phe Asp Tyr
1               5                   10


<210> SEQ ID NO 35
<211> LENGTH: 10
<212> TYPE: PRT
<213> ORGANISM: Artificial sequence
<220> FEATURE:
<223> OTHER INFORMATION: CDR-L1 OF MAB 256A-4

<400> SEQUENCE: 35

Ser Ala Ser Ser Ser Val Ser Tyr Met His
1               5                   10


<210> SEQ ID NO 36
<211> LENGTH: 7
<212> TYPE: PRT
<213> ORGANISM: Artificial sequence
<220> FEATURE:
<223> OTHER INFORMATION: CDR-L2 OF MAB 256A-4

<400> SEQUENCE: 36

Glu Ile Ser Lys Leu Ala Ser
1               5


<210> SEQ ID NO 37
<211> LENGTH: 9
<212> TYPE: PRT
<213> ORGANISM: Artificial sequence
<220> FEATURE:
<223> OTHER INFORMATION: CDR-L3 OF MAB 256A-4

<400> SEQUENCE: 37

Gln Gln Trp Asn Tyr Pro Leu Ile Thr
1               5


<210> SEQ ID NO 38
<211> LENGTH: 10
<212> TYPE: PRT
<213> ORGANISM: Artificial sequence
<220> FEATURE:
<223> OTHER INFORMATION: CDR-H1 OF MAB 256A-8

<400> SEQUENCE: 38

Gly Phe Thr Phe Ser His Tyr Tyr Met Ser
1               5                   10


<210> SEQ ID NO 39
<211> LENGTH: 12
<212> TYPE: PRT
<213> ORGANISM: Artificial sequence
```

<220> FEATURE:
<223> OTHER INFORMATION: CDR-H2 OF MAB 256A-8

<400> SEQUENCE: 39

Tyr Ile Asn Ser Gly Gly Gly Arg Thr Asp Tyr Pro
1               5                   10

<210> SEQ ID NO 40
<211> LENGTH: 12
<212> TYPE: PRT
<213> ORGANISM: Artificial sequence
<220> FEATURE:
<223> OTHER INFORMATION: CDR-H3 OF MAB 256A-8

<400> SEQUENCE: 40

Leu Asp Tyr Tyr Gly Gly Ser Pro Tyr Phe Asp Tyr
1               5                   10

<210> SEQ ID NO 41
<211> LENGTH: 10
<212> TYPE: PRT
<213> ORGANISM: Artificial sequence
<220> FEATURE:
<223> OTHER INFORMATION: CDR-L1 OF MAB 256A-8

<400> SEQUENCE: 41

Ser Ala Ser Ser Ser Val Ser Tyr Met His
1               5                   10

<210> SEQ ID NO 42
<211> LENGTH: 8
<212> TYPE: PRT
<213> ORGANISM: Artificial sequence
<220> FEATURE:
<223> OTHER INFORMATION: CDR-L2 OF MAB 256A-8

<400> SEQUENCE: 42

Tyr Glu Ile Ser Lys Leu Ala Ser
1               5

<210> SEQ ID NO 43
<211> LENGTH: 9
<212> TYPE: PRT
<213> ORGANISM: Artificial sequence
<220> FEATURE:
<223> OTHER INFORMATION: CDR-L3 OF MAB 256A-8

<400> SEQUENCE: 43

Gln Gln Trp Asn Tyr Pro Leu Ile Thr
1               5

<210> SEQ ID NO 44
<211> LENGTH: 2556
<212> TYPE: PRT
<213> ORGANISM: Homo sapiens
<220> FEATURE:
<223> OTHER INFORMATION: human Notch1

<400> SEQUENCE: 44

Met Pro Pro Leu Leu Ala Pro Leu Leu Cys Leu Ala Leu Leu Pro
1               5                   10                  15

Ala Leu Ala Ala Arg Gly Pro Arg Cys Ser Gln Pro Gly Glu Thr
                20                  25                  30

Cys Leu Asn Gly Gly Lys Cys Glu Ala Ala Asn Gly Thr Glu Ala
                35                  40                  45

Cys Val Cys Gly Gly Ala Phe Val Gly Pro Arg Cys Gln Asp Pro

-continued

```
                50                  55                  60

Asn Pro Cys Leu Ser Thr Pro Cys Lys Asn Ala Gly Thr Cys His
                65                  70                  75

Val Val Asp Arg Arg Gly Val Ala Asp Tyr Ala Cys Ser Cys Ala
                80                  85                  90

Leu Gly Phe Ser Gly Pro Leu Cys Leu Thr Pro Leu Asp Asn Ala
                95                 100                 105

Cys Leu Thr Asn Pro Cys Arg Asn Gly Gly Thr Cys Asp Leu Leu
                110                 115                 120

Thr Leu Thr Glu Tyr Lys Cys Arg Cys Pro Pro Gly Trp Ser Gly
                125                 130                 135

Lys Ser Cys Gln Gln Ala Asp Pro Cys Ala Ser Asn Pro Cys Ala
                140                 145                 150

Asn Gly Gly Gln Cys Leu Pro Phe Glu Ala Ser Tyr Ile Cys His
                155                 160                 165

Cys Pro Pro Ser Phe His Gly Pro Thr Cys Arg Gln Asp Val Asn
                170                 175                 180

Glu Cys Gly Gln Lys Pro Gly Leu Cys Arg His Gly Gly Thr Cys
                185                 190                 195

His Asn Glu Val Gly Ser Tyr Arg Cys Val Cys Arg Ala Thr His
                200                 205                 210

Thr Gly Pro Asn Cys Glu Arg Pro Tyr Val Pro Cys Ser Pro Ser
                215                 220                 225

Pro Cys Gln Asn Gly Gly Thr Cys Arg Pro Thr Gly Asp Val Thr
                230                 235                 240

His Glu Cys Ala Cys Leu Pro Gly Phe Thr Gly Gln Asn Cys Glu
                245                 250                 255

Glu Asn Ile Asp Asp Cys Pro Gly Asn Asn Cys Lys Asn Gly Gly
                260                 265                 270

Ala Cys Val Asp Gly Val Asn Thr Tyr Asn Cys Arg Cys Pro Pro
                275                 280                 285

Glu Trp Thr Gly Gln Tyr Cys Thr Glu Asp Val Asp Glu Cys Gln
                290                 295                 300

Leu Met Pro Asn Ala Cys Gln Asn Gly Gly Thr Cys His Asn Thr
                305                 310                 315

His Gly Gly Tyr Asn Cys Val Cys Val Asn Gly Trp Thr Gly Glu
                320                 325                 330

Asp Cys Ser Glu Asn Ile Asp Asp Cys Ala Ser Ala Ala Cys Phe
                335                 340                 345

His Gly Ala Thr Cys His Asp Arg Val Ala Ser Phe Tyr Cys Glu
                350                 355                 360

Cys Pro His Gly Arg Thr Gly Leu Leu Cys His Leu Asn Asp Ala
                365                 370                 375

Cys Ile Ser Asn Pro Cys Asn Glu Gly Ser Asn Cys Asp Thr Asn
                380                 385                 390

Pro Val Asn Gly Lys Ala Ile Cys Thr Cys Pro Ser Gly Tyr Thr
                395                 400                 405

Gly Pro Ala Cys Ser Gln Asp Val Asp Glu Cys Ser Leu Gly Ala
                410                 415                 420

Asn Pro Cys Glu His Ala Gly Lys Cys Ile Asn Thr Leu Gly Ser
                425                 430                 435

Phe Glu Cys Gln Cys Leu Gln Gly Tyr Thr Gly Pro Arg Cys Glu
                440                 445                 450
```

-continued

```
Ile Asp Val Asn Glu Cys Val Ser Asn Pro Cys Gln Asn Asp Ala
                455                 460                 465

Thr Cys Leu Asp Gln Ile Gly Glu Phe Gln Cys Ile Cys Met Pro
                470                 475                 480

Gly Tyr Glu Gly Val His Cys Glu Val Asn Thr Asp Glu Cys Ala
                485                 490                 495

Ser Ser Pro Cys Leu His Asn Gly Arg Cys Leu Asp Lys Ile Asn
                500                 505                 510

Glu Phe Gln Cys Glu Cys Pro Thr Gly Phe Thr Gly His Leu Cys
                515                 520                 525

Gln Tyr Asp Val Asp Glu Cys Ala Ser Thr Pro Cys Lys Asn Gly
                530                 535                 540

Ala Lys Cys Leu Asp Gly Pro Asn Thr Tyr Thr Cys Val Cys Thr
                545                 550                 555

Glu Gly Tyr Thr Gly Thr His Cys Glu Val Asp Ile Asp Glu Cys
                560                 565                 570

Asp Pro Asp Pro Cys His Tyr Gly Ser Cys Lys Asp Gly Val Ala
                575                 580                 585

Thr Phe Thr Cys Leu Cys Arg Pro Gly Tyr Thr Gly His His Cys
                590                 595                 600

Glu Thr Asn Ile Asn Glu Cys Ser Ser Gln Pro Cys Arg His Gly
                605                 610                 615

Gly Thr Cys Gln Asp Arg Asp Asn Ala Tyr Leu Cys Phe Cys Leu
                620                 625                 630

Lys Gly Thr Thr Gly Pro Asn Cys Glu Ile Asn Leu Asp Asp Cys
                635                 640                 645

Ala Ser Ser Pro Cys Asp Ser Gly Thr Cys Leu Asp Lys Ile Asp
                650                 655                 660

Gly Tyr Glu Cys Ala Cys Glu Pro Gly Tyr Thr Gly Ser Met Cys
                665                 670                 675

Asn Ile Asn Ile Asp Glu Cys Ala Gly Asn Pro Cys His Asn Gly
                680                 685                 690

Gly Thr Cys Glu Asp Gly Ile Asn Gly Phe Thr Cys Arg Cys Pro
                695                 700                 705

Glu Gly Tyr His Asp Pro Thr Cys Leu Ser Glu Val Asn Glu Cys
                710                 715                 720

Asn Ser Asn Pro Cys Val His Gly Ala Cys Arg Asp Ser Leu Asn
                725                 730                 735

Gly Tyr Lys Cys Asp Cys Asp Pro Gly Trp Ser Gly Thr Asn Cys
                740                 745                 750

Asp Ile Asn Asn Asn Glu Cys Glu Ser Asn Pro Cys Val Asn Gly
                755                 760                 765

Gly Thr Cys Lys Asp Met Thr Ser Gly Tyr Val Cys Thr Cys Arg
                770                 775                 780

Glu Gly Phe Ser Gly Pro Asn Cys Gln Thr Asn Ile Asn Glu Cys
                785                 790                 795

Ala Ser Asn Pro Cys Leu Asn Gln Gly Thr Cys Ile Asp Asp Val
                800                 805                 810

Ala Gly Tyr Lys Cys Asn Cys Leu Leu Pro Tyr Thr Gly Ala Thr
                815                 820                 825

Cys Glu Val Val Leu Ala Pro Cys Ala Pro Ser Pro Cys Arg Asn
                830                 835                 840

Gly Gly Glu Cys Arg Gln Ser Glu Asp Tyr Glu Ser Phe Ser Cys
                845                 850                 855
```

```
Val Cys Pro Thr Gly Trp Gln Ala Gly Gln Thr Cys Glu Val Asp
            860                 865                 870

Ile Asn Glu Cys Val Leu Ser Pro Cys Arg His Gly Ala Ser Cys
            875                 880                 885

Gln Asn Thr His Gly Gly Tyr Arg Cys His Cys Gln Ala Gly Tyr
            890                 895                 900

Ser Gly Arg Asn Cys Glu Thr Asp Ile Asp Asp Cys Arg Pro Asn
            905                 910                 915

Pro Cys His Asn Gly Gly Ser Cys Thr Asp Gly Ile Asn Thr Ala
            920                 925                 930

Phe Cys Asp Cys Leu Pro Gly Phe Arg Gly Thr Phe Cys Glu Glu
            935                 940                 945

Asp Ile Asn Glu Cys Ala Ser Asp Pro Cys Arg Asn Gly Ala Asn
            950                 955                 960

Cys Thr Asp Cys Val Asp Ser Tyr Thr Cys Thr Cys Pro Ala Gly
            965                 970                 975

Phe Ser Gly Ile His Cys Glu Asn Asn Thr Pro Asp Cys Thr Glu
            980                 985                 990

Ser Ser Cys Phe Asn Gly Gly Thr Cys Val Asp Gly Ile Asn Ser
            995                1000                1005

Phe Thr Cys Leu Cys Pro Pro Gly Phe Thr Gly Ser Tyr Cys Gln
           1010                1015                1020

His Asp Val Asn Glu Cys Asp Ser Gln Pro Cys Leu His Gly Gly
           1025                1030                1035

Thr Cys Gln Asp Gly Cys Gly Ser Tyr Arg Cys Thr Cys Pro Gln
           1040                1045                1050

Gly Tyr Thr Gly Pro Asn Cys Gln Asn Leu Val His Trp Cys Asp
           1055                1060                1065

Ser Ser Pro Cys Lys Asn Gly Gly Lys Cys Trp Gln Thr His Thr
           1070                1075                1080

Gln Tyr Arg Cys Glu Cys Pro Ser Gly Trp Thr Gly Leu Tyr Cys
           1085                1090                1095

Asp Val Pro Ser Val Ser Cys Glu Val Ala Ala Gln Arg Gln Gly
           1100                1105                1110

Val Asp Val Ala Arg Leu Cys Gln His Gly Gly Leu Cys Val Asp
           1115                1120                1125

Ala Gly Asn Thr His His Cys Arg Cys Gln Ala Gly Tyr Thr Gly
           1130                1135                1140

Ser Tyr Cys Glu Asp Leu Val Asp Glu Cys Ser Pro Ser Pro Cys
           1145                1150                1155

Gln Asn Gly Ala Thr Cys Thr Asp Tyr Leu Gly Gly Tyr Ser Cys
           1160                1165                1170

Lys Cys Val Ala Gly Tyr His Gly Val Asn Cys Ser Glu Glu Ile
           1175                1180                1185

Asp Glu Cys Leu Ser His Pro Cys Gln Asn Gly Gly Thr Cys Leu
           1190                1195                1200

Asp Leu Pro Asn Thr Tyr Lys Cys Ser Cys Pro Arg Gly Thr Gln
           1205                1210                1215

Gly Val His Cys Glu Ile Asn Val Asp Asp Cys Asn Pro Pro Val
           1220                1225                1230

Asp Pro Val Ser Arg Ser Pro Lys Cys Phe Asn Asn Gly Thr Cys
           1235                1240                1245

Val Asp Gln Val Gly Gly Tyr Ser Cys Thr Cys Pro Pro Gly Phe
```

-continued

```
            1250                1255                1260

Val Gly Glu Arg Cys Glu Gly Asp Val Asn Glu Cys Leu Ser Asn
            1265                1270                1275

Pro Cys Asp Ala Arg Gly Thr Gln Asn Cys Val Gln Arg Val Asn
            1280                1285                1290

Asp Phe His Cys Glu Cys Arg Ala Gly His Thr Gly Arg Arg Cys
            1295                1300                1305

Glu Ser Val Ile Asn Gly Cys Lys Gly Lys Pro Cys Lys Asn Gly
            1310                1315                1320

Gly Thr Cys Ala Val Ala Ser Asn Thr Ala Arg Gly Phe Ile Cys
            1325                1330                1335

Lys Cys Pro Ala Gly Phe Glu Gly Ala Thr Cys Glu Asn Asp Ala
            1340                1345                1350

Arg Thr Cys Gly Ser Leu Arg Cys Leu Asn Gly Gly Thr Cys Ile
            1355                1360                1365

Ser Gly Pro Arg Ser Pro Thr Cys Leu Cys Leu Gly Pro Phe Thr
            1370                1375                1380

Gly Pro Glu Cys Gln Phe Pro Ala Ser Ser Pro Cys Leu Gly Gly
            1385                1390                1395

Asn Pro Cys Tyr Asn Gln Gly Thr Cys Glu Pro Thr Ser Glu Ser
            1400                1405                1410

Pro Phe Tyr Arg Cys Leu Cys Pro Ala Lys Phe Asn Gly Leu Leu
            1415                1420                1425

Cys His Ile Leu Asp Tyr Ser Phe Gly Gly Gly Ala Gly Arg Asp
            1430                1435                1440

Ile Pro Pro Pro Leu Ile Glu Glu Ala Cys Glu Leu Pro Glu Cys
            1445                1450                1455

Gln Glu Asp Ala Gly Asn Lys Val Cys Ser Leu Gln Cys Asn Asn
            1460                1465                1470

His Ala Cys Gly Trp Asp Gly Gly Asp Cys Ser Leu Asn Phe Asn
            1475                1480                1485

Asp Pro Trp Lys Asn Cys Thr Gln Ser Leu Gln Cys Trp Lys Tyr
            1490                1495                1500

Phe Ser Asp Gly His Cys Asp Ser Gln Cys Asn Ser Ala Gly Cys
            1505                1510                1515

Leu Phe Asp Gly Phe Asp Cys Gln Arg Ala Glu Gly Gln Cys Asn
            1520                1525                1530

Pro Leu Tyr Asp Gln Tyr Cys Lys Asp His Phe Ser Asp Gly His
            1535                1540                1545

Cys Asp Gln Gly Cys Asn Ser Ala Glu Cys Glu Trp Asp Gly Leu
            1550                1555                1560

Asp Cys Ala Glu His Val Pro Glu Arg Leu Ala Ala Gly Thr Leu
            1565                1570                1575

Val Val Val Val Leu Met Pro Pro Glu Gln Leu Arg Asn Ser Ser
            1580                1585                1590

Phe His Phe Leu Arg Glu Leu Ser Arg Val Leu His Thr Asn Val
            1595                1600                1605

Val Phe Lys Arg Asp Ala His Gly Gln Gln Met Ile Phe Pro Tyr
            1610                1615                1620

Tyr Gly Arg Glu Glu Glu Leu Arg Lys His Pro Ile Lys Arg Ala
            1625                1630                1635

Ala Glu Gly Trp Ala Ala Pro Asp Ala Leu Leu Gly Gln Val Lys
            1640                1645                1650
```

-continued

```
Ala Ser Leu Leu Pro Gly Gly Ser Glu Gly Gly Arg Arg Arg Arg
                1655                1660                1665

Glu Leu Asp Pro Met Asp Val Arg Gly Ser Ile Val Tyr Leu Glu
                1670                1675                1680

Ile Asp Asn Arg Gln Cys Val Gln Ala Ser Ser Gln Cys Phe Gln
                1685                1690                1695

Ser Ala Thr Asp Val Ala Ala Phe Leu Gly Ala Leu Ala Ser Leu
                1700                1705                1710

Gly Ser Leu Asn Ile Pro Tyr Lys Ile Glu Ala Val Gln Ser Glu
                1715                1720                1725

Thr Val Glu Pro Pro Pro Pro Ala Gln Leu His Phe Met Tyr Val
                1730                1735                1740

Ala Ala Ala Ala Phe Val Leu Leu Phe Phe Val Gly Cys Gly Val
                1745                1750                1755

Leu Leu Ser Arg Lys Arg Arg Arg Gln His Gly Gln Leu Trp Phe
                1760                1765                1770

Pro Glu Gly Phe Lys Val Ser Glu Ala Ser Lys Lys Lys Arg Arg
                1775                1780                1785

Glu Pro Leu Gly Glu Asp Ser Val Gly Leu Lys Pro Leu Lys Asn
                1790                1795                1800

Ala Ser Asp Gly Ala Leu Met Asp Asp Asn Gln Asn Glu Trp Gly
                1805                1810                1815

Asp Glu Asp Leu Glu Thr Lys Lys Phe Arg Phe Glu Glu Pro Val
                1820                1825                1830

Val Leu Pro Asp Leu Asp Asp Gln Thr Asp His Arg Gln Trp Thr
                1835                1840                1845

Gln Gln His Leu Asp Ala Ala Asp Leu Arg Met Ser Ala Met Ala
                1850                1855                1860

Pro Thr Pro Pro Gln Gly Glu Val Asp Ala Asp Cys Met Asp Val
                1865                1870                1875

Asn Val Arg Gly Pro Asp Gly Phe Thr Pro Leu Met Ile Ala Ser
                1880                1885                1890

Cys Ser Gly Gly Gly Leu Glu Thr Gly Asn Ser Glu Glu Glu Glu
                1895                1900                1905

Asp Ala Pro Ala Val Ile Ser Asp Phe Ile Tyr Gln Gly Ala Ser
                1910                1915                1920

Leu His Asn Gln Thr Asp Arg Thr Gly Glu Thr Ala Leu His Leu
                1925                1930                1935

Ala Ala Arg Tyr Ser Arg Ser Asp Ala Ala Lys Arg Leu Leu Glu
                1940                1945                1950

Ala Ser Ala Asp Ala Asn Ile Gln Asp Asn Met Gly Arg Thr Pro
                1955                1960                1965

Leu His Ala Ala Val Ser Ala Asp Ala Gln Gly Val Phe Gln Ile
                1970                1975                1980

Leu Ile Arg Asn Arg Ala Thr Asp Leu Asp Ala Arg Met His Asp
                1985                1990                1995

Gly Thr Thr Pro Leu Ile Leu Ala Ala Arg Leu Ala Val Glu Gly
                2000                2005                2010

Met Leu Glu Asp Leu Ile Asn Ser His Ala Asp Val Asn Ala Val
                2015                2020                2025

Asp Asp Leu Gly Lys Ser Ala Leu His Trp Ala Ala Ala Val Asn
                2030                2035                2040

Asn Val Asp Ala Ala Val Val Leu Leu Lys Asn Gly Ala Asn Lys
                2045                2050                2055
```

-continued

```
Asp Met Gln Asn Asn Arg Glu Glu Thr Pro Leu Phe Leu Ala Ala
                2060                2065                2070

Arg Glu Gly Ser Tyr Glu Thr Ala Lys Val Leu Leu Asp His Phe
                2075                2080                2085

Ala Asn Arg Asp Ile Thr Asp His Met Asp Arg Leu Pro Arg Asp
                2090                2095                2100

Ile Ala Gln Glu Arg Met His His Asp Ile Val Arg Leu Leu Asp
                2105                2110                2115

Glu Tyr Asn Leu Val Arg Ser Pro Gln Leu His Gly Ala Pro Leu
                2120                2125                2130

Gly Gly Thr Pro Thr Leu Ser Pro Pro Leu Cys Ser Pro Asn Gly
                2135                2140                2145

Tyr Leu Gly Ser Leu Lys Pro Gly Val Gln Gly Lys Lys Val Arg
                2150                2155                2160

Lys Pro Ser Ser Lys Gly Leu Ala Cys Gly Ser Lys Glu Ala Lys
                2165                2170                2175

Asp Leu Lys Ala Arg Arg Lys Lys Ser Gln Asp Gly Lys Gly Cys
                2180                2185                2190

Leu Leu Asp Ser Ser Gly Met Leu Ser Pro Val Asp Ser Leu Glu
                2195                2200                2205

Ser Pro His Gly Tyr Leu Ser Asp Val Ala Ser Pro Pro Leu Leu
                2210                2215                2220

Pro Ser Pro Phe Gln Gln Ser Pro Ser Val Pro Leu Asn His Leu
                2225                2230                2235

Pro Gly Met Pro Asp Thr His Leu Gly Ile Gly His Leu Asn Val
                2240                2245                2250

Ala Ala Lys Pro Glu Met Ala Ala Leu Gly Gly Gly Gly Arg Leu
                2255                2260                2265

Ala Phe Glu Thr Gly Pro Pro Arg Leu Ser His Leu Pro Val Ala
                2270                2275                2280

Ser Gly Thr Ser Thr Val Leu Gly Ser Ser Ser Gly Gly Ala Leu
                2285                2290                2295

Asn Phe Thr Val Gly Gly Ser Thr Ser Leu Asn Gly Gln Cys Glu
                2300                2305                2310

Trp Leu Ser Arg Leu Gln Ser Gly Met Val Pro Asn Gln Tyr Asn
                2315                2320                2325

Pro Leu Arg Gly Ser Val Ala Pro Gly Pro Leu Ser Thr Gln Ala
                2330                2335                2340

Pro Ser Leu Gln His Gly Met Val Gly Pro Leu His Ser Ser Leu
                2345                2350                2355

Ala Ala Ser Ala Leu Ser Gln Met Met Ser Tyr Gln Gly Leu Pro
                2360                2365                2370

Ser Thr Arg Leu Ala Thr Gln Pro His Leu Val Gln Thr Gln Gln
                2375                2380                2385

Val Gln Pro Gln Asn Leu Gln Met Gln Gln Gln Asn Leu Gln Pro
                2390                2395                2400

Ala Asn Ile Gln Gln Gln Gln Ser Leu Gln Pro Pro Pro Pro Pro
                2405                2410                2415

Pro Gln Pro His Leu Gly Val Ser Ser Ala Ala Ser Gly His Leu
                2420                2425                2430

Gly Arg Ser Phe Leu Ser Gly Glu Pro Ser Gln Ala Asp Val Gln
                2435                2440                2445

Pro Leu Gly Pro Ser Ser Leu Ala Val His Thr Ile Leu Pro Gln
```

```
              2450                2455                2460

Glu Ser Pro Ala Leu Pro Thr Ser Leu Pro Ser Ser Leu Val Pro
              2465                2470                2475

Pro Val Thr Ala Ala Gln Phe Leu Thr Pro Pro Ser Gln His Ser
              2480                2485                2490

Tyr Ser Ser Pro Val Asp Asn Thr Pro Ser His Gln Leu Gln Val
              2495                2500                2505

Pro Glu His Pro Phe Leu Thr Pro Ser Pro Glu Ser Pro Asp Gln
              2510                2515                2520

Trp Ser Ser Ser Ser Pro His Ser Asn Val Ser Asp Trp Ser Glu
              2525                2530                2535

Gly Val Ser Ser Pro Pro Thr Ser Met Gln Ser Gln Ile Ala Arg
              2540                2545                2550

Ile Pro Glu Ala Phe Lys
              2555


<210> SEQ ID NO 45
<211> LENGTH: 2471
<212> TYPE: PRT
<213> ORGANISM: Homo sapiens
<220> FEATURE:
<223> OTHER INFORMATION: human Notch2

<400> SEQUENCE: 45

Met Pro Ala Leu Arg Pro Ala Leu Leu Trp Ala Leu Leu Ala Leu
1               5                   10                  15

Trp Leu Cys Cys Ala Ala Pro Ala His Ala Leu Gln Cys Arg Asp
                20                  25                  30

Gly Tyr Glu Pro Cys Val Asn Glu Gly Met Cys Val Thr Tyr His
                35                  40                  45

Asn Gly Thr Gly Tyr Cys Lys Cys Pro Glu Gly Phe Leu Gly Glu
                50                  55                  60

Tyr Cys Gln His Arg Asp Pro Cys Glu Lys Asn Arg Cys Gln Asn
                65                  70                  75

Gly Gly Thr Cys Val Ala Gln Ala Met Leu Gly Lys Ala Thr Cys
                80                  85                  90

Arg Cys Ala Ser Gly Phe Thr Gly Glu Asp Cys Gln Tyr Ser Thr
                95                  100                 105

Ser His Pro Cys Phe Val Ser Arg Pro Cys Leu Asn Gly Gly Thr
                110                 115                 120

Cys His Met Leu Ser Arg Asp Thr Tyr Glu Cys Thr Cys Gln Val
                125                 130                 135

Gly Phe Thr Gly Lys Glu Cys Gln Trp Thr Asp Ala Cys Leu Ser
                140                 145                 150

His Pro Cys Ala Asn Gly Ser Thr Cys Thr Thr Val Ala Asn Gln
                155                 160                 165

Phe Ser Cys Lys Cys Leu Thr Gly Phe Thr Gly Gln Lys Cys Glu
                170                 175                 180

Thr Asp Val Asn Glu Cys Asp Ile Pro Gly His Cys Gln His Gly
                185                 190                 195

Gly Thr Cys Leu Asn Leu Pro Gly Ser Tyr Gln Cys Gln Cys Pro
                200                 205                 210

Gln Gly Phe Thr Gly Gln Tyr Cys Asp Ser Leu Tyr Val Pro Cys
                215                 220                 225

Ala Pro Ser Pro Cys Val Asn Gly Gly Thr Cys Arg Gln Thr Gly
                230                 235                 240
```

-continued

```
Asp Phe Thr Phe Glu Cys Asn Cys Leu Pro Gly Phe Glu Gly Ser
                245                 250                 255

Thr Cys Glu Arg Asn Ile Asp Asp Cys Pro Asn His Arg Cys Gln
                260                 265                 270

Asn Gly Gly Val Cys Val Asp Gly Val Asn Thr Tyr Asn Cys Arg
                275                 280                 285

Cys Pro Pro Gln Trp Thr Gly Gln Phe Cys Thr Glu Asp Val Asp
                290                 295                 300

Glu Cys Leu Leu Gln Pro Asn Ala Cys Gln Asn Gly Gly Thr Cys
                305                 310                 315

Ala Asn Arg Asn Gly Gly Tyr Gly Cys Val Cys Val Asn Gly Trp
                320                 325                 330

Ser Gly Asp Asp Cys Ser Glu Asn Ile Asp Asp Cys Ala Phe Ala
                335                 340                 345

Ser Cys Thr Pro Gly Ser Thr Cys Ile Asp Arg Val Ala Ser Phe
                350                 355                 360

Ser Cys Met Cys Pro Glu Gly Lys Ala Gly Leu Leu Cys His Leu
                365                 370                 375

Asp Asp Ala Cys Ile Ser Asn Pro Cys His Lys Gly Ala Leu Cys
                380                 385                 390

Asp Thr Asn Pro Leu Asn Gly Gln Tyr Ile Cys Thr Cys Pro Gln
                395                 400                 405

Gly Tyr Lys Gly Ala Asp Cys Thr Glu Asp Val Asp Glu Cys Ala
                410                 415                 420

Met Ala Asn Ser Asn Pro Cys Glu His Ala Gly Lys Cys Val Asn
                425                 430                 435

Thr Asp Gly Ala Phe His Cys Glu Cys Leu Lys Gly Tyr Ala Gly
                440                 445                 450

Pro Arg Cys Glu Met Asp Ile Asn Glu Cys His Ser Asp Pro Cys
                455                 460                 465

Gln Asn Asp Ala Thr Cys Leu Asp Lys Ile Gly Gly Phe Thr Cys
                470                 475                 480

Leu Cys Met Pro Gly Phe Lys Gly Val His Cys Glu Leu Glu Ile
                485                 490                 495

Asn Glu Cys Gln Ser Asn Pro Cys Val Asn Asn Gly Gln Cys Val
                500                 505                 510

Asp Lys Val Asn Arg Phe Gln Cys Leu Cys Pro Pro Gly Phe Thr
                515                 520                 525

Gly Pro Val Cys Gln Ile Asp Ile Asp Asp Cys Ser Ser Thr Pro
                530                 535                 540

Cys Leu Asn Gly Ala Lys Cys Ile Asp His Pro Asn Gly Tyr Glu
                545                 550                 555

Cys Gln Cys Ala Thr Gly Phe Thr Gly Val Leu Cys Glu Glu Asn
                560                 565                 570

Ile Asp Asn Cys Asp Pro Asp Pro Cys His His Gly Gln Cys Gln
                575                 580                 585

Asp Gly Ile Asp Ser Tyr Thr Cys Ile Cys Asn Pro Gly Tyr Met
                590                 595                 600

Gly Ala Ile Cys Ser Asp Gln Ile Asp Glu Cys Tyr Ser Ser Pro
                605                 610                 615

Cys Leu Asn Asp Gly Arg Cys Ile Asp Leu Val Asn Gly Tyr Gln
                620                 625                 630

Cys Asn Cys Gln Pro Gly Thr Ser Gly Val Asn Cys Glu Ile Asn
```

-continued

```
                635                 640                 645

Phe Asp Asp Cys Ala Ser Asn Pro Cys Ile His Gly Ile Cys Met
                650                 655                 660

Asp Gly Ile Asn Arg Tyr Ser Cys Val Cys Ser Pro Gly Phe Thr
                665                 670                 675

Gly Gln Arg Cys Asn Ile Asp Ile Asp Glu Cys Ala Ser Asn Pro
                680                 685                 690

Cys Arg Lys Gly Ala Thr Cys Ile Asn Gly Val Asn Gly Phe Arg
                695                 700                 705

Cys Ile Cys Pro Glu Gly Pro His His Pro Ser Cys Tyr Ser Gln
                710                 715                 720

Val Asn Glu Cys Leu Ser Asn Pro Cys Ile His Gly Asn Cys Thr
                725                 730                 735

Gly Gly Leu Ser Gly Tyr Lys Cys Leu Cys Asp Ala Gly Trp Val
                740                 745                 750

Gly Ile Asn Cys Glu Val Asp Lys Asn Glu Cys Leu Ser Asn Pro
                755                 760                 765

Cys Gln Asn Gly Gly Thr Cys Asp Asn Leu Val Asn Gly Tyr Arg
                770                 775                 780

Cys Thr Cys Lys Lys Gly Phe Lys Gly Tyr Asn Cys Gln Val Asn
                785                 790                 795

Ile Asp Glu Cys Ala Ser Asn Pro Cys Leu Asn Gln Gly Thr Cys
                800                 805                 810

Phe Asp Asp Ile Ser Gly Tyr Thr Cys His Cys Val Leu Pro Tyr
                815                 820                 825

Thr Gly Lys Asn Cys Gln Thr Val Leu Ala Pro Cys Ser Pro Asn
                830                 835                 840

Pro Cys Glu Asn Ala Ala Val Cys Lys Glu Ser Pro Asn Phe Glu
                845                 850                 855

Ser Tyr Thr Cys Leu Cys Ala Pro Gly Trp Gln Gly Gln Arg Cys
                860                 865                 870

Thr Ile Asp Ile Asp Glu Cys Ile Ser Lys Pro Cys Met Asn His
                875                 880                 885

Gly Leu Cys His Asn Thr Gln Gly Ser Tyr Met Cys Glu Cys Pro
                890                 895                 900

Pro Gly Phe Ser Gly Met Asp Cys Glu Glu Asp Ile Asp Asp Cys
                905                 910                 915

Leu Ala Asn Pro Cys Gln Asn Gly Gly Ser Cys Met Asp Gly Val
                920                 925                 930

Asn Thr Phe Ser Cys Leu Cys Leu Pro Gly Phe Thr Gly Asp Lys
                935                 940                 945

Cys Gln Thr Asp Met Asn Glu Cys Leu Ser Glu Pro Cys Lys Asn
                950                 955                 960

Gly Gly Thr Cys Ser Asp Tyr Val Asn Ser Tyr Thr Cys Lys Cys
                965                 970                 975

Gln Ala Gly Phe Asp Gly Val His Cys Glu Asn Asn Ile Asn Glu
                980                 985                 990

Cys Thr Glu Ser Ser Cys Phe Asn Gly Gly Thr Cys Val Asp Gly
                995                1000                1005

Ile Asn Ser Phe Ser Cys Leu Cys Pro Val Gly Phe Thr Gly Ser
               1010                1015                1020

Phe Cys Leu His Glu Ile Asn Glu Cys Ser Ser His Pro Cys Leu
               1025                1030                1035
```

-continued

```
Asn Glu Gly Thr Cys Val Asp Gly Leu Gly Thr Tyr Arg Cys Ser
                1040                1045                1050

Cys Pro Leu Gly Tyr Thr Gly Lys Asn Cys Gln Thr Leu Val Asn
                1055                1060                1065

Leu Cys Ser Arg Ser Pro Cys Lys Asn Lys Gly Thr Cys Val Gln
                1070                1075                1080

Lys Lys Ala Glu Ser Gln Cys Leu Cys Pro Ser Gly Trp Ala Gly
                1085                1090                1095

Ala Tyr Cys Asp Val Pro Asn Val Ser Cys Asp Ile Ala Ala Ser
                1100                1105                1110

Arg Arg Gly Val Leu Val Glu His Leu Cys Gln His Ser Gly Val
                1115                1120                1125

Cys Ile Asn Ala Gly Asn Thr His Tyr Cys Gln Cys Pro Leu Gly
                1130                1135                1140

Tyr Thr Gly Ser Tyr Cys Glu Glu Gln Leu Asp Glu Cys Ala Ser
                1145                1150                1155

Asn Pro Cys Gln His Gly Ala Thr Cys Ser Asp Phe Ile Gly Gly
                1160                1165                1170

Tyr Arg Cys Glu Cys Val Pro Gly Tyr Gln Gly Val Asn Cys Glu
                1175                1180                1185

Tyr Glu Val Asp Glu Cys Gln Asn Gln Pro Cys Gln Asn Gly Gly
                1190                1195                1200

Thr Cys Ile Asp Leu Val Asn His Phe Lys Cys Ser Cys Pro Pro
                1205                1210                1215

Gly Thr Arg Gly Leu Leu Cys Glu Glu Asn Ile Asp Asp Cys Ala
                1220                1225                1230

Arg Gly Pro His Cys Leu Asn Gly Gly Gln Cys Met Asp Arg Ile
                1235                1240                1245

Gly Gly Tyr Ser Cys Arg Cys Leu Pro Gly Phe Ala Gly Glu Arg
                1250                1255                1260

Cys Glu Gly Asp Ile Asn Glu Cys Leu Ser Asn Pro Cys Ser Ser
                1265                1270                1275

Glu Gly Ser Leu Asp Cys Ile Gln Leu Thr Asn Asp Tyr Leu Cys
                1280                1285                1290

Val Cys Arg Ser Ala Phe Thr Gly Arg His Cys Glu Thr Phe Val
                1295                1300                1305

Asp Val Cys Pro Gln Met Pro Cys Leu Asn Gly Gly Thr Cys Ala
                1310                1315                1320

Val Ala Ser Asn Met Pro Asp Gly Phe Ile Cys Arg Cys Pro Pro
                1325                1330                1335

Gly Phe Ser Gly Ala Arg Cys Gln Ser Ser Cys Gly Gln Val Lys
                1340                1345                1350

Cys Arg Lys Gly Glu Gln Cys Val His Thr Ala Ser Gly Pro Arg
                1355                1360                1365

Cys Phe Cys Pro Ser Pro Arg Asp Cys Glu Ser Gly Cys Ala Ser
                1370                1375                1380

Ser Pro Cys Gln His Gly Gly Ser Cys His Pro Gln Arg Gln Pro
                1385                1390                1395

Pro Tyr Tyr Ser Cys Gln Cys Ala Pro Pro Phe Ser Gly Ser Arg
                1400                1405                1410

Cys Glu Leu Tyr Thr Ala Pro Pro Ser Thr Pro Pro Ala Thr Cys
                1415                1420                1425

Leu Ser Gln Tyr Cys Ala Asp Lys Ala Arg Asp Gly Val Cys Asp
                1430                1435                1440
```

```
Glu Ala Cys Asn Ser His Ala Cys Gln Trp Asp Gly Gly Asp Cys
                1445                1450                1455

Ser Leu Thr Met Glu Asn Pro Trp Ala Asn Cys Ser Ser Pro Leu
                1460                1465                1470

Pro Cys Trp Asp Tyr Ile Asn Asn Gln Cys Asp Glu Leu Cys Asn
                1475                1480                1485

Thr Val Glu Cys Leu Phe Asp Asn Phe Glu Cys Gln Gly Asn Ser
                1490                1495                1500

Lys Thr Cys Lys Tyr Asp Lys Tyr Cys Ala Asp His Phe Lys Asp
                1505                1510                1515

Asn His Cys Asp Gln Gly Cys Asn Ser Glu Glu Cys Gly Trp Asp
                1520                1525                1530

Gly Leu Asp Cys Ala Ala Asp Gln Pro Glu Asn Leu Ala Glu Gly
                1535                1540                1545

Thr Leu Val Ile Val Val Leu Met Pro Pro Glu Gln Leu Leu Gln
                1550                1555                1560

Asp Ala Arg Ser Phe Leu Arg Ala Leu Gly Thr Leu Leu His Thr
                1565                1570                1575

Asn Leu Arg Ile Lys Arg Asp Ser Gln Gly Glu Leu Met Val Tyr
                1580                1585                1590

Pro Tyr Tyr Gly Glu Lys Ser Ala Ala Met Lys Lys Gln Arg Met
                1595                1600                1605

Thr Arg Arg Ser Leu Pro Gly Glu Gln Glu Gln Glu Val Ala Gly
                1610                1615                1620

Ser Lys Val Phe Leu Glu Ile Asp Asn Arg Gln Cys Val Gln Asp
                1625                1630                1635

Ser Asp His Cys Phe Lys Asn Thr Asp Ala Ala Ala Ala Leu Leu
                1640                1645                1650

Ala Ser His Ala Ile Gln Gly Thr Leu Ser Tyr Pro Leu Val Ser
                1655                1660                1665

Val Val Ser Glu Ser Leu Thr Pro Glu Arg Thr Gln Leu Leu Tyr
                1670                1675                1680

Leu Leu Ala Val Ala Val Val Ile Ile Leu Phe Ile Ile Leu Leu
                1685                1690                1695

Gly Val Ile Met Ala Lys Arg Lys Arg Lys His Gly Ser Leu Trp
                1700                1705                1710

Leu Pro Glu Gly Phe Thr Leu Arg Arg Asp Ala Ser Asn His Lys
                1715                1720                1725

Arg Arg Glu Pro Val Gly Gln Asp Ala Val Gly Leu Lys Asn Leu
                1730                1735                1740

Ser Val Gln Val Ser Glu Ala Asn Leu Ile Gly Thr Gly Thr Ser
                1745                1750                1755

Glu His Trp Val Asp Asp Glu Gly Pro Gln Pro Lys Lys Val Lys
                1760                1765                1770

Ala Glu Asp Glu Ala Leu Leu Ser Glu Glu Asp Asp Pro Ile Asp
                1775                1780                1785

Arg Arg Pro Trp Thr Gln Gln His Leu Glu Ala Ala Asp Ile Arg
                1790                1795                1800

Arg Thr Pro Ser Leu Ala Leu Thr Pro Pro Gln Ala Glu Gln Glu
                1805                1810                1815

Val Asp Val Leu Asp Val Asn Val Arg Gly Pro Asp Gly Cys Thr
                1820                1825                1830

Pro Leu Met Leu Ala Ser Leu Arg Gly Gly Ser Ser Asp Leu Ser
```

-continued 1835 1840 1845

Asp Glu Asp Glu Asp Ala Glu Asp Ser Ser Ala Asn Ile Ile Thr
1850 1855 1860

Asp Leu Val Tyr Gln Gly Ala Ser Leu Gln Ala Gln Thr Asp Arg
1865 1870 1875

Thr Gly Glu Met Ala Leu His Leu Ala Ala Arg Tyr Ser Arg Ala
1880 1885 1890

Asp Ala Ala Lys Arg Leu Leu Asp Ala Gly Ala Asp Ala Asn Ala
1895 1900 1905

Gln Asp Asn Met Gly Arg Cys Pro Leu His Ala Ala Val Ala Ala
1910 1915 1920

Asp Ala Gln Gly Val Phe Gln Ile Leu Ile Arg Asn Arg Val Thr
1925 1930 1935

Asp Leu Asp Ala Arg Met Asn Asp Gly Thr Thr Pro Leu Ile Leu
1940 1945 1950

Ala Ala Arg Leu Ala Val Glu Gly Met Val Ala Glu Leu Ile Asn
1955 1960 1965

Cys Gln Ala Asp Val Asn Ala Val Asp Asp His Gly Lys Ser Ala
1970 1975 1980

Leu His Trp Ala Ala Ala Val Asn Asn Val Glu Ala Thr Leu Leu
1985 1990 1995

Leu Leu Lys Asn Gly Ala Asn Arg Asp Met Gln Asp Asn Lys Glu
2000 2005 2010

Glu Thr Pro Leu Phe Leu Ala Ala Arg Glu Gly Ser Tyr Glu Ala
2015 2020 2025

Ala Lys Ile Leu Leu Asp His Phe Ala Asn Arg Asp Ile Thr Asp
2030 2035 2040

His Met Asp Arg Leu Pro Arg Asp Val Ala Arg Asp Arg Met His
2045 2050 2055

His Asp Ile Val Arg Leu Leu Asp Glu Tyr Asn Val Thr Pro Ser
2060 2065 2070

Pro Pro Gly Thr Val Leu Thr Ser Ala Leu Ser Pro Val Ile Cys
2075 2080 2085

Gly Pro Asn Arg Ser Phe Leu Ser Leu Lys His Thr Pro Met Gly
2090 2095 2100

Lys Lys Ser Arg Arg Pro Ser Ala Lys Ser Thr Met Pro Thr Ser
2105 2110 2115

Leu Pro Asn Leu Ala Lys Glu Ala Lys Asp Ala Lys Gly Ser Arg
2120 2125 2130

Arg Lys Lys Ser Leu Ser Glu Lys Val Gln Leu Ser Glu Ser Ser
2135 2140 2145

Val Thr Leu Ser Pro Val Asp Ser Leu Glu Ser Pro His Thr Tyr
2150 2155 2160

Val Ser Asp Thr Thr Ser Ser Pro Met Ile Thr Ser Pro Gly Ile
2165 2170 2175

Leu Gln Ala Ser Pro Asn Pro Met Leu Ala Thr Ala Ala Pro Pro
2180 2185 2190

Ala Pro Val His Ala Gln His Ala Leu Ser Phe Ser Asn Leu His
2195 2200 2205

Glu Met Gln Pro Leu Ala His Gly Ala Ser Thr Val Leu Pro Ser
2210 2215 2220

Val Ser Gln Leu Leu Ser His His His Ile Val Ser Pro Gly Ser
2225 2230 2235

```
Gly Ser Ala Gly Ser Leu Ser Arg Leu His Pro Val Pro Val Pro
                2240                2245                2250

Ala Asp Trp Met Asn Arg Met Glu Val Asn Glu Thr Gln Tyr Asn
                2255                2260                2265

Glu Met Phe Gly Met Val Leu Ala Pro Ala Glu Gly Thr His Pro
                2270                2275                2280

Gly Ile Ala Pro Gln Ser Arg Pro Pro Glu Gly Lys His Ile Thr
                2285                2290                2295

Thr Pro Arg Glu Pro Leu Pro Pro Ile Val Thr Phe Gln Leu Ile
                2300                2305                2310

Pro Lys Gly Ser Ile Ala Gln Pro Ala Gly Ala Pro Gln Pro Gln
                2315                2320                2325

Ser Thr Cys Pro Pro Ala Val Ala Gly Pro Leu Pro Thr Met Tyr
                2330                2335                2340

Gln Ile Pro Glu Met Ala Arg Leu Pro Ser Val Ala Phe Pro Thr
                2345                2350                2355

Ala Met Met Pro Gln Gln Asp Gly Gln Val Ala Gln Thr Ile Leu
                2360                2365                2370

Pro Ala Tyr His Pro Phe Pro Ala Ser Val Gly Lys Tyr Pro Thr
                2375                2380                2385

Pro Pro Ser Gln His Ser Tyr Ala Ser Ser Asn Ala Ala Glu Arg
                2390                2395                2400

Thr Pro Ser His Ser Gly His Leu Gln Gly Glu His Pro Tyr Leu
                2405                2410                2415

Thr Pro Ser Pro Glu Ser Pro Asp Gln Trp Ser Ser Ser Ser Pro
                2420                2425                2430

His Ser Ala Ser Asp Trp Ser Asp Val Thr Thr Ser Pro Thr Pro
                2435                2440                2445

Gly Gly Ala Gly Gly Gly Gln Arg Gly Pro Gly Thr His Met Ser
                2450                2455                2460

Glu Pro Pro His Asn Asn Met Gln Val Tyr Ala
                2465                2470


<210> SEQ ID NO 46
<211> LENGTH: 2002
<212> TYPE: PRT
<213> ORGANISM: Homo sapiens
<220> FEATURE:
<223> OTHER INFORMATION: human Notch4

<400> SEQUENCE: 46

Met Gln Pro Pro Ser Leu Leu Leu Leu Leu Leu Leu Leu Leu Leu
1               5                   10                  15

Cys Val Ser Val Val Arg Pro Arg Gly Leu Leu Cys Gly Ser Phe
                20                  25                  30

Pro Glu Pro Cys Ala Asn Gly Gly Thr Cys Leu Ser Leu Ser Leu
                35                  40                  45

Gly Gln Gly Thr Cys Gln Cys Ala Pro Gly Phe Leu Gly Glu Thr
                50                  55                  60

Cys Gln Phe Pro Asp Pro Cys Gln Asn Ala Gln Leu Cys Gln Asn
                65                  70                  75

Gly Gly Ser Cys Gln Ala Leu Leu Pro Ala Pro Leu Gly Leu Pro
                80                  85                  90

Ser Ser Pro Ser Pro Leu Thr Pro Ser Phe Leu Cys Thr Cys Leu
                95                  100                 105

Pro Gly Phe Thr Gly Glu Arg Cys Gln Ala Lys Leu Glu Asp Pro
```

-continued

```
                110                 115                 120

Cys Pro Pro Ser Phe Cys Ser Lys Arg Gly Arg Cys His Ile Gln
                125                 130                 135

Ala Ser Gly Arg Pro Gln Cys Ser Cys Met Pro Gly Trp Thr Gly
                140                 145                 150

Glu Gln Cys Gln Leu Arg Asp Phe Cys Ser Ala Asn Pro Cys Val
                155                 160                 165

Asn Gly Gly Val Cys Leu Ala Thr Tyr Pro Gln Ile Gln Cys His
                170                 175                 180

Cys Pro Pro Gly Phe Glu Gly His Ala Cys Glu Arg Asp Val Asn
                185                 190                 195

Glu Cys Phe Gln Asp Pro Gly Pro Cys Pro Lys Gly Thr Ser Cys
                200                 205                 210

His Asn Thr Leu Gly Ser Phe Gln Cys Leu Cys Pro Val Gly Gln
                215                 220                 225

Glu Gly Pro Arg Cys Glu Leu Arg Ala Gly Pro Cys Pro Pro Arg
                230                 235                 240

Gly Cys Ser Asn Gly Gly Thr Cys Gln Leu Met Pro Glu Lys Asp
                245                 250                 255

Ser Thr Phe His Leu Cys Leu Cys Pro Pro Gly Phe Ile Gly Pro
                260                 265                 270

Gly Cys Glu Val Asn Pro Asp Asn Cys Val Ser His Gln Cys Gln
                275                 280                 285

Asn Gly Gly Thr Cys Gln Asp Gly Leu Asp Thr Tyr Thr Cys Leu
                290                 295                 300

Cys Pro Glu Thr Trp Thr Gly Trp Asp Cys Ser Glu Asp Val Asp
                305                 310                 315

Glu Cys Glu Ala Gln Gly Pro Pro His Cys Arg Asn Gly Gly Thr
                320                 325                 330

Cys Gln Asn Ser Ala Gly Ser Phe His Cys Val Cys Val Ser Gly
                335                 340                 345

Trp Gly Gly Thr Ser Cys Glu Glu Asn Leu Asp Asp Cys Ile Ala
                350                 355                 360

Ala Thr Cys Ala Pro Gly Ser Thr Cys Ile Asp Arg Val Gly Ser
                365                 370                 375

Phe Ser Cys Leu Cys Pro Pro Gly Arg Thr Gly Leu Leu Cys His
                380                 385                 390

Leu Glu Asp Met Cys Leu Ser Gln Pro Cys His Gly Asp Ala Gln
                395                 400                 405

Cys Ser Thr Asn Pro Leu Thr Gly Ser Thr Leu Cys Leu Cys Gln
                410                 415                 420

Pro Gly Tyr Ser Gly Pro Thr Cys His Gln Asp Leu Asp Glu Cys
                425                 430                 435

Leu Met Ala Gln Gln Gly Pro Ser Pro Cys Glu His Gly Gly Ser
                440                 445                 450

Cys Leu Asn Thr Pro Gly Ser Phe Asn Cys Leu Cys Pro Pro Gly
                455                 460                 465

Tyr Thr Gly Ser Arg Cys Glu Ala Asp His Asn Glu Cys Leu Ser
                470                 475                 480

Gln Pro Cys His Pro Gly Ser Thr Cys Leu Asp Leu Leu Ala Thr
                485                 490                 495

Phe His Cys Leu Cys Pro Pro Gly Leu Glu Gly Gln Leu Cys Glu
                500                 505                 510
```

-continued

```
Val Glu Thr Asn Glu Cys Ala Ser Ala Pro Cys Leu Asn His Ala
                515                 520                 525

Asp Cys His Asp Leu Leu Asn Gly Phe Gln Cys Ile Cys Leu Pro
                530                 535                 540

Gly Phe Ser Gly Thr Arg Cys Glu Glu Asp Ile Asp Glu Cys Arg
                545                 550                 555

Ser Ser Pro Cys Ala Asn Gly Gly Gln Cys Gln Asp Gln Pro Gly
                560                 565                 570

Ala Phe His Cys Lys Cys Leu Pro Gly Phe Glu Gly Pro Arg Cys
                575                 580                 585

Gln Thr Glu Val Asp Glu Cys Leu Ser Asp Pro Cys Pro Val Gly
                590                 595                 600

Ala Ser Cys Leu Asp Leu Pro Gly Ala Phe Phe Cys Leu Cys Pro
                605                 610                 615

Ser Gly Phe Thr Gly Gln Leu Cys Glu Val Pro Leu Cys Ala Pro
                620                 625                 630

Asn Leu Cys Gln Pro Lys Gln Ile Cys Lys Asp Gln Lys Asp Lys
                635                 640                 645

Ala Asn Cys Leu Cys Pro Asp Gly Ser Pro Gly Cys Ala Pro Pro
                650                 655                 660

Glu Asp Asn Cys Thr Cys His His Gly His Cys Gln Arg Ser Ser
                665                 670                 675

Cys Val Cys Asp Val Gly Trp Thr Gly Pro Glu Cys Glu Ala Glu
                680                 685                 690

Leu Gly Gly Cys Ile Ser Ala Pro Cys Ala His Gly Gly Thr Cys
                695                 700                 705

Tyr Pro Gln Pro Ser Gly Tyr Asn Cys Thr Cys Pro Thr Gly Tyr
                710                 715                 720

Thr Gly Pro Thr Cys Ser Glu Glu Met Thr Ala Cys His Ser Gly
                725                 730                 735

Pro Cys Leu Asn Gly Gly Ser Cys Asn Pro Ser Pro Gly Gly Tyr
                740                 745                 750

Tyr Cys Thr Cys Pro Pro Ser His Thr Gly Pro Gln Cys Gln Thr
                755                 760                 765

Ser Thr Asp Tyr Cys Val Ser Ala Pro Cys Phe Asn Gly Gly Thr
                770                 775                 780

Cys Val Asn Arg Pro Gly Thr Phe Ser Cys Leu Cys Ala Met Gly
                785                 790                 795

Phe Gln Gly Pro Arg Cys Glu Gly Lys Leu Arg Pro Ser Cys Ala
                800                 805                 810

Asp Ser Pro Cys Arg Asn Arg Ala Thr Cys Gln Asp Ser Pro Gln
                815                 820                 825

Gly Pro Arg Cys Leu Cys Pro Thr Gly Tyr Thr Gly Gly Ser Cys
                830                 835                 840

Gln Thr Leu Met Asp Leu Cys Ala Gln Lys Pro Cys Pro Arg Asn
                845                 850                 855

Ser His Cys Leu Gln Thr Gly Pro Ser Phe His Cys Leu Cys Leu
                860                 865                 870

Gln Gly Trp Thr Gly Pro Leu Cys Asn Leu Pro Leu Ser Ser Cys
                875                 880                 885

Gln Lys Ala Ala Leu Ser Gln Gly Ile Asp Val Ser Ser Leu Cys
                890                 895                 900

His Asn Gly Gly Leu Cys Val Asp Ser Gly Pro Ser Tyr Phe Cys
                905                 910                 915
```

-continued

```
His Cys Pro Pro Gly Phe Gln Gly Ser Leu Cys Gln Asp His Val
                920                 925                 930

Asn Pro Cys Glu Ser Arg Pro Cys Gln Asn Gly Ala Thr Cys Met
                935                 940                 945

Ala Gln Pro Ser Gly Tyr Leu Cys Gln Cys Ala Pro Gly Tyr Asp
                950                 955                 960

Gly Gln Asn Cys Ser Lys Glu Leu Asp Ala Cys Gln Ser Gln Pro
                965                 970                 975

Cys His Asn His Gly Thr Cys Thr Pro Lys Pro Gly Gly Phe His
                980                 985                 990

Cys Ala Cys Pro Pro Gly Phe Val Gly Leu Arg Cys Glu Gly Asp
                995                 1000                1005

Val Asp Glu Cys Leu Asp Gln Pro Cys His Pro Thr Gly Thr Ala
                1010                1015                1020

Ala Cys His Ser Leu Ala Asn Ala Phe Tyr Cys Gln Cys Leu Pro
                1025                1030                1035

Gly His Thr Gly Gln Trp Cys Glu Val Glu Ile Asp Pro Cys His
                1040                1045                1050

Ser Gln Pro Cys Phe His Gly Gly Thr Cys Glu Ala Thr Ala Gly
                1055                1060                1065

Ser Pro Leu Gly Phe Ile Cys His Cys Pro Lys Gly Phe Glu Gly
                1070                1075                1080

Pro Thr Cys Ser His Arg Ala Pro Ser Cys Gly Phe His His Cys
                1085                1090                1095

His His Gly Gly Leu Cys Leu Pro Ser Pro Lys Pro Gly Phe Pro
                1100                1105                1110

Pro Arg Cys Ala Cys Leu Ser Gly Tyr Gly Gly Pro Asp Cys Leu
                1115                1120                1125

Thr Pro Pro Ala Pro Lys Gly Cys Gly Pro Pro Ser Pro Cys Leu
                1130                1135                1140

Tyr Asn Gly Ser Cys Ser Glu Thr Thr Gly Leu Gly Gly Pro Gly
                1145                1150                1155

Phe Arg Cys Ser Cys Pro His Ser Ser Pro Gly Pro Arg Cys Gln
                1160                1165                1170

Lys Pro Gly Ala Lys Gly Cys Glu Gly Arg Ser Gly Asp Gly Ala
                1175                1180                1185

Cys Asp Ala Gly Cys Ser Gly Pro Gly Gly Asn Trp Asp Gly Gly
                1190                1195                1200

Asp Cys Ser Leu Gly Val Pro Asp Pro Trp Lys Gly Cys Pro Ser
                1205                1210                1215

His Ser Arg Cys Trp Leu Leu Phe Arg Asp Gly Gln Cys His Pro
                1220                1225                1230

Gln Cys Asp Ser Glu Glu Cys Leu Phe Asp Gly Tyr Asp Cys Glu
                1235                1240                1245

Thr Pro Pro Ala Cys Thr Pro Ala Tyr Asp Gln Tyr Cys His Asp
                1250                1255                1260

His Phe His Asn Gly His Cys Glu Lys Gly Cys Asn Thr Ala Glu
                1265                1270                1275

Cys Gly Trp Asp Gly Gly Asp Cys Arg Pro Glu Asp Gly Asp Pro
                1280                1285                1290

Glu Trp Gly Pro Ser Leu Ala Leu Leu Val Val Leu Ser Pro Pro
                1295                1300                1305

Ala Leu Asp Gln Gln Leu Phe Ala Leu Ala Arg Val Leu Ser Leu
```

```
                1310                1315                1320

Thr Leu Arg Val Gly Leu Trp Val Arg Lys Asp Arg Asp Gly Arg
                1325                1330                1335

Asp Met Val Tyr Pro Tyr Pro Gly Ala Arg Ala Glu Glu Lys Leu
                1340                1345                1350

Gly Gly Thr Arg Asp Pro Thr Tyr Gln Glu Arg Ala Ala Pro Gln
                1355                1360                1365

Thr Gln Pro Leu Gly Lys Glu Thr Asp Ser Leu Ser Ala Gly Phe
                1370                1375                1380

Val Val Val Met Gly Val Asp Leu Ser Arg Cys Gly Pro Asp His
                1385                1390                1395

Pro Ala Ser Arg Cys Pro Trp Asp Pro Gly Leu Leu Leu Arg Phe
                1400                1405                1410

Leu Ala Ala Met Ala Ala Val Gly Ala Leu Glu Pro Leu Leu Pro
                1415                1420                1425

Gly Pro Leu Leu Ala Val His Pro His Ala Gly Thr Ala Pro Pro
                1430                1435                1440

Ala Asn Gln Leu Pro Trp Pro Val Leu Cys Ser Pro Val Ala Gly
                1445                1450                1455

Val Ile Leu Leu Ala Leu Gly Ala Leu Leu Val Leu Gln Leu Ile
                1460                1465                1470

Arg Arg Arg Arg Arg Glu His Gly Ala Leu Trp Leu Pro Pro Gly
                1475                1480                1485

Phe Thr Arg Arg Pro Arg Thr Gln Ser Ala Pro His Arg Arg Arg
                1490                1495                1500

Pro Pro Leu Gly Glu Asp Ser Ile Gly Leu Lys Ala Leu Lys Pro
                1505                1510                1515

Lys Ala Glu Val Asp Glu Asp Gly Val Val Met Cys Ser Gly Pro
                1520                1525                1530

Glu Glu Gly Glu Glu Val Gly Gln Ala Glu Glu Thr Gly Pro Pro
                1535                1540                1545

Ser Thr Cys Gln Leu Trp Ser Leu Ser Gly Gly Cys Gly Ala Leu
                1550                1555                1560

Pro Gln Ala Ala Met Leu Thr Pro Pro Gln Glu Ser Glu Met Glu
                1565                1570                1575

Ala Pro Asp Leu Asp Thr Arg Gly Pro Asp Gly Val Thr Pro Leu
                1580                1585                1590

Met Ser Ala Val Cys Cys Gly Glu Val Gln Ser Gly Thr Phe Gln
                1595                1600                1605

Gly Ala Trp Leu Gly Cys Pro Glu Pro Trp Glu Pro Leu Leu Asp
                1610                1615                1620

Gly Gly Ala Cys Pro Gln Ala His Thr Val Gly Thr Gly Glu Thr
                1625                1630                1635

Pro Leu His Leu Ala Ala Arg Phe Ser Arg Pro Thr Ala Ala Arg
                1640                1645                1650

Arg Leu Leu Glu Ala Gly Ala Asn Pro Asn Gln Pro Asp Arg Ala
                1655                1660                1665

Gly Arg Thr Pro Leu His Ala Ala Val Ala Ala Asp Ala Arg Glu
                1670                1675                1680

Val Cys Gln Leu Leu Leu Arg Ser Arg Gln Thr Ala Val Asp Ala
                1685                1690                1695

Arg Thr Glu Asp Gly Thr Thr Pro Leu Met Leu Ala Ala Arg Leu
                1700                1705                1710
```

```
Ala Val Glu Asp Leu Val Glu Glu Leu Ile Ala Ala Gln Ala Asp
                1715                1720                1725

Val Gly Ala Arg Asp Lys Trp Gly Lys Thr Ala Leu His Trp Ala
                1730                1735                1740

Ala Ala Val Asn Asn Ala Arg Ala Ala Arg Ser Leu Leu Gln Ala
                1745                1750                1755

Gly Ala Asp Lys Asp Ala Gln Asp Asn Arg Glu Gln Thr Pro Leu
                1760                1765                1770

Phe Leu Ala Ala Arg Glu Gly Ala Val Glu Val Ala Gln Leu Leu
                1775                1780                1785

Leu Gly Leu Gly Ala Ala Arg Glu Leu Arg Asp Gln Ala Gly Leu
                1790                1795                1800

Ala Pro Ala Asp Val Ala His Gln Arg Asn His Trp Asp Leu Leu
                1805                1810                1815

Thr Leu Leu Glu Gly Ala Gly Pro Pro Glu Ala Arg His Lys Ala
                1820                1825                1830

Thr Pro Gly Arg Glu Ala Gly Pro Phe Pro Arg Ala Arg Thr Val
                1835                1840                1845

Ser Val Ser Val Pro Pro His Gly Gly Gly Ala Leu Pro Arg Cys
                1850                1855                1860

Arg Thr Leu Ser Ala Gly Ala Gly Pro Arg Gly Gly Gly Ala Cys
                1865                1870                1875

Leu Gln Ala Arg Thr Trp Ser Val Asp Leu Ala Ala Arg Gly Gly
                1880                1885                1890

Gly Ala Tyr Ser His Cys Arg Ser Leu Ser Gly Val Gly Ala Gly
                1895                1900                1905

Gly Gly Pro Thr Pro Arg Gly Arg Arg Phe Ser Ala Gly Met Arg
                1910                1915                1920

Gly Pro Arg Pro Asn Pro Ala Ile Met Arg Gly Arg Tyr Gly Val
                1925                1930                1935

Ala Ala Gly Arg Gly Gly Arg Val Ser Thr Asp Asp Trp Pro Cys
                1940                1945                1950

Asp Trp Val Ala Leu Gly Ala Cys Gly Ser Ala Ser Asn Ile Pro
                1955                1960                1965

Ile Pro Pro Pro Cys Leu Thr Pro Ser Pro Glu Arg Gly Ser Pro
                1970                1975                1980

Gln Leu Asp Cys Gly Pro Pro Ala Leu Gln Glu Met Pro Ile Asn
                1985                1990                1995

Gln Gly Gly Glu Gly Lys Lys
                2000
```

<210> SEQ ID NO 47
<211> LENGTH: 135
<212> TYPE: DNA
<213> ORGANISM: Artificial sequence
<220> FEATURE:
<223> OTHER INFORMATION: sequence is synthesized

<400> SEQUENCE: 47

```
atgggtccag gtgcaagagg tagaaggcgt agaaggagac caatgagccc          50

acctcctccg ccacctccag tgagagcact gcctttgctg ttgctgctgg         100

ctggacctgg tgcagcagct cctccttgcc  tggac                         135
```

<210> SEQ ID NO 48
<211> LENGTH: 135
<212> TYPE: DNA

```
<213> ORGANISM: Artificial sequence
<220> FEATURE:
<223> OTHER INFORMATION: Sequence is synthesized

<400> SEQUENCE: 48

atggggccgg gggcccgtgg ccgccgccgc cgccgtcgcc cgatgtcgcc          50

gccaccgcca ccgccacccg tgcgggcgct gcccctgctg ctgctgctag         100

cggggccggg ggctgcagcc cccccttgcc  tggac                        135
```

ANTAGONIST ANTI-NOTCH3 ANTIBODIES AND THEIR USE IN THE PREVENTION AND TREATMENT OF NOTCH3-RELATED DISEASES

RELATED APPLICATIONS

This application claims the benefit of U.S. Provisional Patent Application No. 60/875,597, filed Dec. 18, 2006, and U.S. Provisional Patent Application No. 60/879,218, filed Jan. 6, 2007, the disclosures of which are incorporated herein by reference in their entirety.

FIELD OF THE INVENTION

The present invention relates to antagonist anti-Notch3 antibodies and their use in the amelioration, treatment, or prevention of a Notch3-related disease or disorder.

BACKGROUND OF THE INVENTION

The Notch gene was first described in 1917 when a strain of the fruit fly *Drosophila melanogaster* was found to have notched wing blades (Morgan, *Am Nat* 51:513 (1917)). The gene was cloned almost seventy years later and was determined to be a cell surface receptor playing a key role in the development of many different cell types and tissues in *Drosophila* (Wharton et al., *Cell* 43:567 (1985)). The Notch signaling pathway was soon found to be a signaling mechanism mediated by cell-cell contact and has been evolutionarily conserved from *Drosophila* to human. Notch receptors have been found to be involved in many cellular processes, such as differentiation, cell fate decisions, maintenance of stem cells, cell motility, proliferation, and apoptosis in various cell types during development and tissue homeostasis (For review, see Artavanis-Tsakonas, et al., *Science* 268:225 (1995)).

Mammals possess four Notch receptor proteins (designated Notch1 to Notch4) and five corresponding ligands (designated Delta-1 (DLL-1), Delta-3 (DLL-3), Delta-4 (DLL-4), Jagged-1 and Jagged-2). The mammalian Notch receptor genes encode ~300 kD proteins that are cleaved during their transport to the cell surface and exist as heterodimers. The extracellular portion of the Notch receptor has thirty-four epidermal growth factor (EGF)-like repeats and three cysteine-rich Notch/LIN12 repeats. The association of two cleaved subunits is mediated by sequences lying immediately N-terminal and C-terminal of the cleavage site, and these two subunits constitute the Notch heterodimerization (HD) domains (Wharton, et al., *Cell* 43:567 (1985); Kidd, et al., *Mol Cell Biol* 6:3431 (1986); Kopczynski, et al., *Genes Dev* 2:1723 (1988); Yochem, et al., *Nature* 335:547 (1988)).

At present, it is still not clear how Notch signaling is regulated by different receptors or how the five ligands differ in their signaling or regulation. The differences in signaling and/or regulation may be controlled by their expression patterns in different tissues or by different environmental cues. It has been documented that Notch ligand proteins, including Jagged/Serrate and Delta/Delta-like, specifically bind to the EGF repeat region and induce receptor-mediated Notch signaling (reviewed by Bray, *Nature Rev Mol Cell Biol.* 7:678 (2006), and by Kadesch, *Exp Cell Res.* 260:1 (2000)). Among the EGF repeats, the 10th to 12th repeats are required for ligand binding to the Notch receptor, and the other EGF repeats may enhance receptor-ligand interaction (Xu, et al., *J Biol Chem.* 280:30158 (2005); Shimizu, et al., *Biochem Biophys Res Comm.* 276:385 (2000)). Although the LIN12 repeats and the dimerization domain are not directly involved in ligand binding, they play important roles in maintaining the heterodimeric protein complex, preventing ligand-independent protease cleavage and receptor activation (Sanche-Irizarry, et al., *Mol Cell Biol.* 24:9265 (2004); Vardar et al., *Biochem.* 42:7061 (2003)).

The expression of mutant forms of Notch receptors in developing *Xenopus* embryos interferes profoundly with normal development (Coffman, et al., *Cell* 73: 659 (1993)). A Notch1 knockout was found to be embryonic lethal in mice (Swiatek, et al., *Genes & Dev* 8:707 (1994)). In humans, there have been several genetic diseases, including cancer, linked to different Notch receptor mutations (Artavanis-Tsakonas, et al., *Science* 284:770 (1999)). For instance, aberrant activation of Notch1 receptor caused by translocation can lead to T cell lymphoblastic leukemia (Ellisen, et al., *Cell* 66:649 (1991)). Certain mutations in the HD domains of Notch1 receptor enhance signaling without ligand binding (Malecki, et al., *Mol Cell Biol* 26:4642 (2006)), further implicating their roles in Notch receptor activation. The signal induced by ligand binding is transmitted to the nucleus by a process involving two proteolytic cleavages of the receptor followed by nuclear translocation of the intracellular domain (Notch-IC). Although LIN12 repeats and HD domains were thought to prevent signaling in the absence of ligands, it is still unclear how ligand binding facilitates proteolytic cleavage events.

Notch receptors have been linked to a wide range of diseases including cancer, neurological disorders, and immune diseases, as evidenced by reports of the over-expression of Notch receptors in various human disease tissues and cell lines as compared to normal or nonmalignant cells (Joutel, et al. *Cell & Dev Biol* 9:619 (1998); Nam, et al., *Curr Opin Chem Biol* 6:501 (2002)). The Notch3 receptor is over-expressed in various solid tumors, including non-small cell lung cancer (NSCLC) and ovarian cancer (Haruki, et al., *Cancer Res* 65:3555 (2005); Park, et al., *Cancer Res* 66:6312 (2006); Lu, et al., *Clin Cancer Res* 10:3291 (2004)), suggesting the significance of Notch3 receptor expression in solid tumors. Furthermore, Notch3 receptor expression is upregulated in plasma cell neoplasms, including multiple myeloma, plasma cell leukemia, and extramedullary plasmacytoma (Hedvat, et al., *Br J Haematol* 122:728 (2003); pancreatic cancer (Buchler, et al., *Ann Surg* 242:791 (2005)); and T cell acute lymphoblastic leukemias (T-ALL) (Bellavia, et al., *Proc Natl Acad Sci USA* 99:3788 (2002); Screpanti, et al., *Trends Mol Med* 9:30 (2003)). Notch3 receptor is also expressed in a subset of neuroblastoma cell lines and serves as a marker for this type of tumor that has constitutional or tumor-specific mutations in the homeobox gene Phox2B (van Limpt, et al., *Cancer Lett* 228:59 (2005)). Other indications and diseases that have been linked to Notch3 receptor expression include neurological disorders (Joutel, et al., *Nature* 383:707 (1996)), diabetes (Anastasi, et al., *J Immunol* 171:4504 (2003), rheumatoid arthritis (Yabe, et al., *J Orthop Sci* 10:589 (2005)), vascular related diseases (Sweeney, et al., *FASEB J* 18:1421 (2004)), and Alagille syndrome (Flynn, et al., *J Pathol* 204:55 (2004)).

Although Notch3 receptor over-expression (including gene amplification) has been observed in various cancers, no activating mutations have yet been reported. It is plausible that an increased level of Notch3 receptors in tumors can be activated by different ligands in stromal cells or tumor cells and lead to enhanced Notch3 signaling. Particularly, Notch ligands have been localized to the vascular endothelium during both development and tumorigenesis (Mailhos, et al., *Differentiation* 69:135 (2001); Taichman, et al., *Dev Dyn* 225: 166 (2002)), suggesting endothelial cells could provide the ligands for Notch3 receptor activation in tumors. Similar tumor-stroma cross-talk mediated by Notch ligand and receptor have been demonstrated in different type of cancers (Houde, et al., *Blood* 104: 3697 (2004); Jundt, et al., *Blood* 103: 3511 (2004); Zeng, et al., *Cancer Cell* 8: 13 (2005)). Increased Notch3 signaling caused by over-expression of intracellular Notch3 (Notch3-IC) can lead to tumorigenesis in T-ALL and breast cancer animal models (Vacca, et al., *The EMBO J* 25: 1000 (2006); Hu, et al., *Am J Pathol* 168: 973 (2006)).

Notch signaling and its role in cell self-renewal have been implicated in cancer stem cells, which are a minority population in tumors and can initiate tumor formation (Reya, et al., *Nature* 414:105 (2001)). Normal stem cells from many tissues, including intestinal and neuronal stem cells, depend on Notch signaling for self-renewal and fate determination (Fre, et al., *Nature,* 435: 964 (2005); van Es, et al., *Nature,* 435:959 (2005); Androutsellis-Theotokis, et al., *Nature,* 442: 823 (2006)). Similar mechanisms could exist in cancer stem cells, and inhibition of Notch signaling by γ-secretase inhibitors was shown to deplete cancer stem cells and block engraftment in embryonal brain tumors (Fan, et al., *Cancer Res* 66:7445 (2006)).

Inhibition of Notch signaling by γ-secretase inhibitor has striking antineoplastic effects in Notch-expressing transformed cells in vitro and in xenograft models (Weijzen, et al., *Nat Medicine* 8: 879 (2002); Bocchetta, et al., *Oncogene* 22:81 (2003); Weng, et al., *Science,* 306:269 (2004)). More recently, a γ-secretase inhibitor has been shown to efficaciously kill colon adenomas in Apc (min+) mice (van Es, et al., *Nature,* 435: 959 (2005)), although the therapeutic window, due to its effect on normal stem cells and the inhibition of multiple Notch pathways, is very narrow. Different from Notch1, a Notch3 gene knockout in mice was not embryonically lethal and had few defects (Domenga, et al., *Genes & Dev* 18: 2730 (2004)), suggesting that Notch 3 provides a potentially better therapeutic target than Notch1.

Tournier-Lasserve et al. (U.S. Application 2003/0186290) teach the association of Notch3 receptor and CADASIL. The application discloses various mutations in the Notch3 gene and their possible association with the disease CADASIL. The application suggests the use of diagnostic antibodies to detect such mutations. The application also suggests therapeutic antibodies to treat CADASIL, i.e. agonistic antibodies, but no specific antibodies are disclosed nor how to make such antibodies.

In view of the large number of human diseases associated with the Notch3 signaling pathway, it is important that new ways of preventing and treating these diseases be identified. The current invention provides novel anti-Notch3 antibodies useful for this unmet medical need.

SUMMARY OF THE INVENTION

The present invention provides novel antibodies and fragments thereof that specifically bind to a conformational epitope of the human Notch3 receptor, the epitope comprising the LIN12 domain and the heterodimerization domain. Another aspect of the invention includes the epitope binding site and antibodies that bind this same epitope as the antibodies of the present invention. The antibodies of the present invention inhibit ligand-induced signaling through the Notch3 receptor.

The invention includes the amino acid sequences of the variable heavy and light chain of the antibodies and their corresponding nucleic acid sequences. Another embodiment of the invention includes the CDR sequences of these antibodies. Another embodiment includes humanized forms of these antibodies.

Another embodiment of the present invention includes the cell lines and vectors harboring the antibody sequences of the present invention.

The present invention also includes the conformational epitope recognized by the antagonist antibodies of the invention. The present invention also includes antibodies that bind this conformational epitope. The embodiments include a Notch 3 conformational epitope comprising the LIN12 domain having at least 80%, 85%, 90%, or 95% sequence identity with SEQ ID NO. 9 and the dimerization domain 2 having at least 80%, 85%, 90%, or 95% sequence identity with SEQ ID NO. 18. More particularly, the Notch 3 conformational epitope comprising amino acid residues 1395-1396, 1402-1404 and 1420-1422 of the L1 LIN12 domain and amino acid residues 1576-1578 and 1626-1628 of the D2 dimerization domain. The present invention includes antibodies that bind this conformational epitope.

Another embodiment of the preset invention is the use of any of these antibodies for the preparation of a medicament or composition for the treatment of diseases and disorders associated with Notch 3 receptor activation.

Another embodiment of the preset invention is the use of any of these antibodies in the treatment of disorders associated with Notch 3 activation comprising the inhibition of said activation by, e.g., inhibiting Notch 3 signaling, or neutralization of the receptor by blocking ligand binding. Notch 3 related disorders may include, but are not limited to, T-cell acute lymphoblastic leukemia, lymphoma, liver disease involving aberrant vascularization, diabetes, ovarian cancer, diseases involving vascular cell fate, rheumatoid arthritis, pancreatic cancer, non-small cell lung cancer, plasma cell neoplasms (such as multiple myeloma, plasma cell leukemia, and extramedullary plasmacytoma), and neuroblastoma.

BRIEF DESCRIPTION OF THE FIGURES

FIG. 1 depicts the amino acid sequence of Notch3. The EGF repeat region extends from amino acid residue 43 to 1383; the LIN12 domain extends from amino acid residue 1384 to 1503; and the dimerization domain extends from amino acid residue 1504 to 1640.

FIG. 2 (A-H) depicts the amino acid sequence comparison between human Notch 1 (SEQ ID NO:44), Notch 2 (SEQ ID NO:45), Notch 3 (SEQ ID NO:1), and Notch 4 (SEQ ID NO:46).

FIG. 3 depicts the percent identity of Notch 1, Notch 2, Notch 3, and Notch 4.

FIGS. 4A and 4B depict the heavy and light chain variable region sequences of anti-Notch3 monoclonal antibody MAb 256A-4 (SEQ ID NO:2 and SEQ ID NO:3, respectively), with CDR regions underlined.

FIGS. 5A and 5B depict the heavy and light chain variable region sequences of anti-Notch3 monoclonal antibody MAb 256A-8 (SEQ ID NO:4 and SEQ ID NO:5, respectively), with CDR regions underlined.

FIG. 14 depicts the comparison of the engineered Notch3 leader peptide coding sequence (SEQ ID NO:47) to the native Notch3 leader peptide coding sequence (SEQ ID NO:48) (NCBI GENBANK® Accession No. NM_000435) showing the changes of nucleotides (14A) and the translated amino acid sequence of the engineered Notch leader peptide sequence (SEQ ID NO:6) (14B).

FIG. 16 depicts the amino acid sequences used in the Notch3 LIN12 domain epitope mapping of the MAb 256A-4 and 256A-8.

FIG. 17 depicts the amino acid sequences used in the Notch3 dimerization domain epitope mapping of the MAb 256A-4 and 256A-8.

FIG. 18 depicts a schematic of the epitope binding site for MAb 256A-4 and 256A-8.

DETAILED DESCRIPTION

Figure 6:
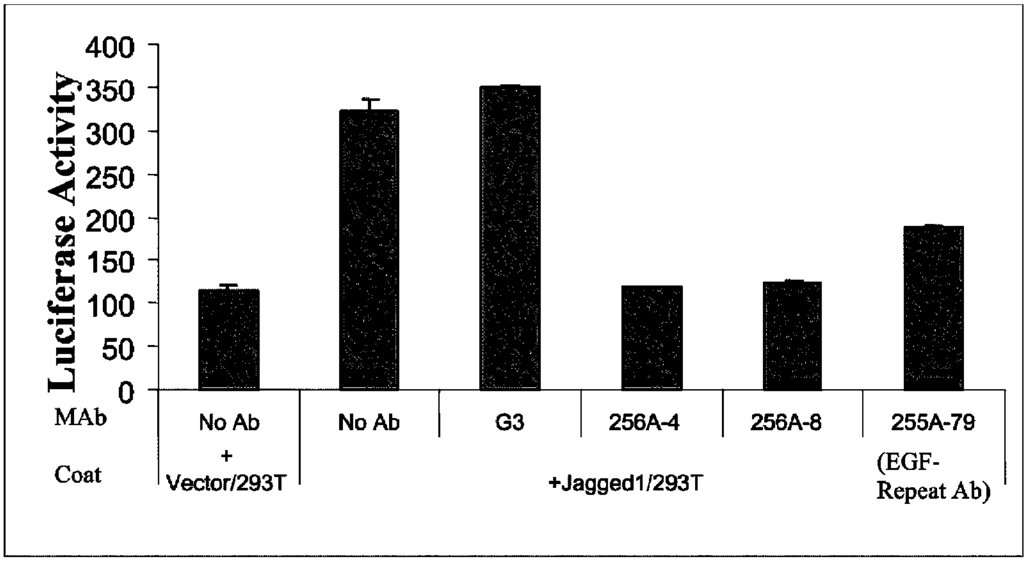
FIG. 6 depicts a luciferase reporter assay of Example 5 showing inhibitory effects by anti-Notch3 MAbs on the Notch3 ligand Jagged 1.

This invention is not limited to the particular methodology, protocols, cell lines, vectors, or reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise, e.g., reference to "a host cell" includes a plurality of such host cells. Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

All patents and publications mentioned herein are incorporated herein by reference to the extent allowed by law for the purpose of describing and disclosing the proteins, enzymes, vectors, host cells, and methodologies reported therein that might be used with the present invention. However, nothing herein is to be construed as an admission that the invention is not entitled to antedate such disclosure by virtue of prior invention.

Definitions

Terms used throughout this application are to be construed with ordinary and typical meaning to those of ordinary skill in the art. However, Applicants desire that the following terms be given the particular definitions as defined below.

The phrase "substantially identical" with respect to an antibody chain polypeptide sequence may be construed as an antibody chain exhibiting at least 70%, or 80%, or 90%, or 95% sequence identity to the reference polypeptide sequence. The term with respect to a nucleic acid sequence may be construed as a sequence of nucleotides exhibiting at least about 85%, or 90%, or 95%, or 97% sequence identity to the reference nucleic acid sequence.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- nor C-terminal extensions nor insertions shall be construed as reducing identity or homology. Methods and computer programs for the alignment are well known in the art. Sequence identity may be measured using sequence analysis software.

The term "antibody" is used in the broadest sense, and specifically covers monoclonal antibodies (including full length monoclonal antibodies), polyclonal antibodies, and multispecific antibodies (e.g., bispecific antibodies), and antibody fragments so long as they exhibit the desired biological activity. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. The antibodies of the invention can be of any type (e.g., IgG, IgE, IgM, IgD, IgA and IgY), class (e.g., IgG1, IgG2, IgG3, IgG4, IgA1 and IgA2) or subclass. Native antibodies and immunoglobulins are usually heterotetrameric glycoproteins of about 150,000 Daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end.

As used herein, "anti-Notch3 antibody" means an antibody which binds specifically to human Notch3 in such a manner so as to inhibit or substantially reduce the binding of Notch3 to its ligands or to inhibit Notch 3 signaling.

The term "variable" in the context of variable domain of antibodies, refers to the fact that certain portions of the variable domains differ extensively in sequence among antibodies and are used in the binding and specificity of each particular antibody for its particular target. However, the variability is not evenly distributed through the variable domains of antibodies. It is concentrated in three segments called complementarity determining regions (CDRs; i.e., CDR1, CDR2, and CDR3) also known as hypervariable regions both in the light chain and the heavy chain variable domains. The more highly conserved portions of variable domains are called the framework (FR). The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies (see Kabat, et al. Sequences of Proteins of Immunological Interest, National Institute of Health, Bethesda, Md. (1987)). As used herein, numbering of immunoglobulin amino acid residues is done according to the immunoglobulin amino acid residue numbering system of Kabat, et al., unless otherwise indicated.

The term "antibody fragment" refers to a portion of a full-length antibody, generally the target binding or variable region. Examples of antibody fragments include F(ab), F(ab'), $F(ab')_2$ and Fv fragments. The phrase "functional fragment or analog" of an antibody is a compound having qualitative biological activity in common with a full-length antibody. For example, a functional fragment or analog of an anti-Notch3 antibody is one which can bind to a Notch3 receptor in such a manner so as to prevent or substantially reduce the ability of the receptor to bind to its ligands or initiate signaling. As used herein, "functional fragment" with respect to antibodies, refers to Fv, F(ab) and $F(ab')_2$ fragments. An "Fv" fragment consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind target, although at a lower affinity than the entire binding site.

"Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

The term "diabodies" refers to small antibody fragments with two antigen-binding sites, which fragments comprise a heavy chain variable domain ($V_H$) connected to a light chain variable domain ($V_L$) in the same polypeptide chain. By using a linker that is too short to allow pairing between the two domains on the same chain, the domains are forced to pair with the complementary domains of another changing and create two antigen-binding sites.

The F(ab) fragment contains the constant domain of the light chain and the first constant domain (CH1) of the heavy chain. F(ab') fragments differ from F(ab) fragments by the addition of a few residues at the carboxyl terminus of the heavy chain CH1 domain including one or more cysteines from the antibody hinge region. F(ab') fragments are produced by cleavage of the disulfide bond at the hinge cysteines of the $F(ab')_2$ pepsin digestion product. Additional chemical couplings of antibody fragments are known to those of ordinary skill in the art.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison, et al., *Proc Natl Acad Sci USA* 81:6851 (1984)). Monoclonal antibodies are highly specific, being directed against a single target site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using well known techniques. The parent monoclonal antibodies to be used in accordance with the present invention may be made by the hybridoma method first described by Kohler, et al., *Nature* 256:495 (1975), or may be made by recombinant methods.

"Humanized" forms of non-human (e.g., murine) antibodies are chimeric immunoglobulins, immunoglobulin chains or fragments thereof (such as Fv, Fab, Fab', $F(ab')_2$ or other target-binding subsequences of antibodies) which contain minimal sequence derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region (Fc), typically that of a human immunoglobulin template chosen.

The terms "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included. The "host cells" used in the present invention generally are prokaryotic or eukaryotic hosts.

"Transformation" of a cellular organism, cell, or cell line with DNA means introducing DNA into the target cell so that the DNA is replicable, either as an extrachromosomal element or by chromosomal integration. "Transfection" of a cell or organism with DNA refers to the taking up of DNA, e.g., an expression vector, by the cell or organism whether or not any coding sequences are in fact expressed. The terms "transfected host cell" and "transformed" refer to a cell in which DNA was introduced. The cell is termed "host cell" and it may be either prokaryotic or eukaryotic. Typical prokaryotic host cells include various strains of *E. coli*. Typical eukaryotic host cells are mammalian, such as Chinese hamster ovary or cells of human origin. The introduced DNA sequence may be from the same species as the host cell or a different species from the host cell, or it may be a hybrid DNA sequence, containing some foreign and some homologous DNA.

The term "vector" means a DNA construct containing a DNA sequence which is operably linked to a suitable control sequence capable of effecting the expression of the DNA sequence in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. In the present specification, “plasmid” and “vector” are sometimes used interchangeably, as the plasmid is the most commonly used form of vector. However, the invention is intended to include such other forms of vectors which serve equivalent function as and which are, or become, known in the art.

“Mammal” for purposes of treatment refers to any animal classified as a mammal, including human, domestic and farm animals, nonhuman primates, and zoo, sports, or pet animals, such as dogs, horses, cats, cows, etc.

The word “label” when used herein refers to a detectable compound or composition which can be conjugated directly or indirectly to a molecule or protein, e.g., an antibody. The label may itself be detectable (e.g., radioisotope labels or fluorescent labels) or, in the case of an enzymatic label, may catalyze chemical alteration of a substrate compound or composition which is detectable.

As used herein, “solid phase” means a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol, and silicones. In certain embodiments, depending on the context, the solid phase can comprise the well of an assay plate; in others it is a purification column (e.g., an affinity chromatography column).

As used herein, the term “Notch3-mediated disorder” means a condition or disease which is characterized by the overexpression and/or hypersensitivity of the Notch3 receptor. Specifically it would be construed to include conditions associated with cancers such as non-small cell lung cancer, ovarian cancer, and T-cell acute lymphoblastic leukemia. Other cancers including pancreatic, prostate cancer, plasma cell neoplasms (e.g., multiple myeloma, plasma cell leukemia and extramedullary plasmacytoma), neuroblastoma and extramedullary plasmacytoma are also encompassed under the scope of this term. Other types of diseases include lymphoma, Alagille syndrome, liver disease involving aberrant vascularization, neurologic diseases, diabetes, diseases involving vascular cell fate, and rheumatoid arthritis.

Notch3 Receptor Immunogen for Generating Antibodies

Soluble targets or fragments thereof can be used as immunogens for generating antibodies. The antibody is directed against the target of interest. Preferably, the target is a biologically important polypeptide and administration of the antibody to a mammal suffering from a disease or disorder can result in a therapeutic benefit in that mammal. Whole cells may be used as the immunogen for making antibodies. The immunogen may be produced recombinantly or made using synthetic methods. The immunogen may also be isolated from a natural source.

For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to over-express the transmembrane molecule. Other forms of the immunogen useful for preparing antibodies will be apparent to those in the art.

Alternatively, a gene or a cDNA encoding human Notch3 receptor may be cloned into a plasmid or other expression vector and expressed in any of a number of expression systems according to methods well known to those of skill in the art. Methods of cloning and expressing Notch3 receptor and the nucleic acid sequence for human Notch3 receptor are known (see, for example, U.S. Pat. Nos. 5,821,332 and 5,759,546). Because of the degeneracy of the genetic code, a multitude of nucleotide sequences encoding Notch3 receptor protein or polypeptides may be used. One may vary the nucleotide sequence by selecting combinations based on possible codon choices. These combinations are made in accordance with the standard triplet genetic code as applied to the nucleotide sequence that codes for naturally occurring Notch3 receptor and all such variations may be considered. Any one of these polypeptides may be used in the immunization of an animal to generate antibodies that bind to human Notch3 receptor.

Recombinant Notch3 proteins from other species may also be used as immunogen to generate antibodies because of the high degree of conservation of the amino acid sequence of Notch3. A comparison between human and mouse Notch3 showed over 90% amino acid sequence identity between the two species.

The immunogen Notch3 receptor may, when beneficial, be expressed as a fusion protein that has the Notch3 receptor attached to a fusion segment. The fusion segment often aids in protein purification, e.g., by permitting the fusion protein to be isolated and purified by affinity chromatography, but can also be used to increase immunogenicity. Fusion proteins can be produced by culturing a recombinant cell transformed with a fusion nucleic acid sequence that encodes a protein including the fusion segment attached to either the carboxyl and/or amino terminal end of the protein. Fusion segments may include, but are not limited to, immunoglobulin Fc regions, glutathione-S-transferase, β-galactosidase, a poly-histidine segment capable of binding to a divalent metal ion, and maltose binding protein.

Recombinant Notch3 receptor protein as described in Example 1 was used to immunize mice to generate the hybridomas that produce the monoclonal antibodies of the present invention. Exemplary polypeptides comprise all or a portion of SEQ ID NO. 1 or variants thereof.

Antibody Generation

The antibodies of the present invention may be generated by any suitable method known in the art. The antibodies of the present invention may comprise polyclonal antibodies. Methods of preparing polyclonal antibodies are known to the skilled artisan (Harlow, et al., Antibodies: a Laboratory Manual, Cold spring Harbor Laboratory Press, 2nd ed. (1988), which is hereby incorporated herein by reference in its entirety).

For example, an immunogen as described in Example 1 may be administered to various host animals including, but not limited to, rabbits, mice, rats, etc., to induce the production of sera containing polyclonal antibodies specific for the antigen. The administration of the immunogen may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Additional examples of adjuvants which may be employed include the MPL-TDM adjuvant (monophosphoryl lipid A, synthetic trehalose dicorynomycolate). Immunization protocols are well known in the art and may be performed by any method that elicits an immune response in the animal host chosen. Adjuvants are also well known in the art.

Typically, the immunogen (with or without adjuvant) is injected into the mammal by multiple subcutaneous or intraperitoneal injections, or intramuscularly or through IV. The immunogen may include a Notch3 polypeptide, a fusion protein, or variants thereof. Depending upon the nature of the polypeptides (i.e., percent hydrophobicity, percent hydrophilicity, stability, net charge, isoelectric point etc.), it may be useful to conjugate the immunogen to a protein known to be immunogenic in the mammal being immunized. Such conjugation includes either chemical conjugation by derivatizing active chemical functional groups to both the immunogen and the immunogenic protein to be conjugated such that a covalent bond is formed, or through fusion-protein based methodology, or other methods known to the skilled artisan. Examples of such immunogenic proteins include, but are not limited to, keyhole limpet hemocyanin, ovalbumin, serum albumin, bovine thyroglobulin, soybean trypsin inhibitor, and promiscuous T helper peptides. Various adjuvants may be used to increase the immunological response as described above.

The antibodies of the present invention comprise monoclonal antibodies. Monoclonal antibodies are antibodies which recognize a single antigenic site. Their uniform specificity makes monoclonal antibodies much more useful than polyclonal antibodies, which usually contain antibodies that recognize a variety of different antigenic sites. Monoclonal antibodies may be prepared using hybridoma technology, such as those described by Kohler, et al., *Nature* 256:495 (1975); U.S. Pat. No. 4,376,110; Harlow, et al., Antibodies: A Laboratory Manual, Cold spring Harbor Laboratory Press, 2nd ed. (1988) and Hammerling, et al., Monoclonal Antibodies and T-Cell Hybridomas, Elsevier (1981), recombinant DNA methods, or other methods known to the artisan. Other examples of methods which may be employed for producing monoclonal antibodies include, but are not limited to, the human B-cell hybridoma technique (Kosbor, et al., *Immunology Today* 4:72 (1983); Cole, et al., *Proc Natl Acad Sci USA* 80:2026 (1983)), and the EBV-hybridoma technique (Cole, et al., Monoclonal Antibodies and Cancer Therapy, pp. 77-96, Alan R. Liss (1985)). Such antibodies may be of any immunoglobulin class including IgG, IgM, IgE, IgA, IgD and any subclass thereof. The hybridoma producing the mAb of this invention may be cultivated in vitro or in vivo.

In the hybridoma model, a host such as a mouse, a humanized mouse, a mouse with a human immune system, hamster, rabbit, camel, or any other appropriate host animal, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, Academic Press, pp. 59-103 (1986)).

Generally, in making antibody-producing hybridomas, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, pp. 59-103 (1986)). Immortalized cell lines are usually transformed mammalian cells, particularly myeloma cells of rodent, bovine or human origin. Typically, a rat or mouse myeloma cell line is employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), substances that prevent the growth of HGPRT-deficient cells.

Preferred immortalized cell lines are those that fuse efficiently, support stable high-level production of antibody by the selected antibody-producing cells, and are sensitive to a medium such as HAT medium. Among these myeloma cell lines are murine myeloma lines, such as those derived from the MOPC-21 and MPC-11 mouse tumors available from the Salk Institute Cell Distribution Center, San Diego, Calif., and SP2/0 or X63-Ag8-653 cells available from the American Type Culture Collection (ATCC), Manassas, Va., USA. Human myeloma and mouse-human heteromyeloma cell lines also have been described for the production of human monoclonal antibodies (Kozbor, *J Immunol* 133:3001 (1984); Brodeur, et al., Monoclonal Antibody Production Techniques and Applications, Marcel Dekker, Inc, pp. 51-63 (1987)). The mouse myeloma cell line NSO may also be used (European Collection of Cell Cultures, Salisbury, Wilshire, UK).

The culture medium in which hybridoma cells are grown is assayed for production of monoclonal antibodies directed against Notch3. The binding specificity of monoclonal antibodies produced by hybridoma cells may be determined by immunoprecipitation or by an in vitro binding assay, such as radioimmunoassay (RIA) or enzyme-linked immunoabsorbent assay (ELISA). Such techniques are known in the art and within the skill of the artisan. The binding affinity of the monoclonal antibody to Notch3 can, for example, be determined by a Scatchard analysis (Munson, et al., *Anal Biochem* 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, Academic Press, pp. 59-103 (1986)). Suitable culture media for this purpose include, for example, Dulbecco's Modified Eagle's Medium (D-MEM) or RPMI-1640 medium. In addition, the hybridoma cells may be grown in vivo as ascites tumors in an animal.

The monoclonal antibodies secreted by the subclones are suitably separated or isolated from the culture medium, ascites fluid, or serum by conventional immunoglobulin purification procedures such as, for example, protein A-SEPHAROSE® affinity media, hydroxylapatite chromatography, gel exclusion chromatography, gel electrophoresis, dialysis, or affinity chromatography.

A variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. DNA encoding the monoclonal antibodies of the invention is readily isolated and sequenced using conventional procedures (e.g., by using oligonucleotide probes that are capable of binding specifically to genes encoding the heavy and light chains of murine antibodies, or such chains from human, humanized, or other sources) (Innis, et al. In PCR Protocols. A Guide to Methods and Applications, Academic (1990), Sanger, et al., *Proc Natl Acad Sci* 74:5463 (1977)). The hybridoma cells serve as a source of such DNA. Once isolated, the DNA may be placed into expression vectors, which are then transfected into host cells such as *E. coli* cells, NS0 cells, Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison, et al., *Proc Natl Acad Sci USA* 81:6851 (1984)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

Antibody fragments which recognize specific epitopes may be generated by known techniques. Traditionally, these fragments were derived via proteolytic digestion of intact antibodies (see, e.g., Morimoto, et al., *J Biochem Biophys Methods* 24:107 (1992); Brennan, et al., *Science* 229:81 (1985)). For example, Fab and $F(ab')_2$ fragments of the invention may be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CH1 domain of the heavy chain. However, these fragments can now be produced directly by recombinant host ells. For example, the antibody fragments can be isolated from an antibody phage library. Alternatively, $F(ab')_2$-SH fragments can be directly recovered from *E. coli* and chemically coupled to form $F(ab')_2$ fragments (Carter, et al., *Bio/Technology* 10:163 (1992). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (Fv) (PCT patent application WO 93/16185).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science* 229:1202 (1985); Oi, et al., *BioTechniques* 4:214 (1986); Gillies, et al., *J Immunol Methods* 125:191 (1989); U.S. Pat. Nos. 5,807,715; 4,816,567; and 4,816,397, which are incorporated herein by reference in their entirety.

A humanized antibody is designed to have greater homology to a human immunoglobulin than animal-derived monoclonal antibodies. Humanization is a technique for making a chimeric antibody wherein substantially less than an intact human variable domain has been substituted by the corresponding sequence from a non-human species. Humanized antibodies are antibody molecules generated in a non-human species that bind the desired antigen having one or more complementarity determining regions (CDRs) from the non-human species and framework (FR) regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., U.S. Pat. No. 5,585,089; Riechmann, et al., *Nature* 332:323 (1988), which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28:489 (1991); Studnicka, et al., *Protein Engineering* 7:805 (1994); Roguska, et al., *Proc Natl Acad Sci USA* 91:969 (1994)), and chain shuffling (U.S. Pat. No. 5,565,332).

Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones, et al., *Nature* 321:522 (1986); Riechmann, et al., *Nature* 332:323 (1988); Verhoeyen, et al., *Science* 239:1534 (1988)), by substituting non-human CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

It is further important that humanized antibodies retain high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of certain residues in the functioning of the candidate immunoglobulin sequence, i.e., the analysis of residues that influence the ability of the candidate immunoglobulin sequences, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is maximized, although it is the CDR residues that directly and most substantially influence antigen binding.

The choice of human variable domains, both light and heavy, to be used in making the humanized antibodies is important to reduce antigenicity. According to an exemplary method, the so-called "best-fit" method, the sequence of the variable domain of a non-human antibody is screened against the entire library of known human variable-domain sequences. The human sequence which is closest to that of that of the non-human parent antibody is then accepted as the human FR for the humanized antibody (Sims, et al., *J Immunol* 151:2296 (1993); Chothia, et al., *J Mol Biol* 196:901 (1987)). Another method uses a particular framework derived from the consensus sequence of all human antibodies of a particular subgroup of light or heavy chains. The same framework may be used for several different humanized antibodies (Carter, et al., *Proc Natl Acad Sci USA* 89:4285 (1992); Presta, et al., *J Immunol* 151:2623 (1993)).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of Cole, et al. and Boerder, et al. are also available for the preparation of human monoclonal antibodies (Cole, et al., Monoclonal Antibodies and Cancer Therapy, Alan R. Riss (1985); and Boerner, et al., *J Immunol* 147:86 (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. See, e.g., Jakobovits, et al., *Proc Natl Acad Sci USA* 90:2551 (1993); Jakobovits, et al., *Nature* 362:255 (1993); Bruggermann, et al., *Year in Immunol* 7:33 (1993); Duchosal, et al., *Nature* 355:258 (1992)). The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg, et al., *Int Rev Immunol* 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Also human mAbs could be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers, et al., *Bio/technology* 12:899 (1988)).

Further, antibodies to the polypeptides of the invention can, in turn, be utilized to generate anti-idiotype antibodies that "mimic" polypeptides of the invention using techniques well known to those skilled in the art (See, e.g., Greenspan, et al., *FASEB J* 7:437 (1989); Nissinoff, *J Immunol* 147:2429 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The antibodies of the present invention may be bispecific antibodies. Bispecific antibodies are monoclonal, preferably human or humanized, antibodies that have binding specificities for at least two different antigens. In the present invention, one of the binding specificities may be directed towards Notch3, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are well known. Traditionally, the recombinant production of bispecific antibodies is based on the co-expression of two immunoglobulin heavy-chain/light-chain pairs, where the two heavy chains have different specificities (Milstein, et al., *Nature* 305:537 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker, et al., *EMBO J* 10:3655 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It may have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh, et al., *Meth In Enzym* 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies may be prepared in vitro using known methods in synthetic protein chemistry, including those involving cross-linking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

In addition, one can generate single-domain antibodies to Notch3. Examples of this technology have been described in WO94/25591 for antibodies derived from Camelidae heavy chain Ig, as well in US2003/0130496 describing the isolation of single domain fully human antibodies from phage libraries.

One can also create a single peptide chain binding molecules in which the heavy and light chain Fv regions are connected. Single chain antibodies ("scFv") and the method of their construction are described in U.S. Pat. No. 4,946,778. Alternatively, Fab can be constructed and expressed by similar means. All of the wholly and partially human antibodies are less immunogenic than wholly murine mAbs, and the fragments and single chain antibodies are also less immunogenic.

Antibodies or antibody fragments can be isolated from antibody phage libraries generated using the techniques described in McCafferty, et al., *Nature* 348:552 (1990). Clarkson, et al., *Nature* 352:624 (1991) and Marks, et al., *J Mol Biol* 222:581 (1991) describe the isolation of murine and human antibodies, respectively, using phage libraries. Subsequent publications describe the production of high affinity (nM range) human antibodies by chain shuffling (Marks, et al., *Bio/Technology* 10:779 (1992)), as well as combinatorial infection and in vivo recombination as a strategy for constructing very large phage libraries (Waterhouse, et al., *Nuc Acids Res* 21:2265 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc Natl Acad Sci USA* 81:6851 (1984)).

Another alternative is to use electrical fusion rather than chemical fusion to form hybridomas. This technique is well established. Instead of fusion, one can also transform a B cell to make it immortal using, for example, an Epstein Barr Virus, or a transforming gene. See, e.g., "Continuously Proliferating Human Cell Lines Synthesizing Antibody of Predetermined Specificity," Zurawaki, et al., in Monoclonal Antibodies, ed. by Kennett, et al., Plenum Press, pp. 19-33. (1980)). Anti-Notch3 mAbs can be raised by immunizing rodents (e.g., mice, rats, hamsters, and guinea pigs) with Notch3 protein, fusion protein, or its fragments expressed by either eukaryotic or prokaryotic systems. Other animals can be used for immunization, e.g., non-human primates, transgenic mice expressing immunoglobulins, and severe combined immunodeficient (SCID) mice transplanted with human B lymphocytes. Hybridomas can be generated by conventional procedures by fusing B lymphocytes from the immunized animals with myeloma cells (e.g., Sp2/0 and NSO), as described earlier (Köhler, et al., *Nature* 256:495 (1975)). In addition, anti-Notch3 antibodies can be generated by screening of recombinant single-chain Fv or Fab libraries from human B lymphocytes in phage-display systems. The specificity of the mAbs to Notch3 can be tested by ELISA, Western immunoblotting, or other immunochemical techniques. The inhibitory activity of the antibodies on complement activation can be assessed by hemolytic assays, using sensitized chicken or sheep RBCs for the classical complement pathway. The hybridomas in the positive wells are cloned by limiting dilution. The antibodies are purified for characterization for specificity to human Notch3 by the assays described above.

Identification of Anti-Notch-3 Antibodies

The present invention provides antagonist monoclonal antibodies that inhibit and neutralize the action of Notch3. In particular, the antibodies of the present invention bind to and inhibit the activation of Notch3. The antibodies of the present invention include the antibodies designated 256A-4 and 256A-8, which are disclosed herein. The present invention also includes antibodies that bind to the same epitope as one of these antibodies.

Candidate anti-Notch3 antibodies were tested by enzyme linked immunosorbent assay (ELISA), Western immunoblotting, or other immunochemical techniques. Assays performed to characterize the individual antibodies are described in the Examples.

Antibodies of the invention include, but are not limited to, polyclonal, monoclonal, monovalent, bispecific, heteroconjugate, multispecific, human, humanized or chimeric antibodies, single chain antibodies, single-domain antibodies, Fab fragments, F(ab') fragments, fragments produced by a Fab expression library, anti-idiotypic (anti-id) antibodies (including, e.g., anti-id antibodies to antibodies of the invention), and epitope-binding fragments of any of the above.

The antibodies may be human antigen-binding antibody fragments of the present invention and include, but are not limited to, Fab, Fab' and $F(ab')_2$, Fd, single-chain Fvs (scFv), single-chain antibodies, disulfide-linked Fvs (sdFv) and single-domain antibodies comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments comprising any combination of variable region(s) with a hinge region, CH1, CH2, and CH3 domains. The antibodies of the invention may be from any animal origin including birds and mammals. Preferably, the antibodies are from human, non-human primates, rodents (e.g., mouse and rat), donkey, sheep, rabbit, goat, guinea pig, camel, horse, or chicken.

As used herein, "human" antibodies" include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati, et al.

The antibodies of the present invention may be monospecific, bispecific, trispecific or of greater multispecificity. Multispecific antibodies may be specific for different epitopes of Notch3 or may be specific for both Notch3 as well as for a heterologous epitope, such as a heterologous polypeptide or solid support material. See, e.g., PCT publications WO 93/17715; WO 92/08802; WO 91/00360; WO 92/05793; Tutt, et al., *J Immunol* 147:60 (1991); U.S. Pat. Nos. 4,474,893; 4,714,681; 4,925,648; 5,573,920; 5,601,819; Kostelny, et al., *J Immunol* 148:1547 (1992).

Antibodies of the present invention may be described or specified in terms of the epitope(s) or portion(s) of Notch3 which they recognize or specifically bind. The epitope(s) or polypeptide portion(s) may be specified as described herein, e.g., by N-terminal and C-terminal positions, by size in contiguous amino acid residues, or listed in the Tables and Figures.

Antibodies of the present invention may also be described or specified in terms of their cross-reactivity. Antibodies that bind Notch3 polypeptides, which have at least 95%, at least 90%, at least 85%, at least 80%, at least 75%, at least 70%, at least 65%, at least 60%, at least 55%, and at least 50% identity (as calculated using methods known in the art and described herein) to Notch3 are also included in the present invention. Anti-Notch3 antibodies may also bind with a $K_D$ Of less than about $10^{-7}$ M, less than about $10^{-6}$ M, or less than about $10^{-5}$ M to other proteins, such as anti-Notch3 antibodies from species other than that against which the anti-Notch3 antibody is directed.

In specific embodiments, antibodies of the present invention cross-react with monkey homologues of human Notch3 and the corresponding epitopes thereof. In a specific embodiment, the above-described cross-reactivity is with respect to any single specific antigenic or immunogenic polypeptide, or combination(s) of the specific antigenic and/or immunogenic polypeptides disclosed herein.

Further included in the present invention are antibodies which bind polypeptides encoded by polynucleotides which hybridize to a polynucleotide encoding Notch3 under stringent hybridization conditions. Antibodies of the present invention may also be described or specified in terms of their binding affinity to a polypeptide of the invention. Preferred binding affinities include those with an equilibrium dissociation constant or $K_D$ from $10^{-8}$ to $10^{-15}$ M, $10^{-8}$ to $10^{-12}$ M, $10^{-8}$ to $10^{-10}$ M, or $10^{-10}$ to $10^{-12}$ M. The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Vectors and Host Cells

In another aspect, the present invention provides isolated nucleic acid sequences encoding an antibody as disclosed herein, vector constructs comprising a nucleotide sequence encoding the antibodies of the present invention, host cells comprising such a vector, and recombinant techniques for the production of the antibody.

For recombinant production of an antibody, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Standard techniques for cloning and transformation may be used in the preparation of cell lines expressing the antibodies of the present invention.

Vectors

Many vectors are available. The vector components generally include, but are not limited to, one or more of the following: a signal sequence, an origin of replication, one or more marker genes, an enhancer element, a promoter, and a transcription termination sequence. Recombinant expression vectors containing a nucleotide sequence encoding the antibodies of the present invention can be prepared using well known techniques. The expression vectors include a nucleotide sequence operably linked to suitable transcriptional or translational regulatory nucleotide sequences such as those derived from mammalian, microbial, viral, or insect genes. Examples of regulatory sequences include transcriptional promoters, operators, enhancers, mRNA ribosomal binding sites, and/or other appropriate sequences which control transcription and translation initiation and termination. Nucleotide sequences are "operably linked" when the regulatory sequence functionally relates to the nucleotide sequence for the appropriate polypeptide. Thus, a promoter nucleotide sequence is operably linked to, e.g., the antibody heavy chain sequence if the promoter nucleotide sequence controls the transcription of the appropriate nucleotide sequence.

In addition, sequences encoding appropriate signal peptides that are not naturally associated with antibody heavy and/or light chain sequences can be incorporated into expression vectors. For example, a nucleotide sequence for a signal peptide (secretory leader) may be fused in-frame to the polypeptide sequence so that the antibody is secreted to the periplasmic space or into the medium. A signal peptide that is functional in the intended host cells enhances extracellular secretion of the appropriate antibody. The signal peptide may be cleaved from the polypeptide upon secretion of antibody from the cell. Examples of such secretory signals are well known and include, e.g., those described in U.S. Pat. Nos. 5,698,435; 5,698,417; and 6,204,023.

The vector may be a plasmid vector, a single or double-stranded phage vector, or a single or double-stranded RNA or DNA viral vector. Such vectors may be introduced into cells as polynucleotides by well known techniques for introducing DNA and RNA into cells. The vectors, in the case of phage and viral vectors also may be introduced into cells as packaged or encapsulated virus by well known techniques for infection and transduction. Viral vectors may be replication competent or replication defective. In the latter case, viral propagation generally will occur only in complementing host cells. Cell-free translation systems may also be employed to produce the protein using RNAs derived from the present DNA constructs. Such vectors may include the nucleotide sequence encoding the constant region of the antibody molecule (see, e.g., PCT Publications WO 86/05807 and WO 89/01036; and U.S. Pat. No. 5,122,464) and the variable domain of the antibody may be cloned into such a vector for expression of the entire heavy or light chain.

Host Cells

The antibodies of the present invention can be expressed from any suitable host cell. Examples of host cells useful in the present invention include prokaryotic, yeast, or higher eukaryotic cells and include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., Baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Prokaryotes useful as host cells in the present invention include gram negative or gram positive organisms such as *E. coli, B. subtilis, Enterobacter, Erwinia, Klebsiella, Proteus, Salmonella, Serratia*, and *Shigella*, as well as Bacilli, *Pseudomonas*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the pKK223-3 vector (Pharmacia Fine Chemicals, Uppsala, Sweden), PGEM® 1 vector (Promega Biotec, Madison, Wis., USA), and the pET (Novagen, Madison, Wis., USA) and pRSET (Invitrogen, Carlsbad, Calif.) series of vectors (Studier, *J Mol Biol* 219:37 (1991); Schoepfer, *Gene* 124:83 (1993)). Promoter sequences commonly used for recombinant prokaryotic host cell expression vectors include T7, (Rosenberg, et al., *Gene* 56:125 (1987)), β-lactamase (penicillinase), lactose promoter system (Chang, et al., *Nature* 275:615 (1978); Goeddel, et al., *Nature* 281:544 (1979)), tryptophan (trp) promoter system (Goeddel, et al., *Nucl Acids Res* 8:4057 (1980)), and tac promoter (Sambrook, et al., Molecular Cloning, A Laboratory Manual, 2nd ed., Cold Spring Harbor Laboratory (1990)).

Yeasts or filamentous fungi useful in the present invention include those from the genus *Saccharomyces, Pichia, Actinomycetes, Kluyveromyces, Schizosaccharomyces, Candida, Trichoderma, Neurospora*, and filamentous fungi such as *Neurospora, Penicillium, Tolypocladium*, and *Aspergillus*. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman, et al., *J Biol Chem* 255:2073 (1980)) or other glycolytic enzymes (Holland, et al., *Biochem* 17:4900 (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer, et al., *Gene* 107:285 (1991). Other suitable promoters and vectors for yeast and yeast transformation protocols are well known in the art. Yeast transformation protocols are well known. One such protocol is described by Hinnen, et al., *Proc Natl Acad Sci* 75:1929 (1978). The Hinnen protocol selects for $Trp^+$ transformants in a selective medium.

Mammalian or insect host cell culture systems may also be employed to express recombinant antibodies. In principle, any higher eukaryotic cell culture is workable, whether from vertebrate or invertebrate culture. Examples of invertebrate cells include plant and insect cells (Luckow, et al., *Bio/Technology* 6:47 (1988); Miller, et al., Genetics Engineering, Setlow, et al., eds. Vol. 8, pp. 277-9, Plenam Publishing (1986); Mseda, et al., *Nature* 315:592 (1985)). For example, Baculovirus systems may be used for production of heterologous proteins. In an insect system,—*Autographa californica* nuclear polyhedrosis virus (AcNPV) may be used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). Other hosts that have been identified include *Aedes, Drosophila melanogaster*, and *Bombyx mori*. A variety of viral strains for transfection are publicly available, e.g., the L-1 variant of AcNPV and the Bm-5 strain of *Bombyx mori* NPV, and such viruses may be used as the virus herein according to the present invention, particularly for transfection of *Spodoptera frugiperda* cells. Moreover, plant cells cultures of cotton, corn, potato, soybean, petunia, tomato, and tobacco and also be utilized as hosts.

Vertebrate cells, and propagation of vertebrate cells, in culture (tissue culture) has become a routine procedure. See Tissue Culture, Kruse, et al., eds., Academic Press (1973). Examples of useful mammalian host cell lines are monkey kidney; human embryonic kidney line; baby hamster kidney cells; Chinese hamster ovary cells/−DHFR (CHO, Urlaub, et al., *Proc Natl Acad Sci USA* 77:4216 (1980)); mouse sertoli cells; human cervical carcinoma cells (HELA); canine kidney cells; human lung cells; human liver cells; mouse mammary tumor; and NSO cells.

Host cells are transformed with the above-described vectors for antibody production and cultured in conventional nutrient media modified as appropriate for inducing promoters, transcriptional and translational control sequences, selecting transformants, or amplifying the genes encoding the desired sequences. Commonly used promoter sequences and enhancer sequences are derived from polyoma virus, Adenovirus 2, Simian virus 40 (SV40), and human cytomegalovirus (CMV). DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are commercially available.

The host cells used to produce the antibody variant of this invention may be cultured in a variety of media. Commercially available media such as Ham's F10 (Sigma, St Louis, Mo.), Minimal Essential Medium (MEM, Sigma, St Louis, Mo.), RPMI-1640 (Sigma, St Louis, Mo.), and Dulbecco's Modified Eagle's Medium (DMEM, Sigma, St Louis, Mo.) are suitable for culturing host cells. In addition, any of the media described in Ham, et al., *Meth Enzymol* 58:44 (1979), Barnes, et al., *Anal Biochem* 102:255 (1980), and U.S. Pat. Nos. 4,767,704; 4,657,866; 4,560,655; 5,122,469; 5,712,163; or 6,048,728 may be used as culture media for the host cells. Any of these media may be supplemented as necessary with hormones and/or other growth factors (such as insulin, transferrin, or epidermal growth factor), salts (such as X-chlorides, where X is sodium, calcium, magnesium; and phosphates), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Polynucleotides Encoding Antibodies

The invention further provides polynucleotides or nucleic acids, e.g., DNA, comprising a nucleotide sequence encoding an antibody of the invention and fragments thereof. Exemplary polynucleotides include those encoding antibody chains comprising one or more of the amino acid sequences described herein. The invention also encompasses polynucleotides that hybridize under stringent or lower stringency hybridization conditions to polynucleotides that encode an antibody of the present invention.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier, et al., *Bio/Techniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly $A^+$ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook, et al., Molecular Cloning, A Laboratory Manual, 2nd ed., Cold Spring Harbor Laboratory (1990); Ausubel, et al., eds., Current Protocols in Molecular Biology, John Wiley & Sons (1998), which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the CDRs by well known methods, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia, et al., *J Mol Biol* 278: 457 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison, et al., *Proc Natl Acad Sci* 81:851 (1984); Neuberger, et al., *Nature* 312:604 (1984); Takeda, et al., *Nature* 314:452 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, *Science* 242:423 (1988); Huston, et al., *Proc Natl Acad Sci USA* 85:5879 (1988); and Ward, et al., *Nature* 334:544 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra, et al., *Science* 242:1038 (1988)).

Methods of Producing Anti-Notch3 Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative, or analog thereof, (e.g., a heavy or light chain of an antibody of the invention or a single chain antibody of the invention), requires construction of an expression vector containing a polynucleotide that encodes the antibody or a fragment of the antibody. Once a polynucleotide encoding an antibody molecule has been obtained, the vector for the production of the antibody may be produced by recombinant DNA technology. An expression vector is constructed containing antibody coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce an antibody of the invention. In one aspect of the invention, vectors encoding both the heavy and light chains may be co-expressed in the host cell for expression of the entire immunoglobulin molecule, as detailed below.

A variety of host-expression vector systems may be utilized to express the antibody molecules of the invention as described above. Such host-expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells such as *E. coli*, and eukaryotic cells are commonly used for the expression of a recombinant antibody molecule, especially for the expression of whole recombinant antibody molecule. For example, mammalian cells such as CHO, in conjunction with a vector such as the major intermediate early gene promoter element from human cytomegalovirus, are an effective expression system for antibodies (Foecking, et al., *Gene* 45:101 (1986); Cockett, et al., *Bio/Technology* 8:2 (1990)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, COS, 293, 3T3, or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for one to two days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler, et al., *Cell* 11:223 (1977)), hypoxanthine-guanine phosphoribosyltransferase (Szybalska, et al., *Proc Natl Acad Sci USA* 48:202 (1992)), and adenine phosphoribosyltransferase (Lowy, et al., *Cell* 22:817 (1980)) genes can be employed in tk, hgprt or aprt-cells, respectively. Also, antimetabolite resistance can be used as the basis of selection for the following genes: dhfr, which confers resistance to methotrexate (Wigler, et al., *Proc Natl Acad Sci USA* 77:357 (1980); O'Hare, et al., *Proc Natl Acad Sci USA* 78:1527 (1981)); gpt, which confers resistance to mycophenolic acid (Mulligan, et al., *Proc Natl Acad Sci USA* 78:2072 (1981)); neo, which confers resistance to the aminoglycoside G-418 (Wu, et al., *Biotherapy* 3:87 (1991)); and hygro, which confers resistance to hygromycin (Santerre, et al., *Gene* 30:147 (1984)). Methods commonly known in the art of recombinant DNA technology may be routinely applied to select the desired recombinant clone, and such methods are described, for example, in Ausubel, et al., eds., Current Protocols in Molecular Biology, John Wiley & Sons (1993); Kriegler, Gene Transfer and Expression, A Laboratory Manual, Stockton Press (1990); and in Chapters 12 and 13, Dracopoli, et al., eds, Current Protocols in Human Genetics, John Wiley & Sons (1994); Colberre-Garapin, et al., *J Mol Biol* 150:1 (1981), which are incorporated by reference herein in their entireties.

The expression levels of an antibody molecule can be increased by vector amplification (for a review, see Bebbington, et al., "The use of vectors based on gene amplification for the expression of cloned genes in mammalian cells," DNA Cloning, Vol. 3. Academic Press (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse, et al., *Mol Cell Biol* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature* 322:52 (1986); Kohler, *Proc Natl Acad Sci USA* 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and size-exclusion chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide. Fused or conjugated antibodies of the present invention may be used for ease in purification. See e.g., PCT publication WO 93/21232; EP 439,095; Naramura, et al., *Immunol Lett* 39:91 (1994); U.S. Pat. No. 5,474,981; Gillies, et al., *Proc Natl Acad Sci USA* 89:1428 (1992); Fell, et al., *J Immunol* 146:2446 (1991), which are incorporated by reference in their entireties.

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., Valencia, Calif.), among others, many of which are commercially available. As described in Gentz, et al., *Proc Natl Acad Sci USA* 86:821 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson, et al., *Cell* 37:767 (1984)) and the "flag" tag.

Antibody Purification

When using recombinant techniques, an antibody can be produced intracellularly, in the periplasmic space, or directly secreted into the medium. If the antibody is produced intracellularly, as a first step, the particulate debris, either host cells or lysed fragments, may be removed, for example, by centrifugation or ultrafiltration. Carter, et al., *Bio/Technology* 10:163 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody variant. Protein A can be used to purify antibodies that are based on human IgG1, IgG2 or IgG4 heavy chains (Lindmark, et al., *J Immunol Meth* 62:1 (1983)). Protein G is recommended for all mouse isotypes and for human IgG3 (Guss, et al., *EMBO J.* 5:1567 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody variant comprises a CH3 domain, the Bakerbond ABX™ resin (J. T. Baker; Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE® chromatography on an anion or cation exchange resin (such as a polyaspartic acid column), chromatofocusing, SDS-PAGE, and ammonium sulfate precipitation are also available depending on the antibody variant to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulation

Therapeutic formulations of the polypeptide or antibody may be prepared for storage as lyophilized formulations or aqueous solutions by mixing the polypeptide having the desired degree of purity with optional "pharmaceutically-acceptable" carriers, excipients or stabilizers typically employed in the art (all of which are termed "excipients"), i.e., buffering agents, stabilizing agents, preservatives, isotonifiers, non-ionic detergents, antioxidants, and other miscellaneous additives. See Remington's Pharmaceutical Sciences, 16th edition, Osol, Ed. (1980). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives may be added to retard microbial growth, and may be added in amounts ranging from 0.2%-1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, and alkyl parabens such as methyl or propyl paraben, catechol, resorcinol, cyclohexanol, and 3-pentanol.

Isotonicifiers sometimes known as "stabilizers" may be added to ensure isotonicity of liquid compositions of the present invention and include polhydric sugar alcohols, preferably trihydric or higher sugar alcohols, such as glycerin, erythritol, arabitol, xylitol, sorbitol and mannitol.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc.; organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, alpha.-monothioglycerol and sodium thio sulfate; low molecular weight polypeptides (i.e. <10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers may be present in the range from 0.1 to 10,000 weights per part of weight active protein.

Non-ionic surfactants or detergents (also known as "wetting agents") may be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), PLURONIC® polyols, polyoxyethylene sorbitan monoethers (TWEEN-20®, TWEEN-80®, etc.). Non-ionic surfactants may be present in a range of about 0.05 mg/ml to about 1.0 mg/ml, preferably about 0.07 mg/ml to about 0.2 mg/ml.

Additional miscellaneous excipients include bulking agents, (e.g., starch), chelating agents (e.g., EDTA), antioxidants (e.g., ascorbic acid, methionine, vitamin E), and cosolvents. The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended. The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin micropheres, microemulsions, nano-particles and nanocapsules) or in macroemulsions. Such techniques are disclosed in Remington's Pharmaceutical Sciences, 16th edition, Osal, Ed. (1980).

The formulations to be used for in vivo administration should be sterile. This is readily accomplished, for example, by filtration through sterile filtration membranes. Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of therapeutic polypeptide, antibody, or fragment thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans.

In a preferred embodiment, an aqueous solution of therapeutic polypeptide, antibody or fragment thereof is administered by subcutaneous injection. Each dose may range from about 0.5 μg to about 50 μg per kilogram of body weight, or more preferably, from about 3 μg to about 30 μg per kilogram body weight.

The dosing schedule for subcutaneous administration may vary from once a month to daily depending on a number of clinical factors, including the type of disease, severity of disease, and the subject's sensitivity to the therapeutic agent.

Therapeutic Uses of Anti-Notch-3 Antibodies

It is contemplated that the antibodies of the present invention may be used to treat a mammal. In one embodiment, the antibody is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed on the mammal.

An antibody, with or without a therapeutic moiety conjugated to it, administered alone or in combination with cytotoxic factor(s) can be used as a therapeutic. The present invention is directed to antibody-based therapies which involve administering antibodies of the invention to an animal, a mammal, or a human, for treating a Notch3-mediated disease, disorder, or condition. The animal or subject may be a mammal in need of a particular treatment, such as a mammal having been diagnosed with a particular disorder, e.g., one relating to Notch3. Antibodies directed against Notch3 are useful against cancer and other Notch3-associated diseases including neurological disorders, diabetes, rheumatoid arthritis, vascular related diseases, and Alagille symdrome in mammals, including but not limited to cows, pigs, horses, chickens, cats, dogs, non-human primates etc., as well as humans. For example, by administering a therapeutically acceptable dose of an anti-Notch3 antibody, or antibodies, of the present invention, or a cocktail of the present antibodies, or in combination with other antibodies of varying sources, disease symptoms may be ameliorated or prevented in the treated mammal, particularly humans.

Therapeutic compounds of the invention include, but are not limited to, antibodies of the invention (including fragments, analogs and derivatives thereof as described herein) and nucleic acids encoding antibodies of the invention as described below (including fragments, analogs and derivatives thereof and anti-idiotypic antibodies as described herein). The antibodies of the invention can be used to treat, inhibit, or prevent diseases, disorders, or conditions associated with aberrant expression and/or activity of Notch3, including, but not limited to, any one or more of the diseases, disorders, or conditions described herein. The treatment and/or prevention of diseases, disorders, or conditions associated with aberrant expression and/or activity of Notch3 includes, but is not limited to, alleviating at least one symptom associated with those diseases, disorders, or conditions. Antibodies of the invention may be provided in pharmaceutically acceptable compositions as known in the art or as described herein.

Anti-Notch3 antibodies of the present invention may be used therapeutically in a variety of diseases. The present invention provides a method for preventing or treating Notch3-mediated diseases in a mammal. The method comprises administering a disease preventing or treating amount of anti-Notch3 antibody to the mammal. The anti-Notch3 antibody binds to Notch3 and antagonizes its function. Notch3 signaling has been linked to various diseases such as various cancers (Haruki, et al., *Cancer Res* 65:3555 (2005); Park, et al., *Cancer Res* 66:6312 (2006); Lu, et al., *Clin Cancer Res* 10:3291 (2004)); Hedvat, et al., *Br J Haematol* 122:728 (2003); Buchler, et al., *Ann Surg* 242:791 (2005)); Bellavia, et al., *Proc Natl Acad Sci USA* 99:3788 (2002);

Screpanti, et al., *Trends Mol Med* 9:30 (2003)); van Limpt, et al., *Cancer Lett* 228:59 (2005)), neurological disorders (Joutel, et al., *Nature* 383:707 (1996)), diabetes (Anastasi, et al., *J Immunol* 171:4504 (2003), rheumatoid arthritis (Yabe, et al., *J Orthop Sci* 10:589 (2005)), vascular related diseases (Sweeney, et al., *FASEB J* 18:1421 (2004)), and Alagille syndrome (Flynn, et al., *J Pathol* 204:55 (2004)). Anti-Notch3 antibodies will also be effective to prevent the above mentioned diseases.

The amount of the antibody which will be effective in the treatment, inhibition, and prevention of a disease or disorder associated with aberrant expression and/or activity of Notch3 can be determined by standard clinical techniques. The dosage will depend on the type of disease to be treated, the severity and course of the disease, whether the antibody is administered for preventive or therapeutic purposes, previous therapy, the patient's clinical history and response to the antibody, and the discretion of the attending physician. The antibody can be administered in treatment regimes consistent with the disease, e.g., a single or a few doses over one to several days to ameliorate a disease state or periodic doses over an extended time to inhibit disease progression and prevent disease recurrence. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 150 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat a disease or disorder. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages.

The antibodies of the invention may be administered alone or in combination with other types of cancer treatments including conventional chemotherapeutic agents (paclitaxel, carboplatin, cisplatin and doxorbicin), anti-EGFR agents (gefitinib, erlotinib and cetuximab), anti-angiogenesis agents (bevacizumab and sunitinib), as well as immuno-modulating agents such as interferon-α and thalidomide.

In a preferred aspect, the antibody is substantially purified (e.g., substantially free from substances that limit its effect or produce undesired side-effects).

Various delivery systems are known and can be used to administer an antibody of the present invention, including injection, e.g., encapsulation in liposomes, microparticles, microcapsules, recombinant cells capable of expressing the compound, receptor-mediated endocytosis (see, e.g., Wu, et al., *J Biol Chem* 262:4429 (1987)), construction of a nucleic acid as part of a retroviral or other vector, etc.

The anti-Notch3 antibody can be administered to the mammal in any acceptable manner. Methods of introduction include but are not limited to parenteral, subcutaneous, intraperitoneal, intrapulmonary, intranasal, epidural, inhalation, and oral routes, and if desired for immunosuppressive treatment, intralesional administration. Parenteral infusions include intramuscular, intradermal, intravenous, intraarterial, or intraperitoneal administration. The antibodies or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the therapeutic antibodies or compositions of the invention into the central nervous system by any suitable route, including intraventricular and intrathecal injection; intraventricular injection may be facilitated by an intraventricular catheter, for example, attached to a reservoir, such as an Ommaya reservoir. In addition, the antibody is suitably administered by pulse infusion, particularly with declining doses of the antibody. Preferably the dosing is given by injections, most preferably intravenous or subcutaneous injections, depending in part on whether the administration is brief or chronic.

Pulmonary administration can also be employed, e.g., by use of an inhaler or nebulizer, and formulation with an aerosolizing agent. The antibody may also be administered into the lungs of a patient in the form of a dry powder composition (See e.g., U.S. Pat. No. 6,514,496).

In a specific embodiment, it may be desirable to administer the therapeutic antibodies or compositions of the invention locally to the area in need of treatment; this may be achieved by, for example, and not by way of limitation, local infusion, topical application, by injection, by means of a catheter, by means of a suppository, or by means of an implant, said implant being of a porous, non-porous, or gelatinous material, including membranes, such as sialastic membranes, or fibers. Preferably, when administering an antibody of the invention, care must be taken to use materials to which the protein does not absorb.

In another embodiment, the antibody can be delivered in a vesicle, in particular a liposome (see Langer, *Science* 249:1527 (1990); Treat, et al., in Liposomes in the Therapy of Infectious Disease and Cancer, Lopez-Berestein, et al., eds., pp. 353-365 (1989); Lopez-Berestein, ibid., pp. 317-27; see generally ibid.).

In yet another embodiment, the antibody can be delivered in a controlled release system. In one embodiment, a pump may be used (see Langer, *Science* 249:1527 (1990); Sefton, *CRC Crit Ref Biomed Eng* 14:201 (1987); Buchwald, et al., *Surgery* 88:507 (1980); Saudek, et al., *N Engl J Med* 321:574 (1989)). In another embodiment, polymeric materials can be used (see Medical Applications of Controlled Release, Langer, et al., eds., CRC Press (1974); Controlled Drug Bioavailability, Drug Product Design and Performance, Smolen, et al., eds., Wiley (1984); Ranger, et al., *J Macromol Sci Rev Macromol Chem* 23:61 (1983); see also Levy, et al., *Science* 228:190 (1985); During, et al., *Ann Neurol* 25:351 (1989); Howard, et al., *J Neurosurg* 71:105 (1989)). In yet another embodiment, a controlled release system can be placed in proximity of the therapeutic target.

The present invention also provides pharmaceutical compositions. Such compositions comprise a therapeutically effective amount of the antibody and a physiologically acceptable carrier. In a specific embodiment, the term "physiologically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such physiological carriers can be sterile liquids, such as water and oils, including those of petroleum, animal, vegetable, or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable carriers are described in "Remington's Pharmaceutical Sciences" by E. W. Martin. Such compositions will contain an effective amount of the antibody, preferably in purified form, together with a suitable amount of carrier so as to provide the form for proper administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In addition, the antibodies of the present invention may be conjugated to various effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387. An antibody or fragment thereof may be conjugated to a therapeutic moiety such as a cytotoxin (e.g., a cytostatic or cytocidal agent), a therapeutic agent, or a radioactive metal ion (e.g., alpha-emitters such as, for example, 213Bi). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques for conjugating such therapeutic moieties to antibodies are well known, see, e.g., Amon, et al., "Monoclonal Antibodies For Immunotargeting Of Drugs In Cancer Therapy", in Monoclonal Antibodies and Cancer Therapy, Reisfeld, et al. (eds.), pp. 243-56 Alan R. Liss (1985); Hellstrom, et al., "Antibodies For Drug Delivery", in Controlled Drug Delivery, 2nd ed., Robinson, et al., eds., pp. 623-53, Marcel Dekker (1987); Thorpe, "Antibody Carriers Of Cytotoxic Agents In Cancer Therapy: A Review," in Monoclonal Antibodies '84: Biological And Clinical Applications, Pinchera, et al., eds., pp. 475-506 (1985); "Analysis, Results, And Future Prospective Of The Therapeutic Use Of Radiolabeled Antibody In Cancer Therapy," in Monoclonal Antibodies For Cancer Detection and Therapy, Baldwin, et al., eds., pp. 303-16, Academic Press (1985); and Thorpe, et al., *Immunol Rev* 62:119 (1982). Alternatively, an antibody can be conjugated to a second antibody to form an antibody heteroconjugate. See, e.g., U.S. Pat. No. 4,676,980.

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (See, International Publication No. WO 97/33899), AIM II (See, International Publication No. WO 97/34911), Fas Ligand (Takahashi, et al., *Int Immunol,* 6:1567 (1994)), VEGI (See, International Publication No. WO 99/23105); a thrombotic agent; an anti-angiogenic agent, e.g., angiostatin or endostatin; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for preventing or treating the condition and may have a sterile access port (for example, the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

Antibody-Based Gene Therapy

In a another aspect of the invention, nucleic acids comprising sequences encoding antibodies or functional derivatives thereof, are administered to treat, inhibit or prevent a disease or disorder associated with aberrant expression and/or activity of Notch3, by way of gene therapy. Gene therapy refers to therapy performed by the administration to a subject of an expressed or expressible nucleic acid. In this embodiment of the invention, the nucleic acids produce their encoded protein that mediates a therapeutic effect. Any of the methods for gene therapy available can be used according to the present invention. Exemplary methods are described below.

For general reviews of the methods of gene therapy, see Goldspiel, et al., *Clinical Pharmacy* 12:488 (1993); Wu, et al., *Biotherapy* 3:87 (1991); Tolstoshev, *Ann Rev Pharmacol Toxicol* 32:573 (1993); Mulligan, *Science* 260:926 (1993); Morgan, et al., *Ann Rev Biochem* 62:191 (1993); May, *TIBTECH* 11:155 (1993).

In a one aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific.

In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller, et al., *Proc Natl Acad Sci USA* 86:8932 (1989); Zijlstra, et al., *Nature* 342:435 (1989)). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu, et al., *J Biol Chem* 262:4429 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller, et al., *Proc Natl Acad Sci USA* 86:8932 (1989); Zijlstra, et al., *Nature* 342:435 (1989)).

In a specific embodiment, viral vectors that contain nucleic acid sequences encoding an antibody of the invention are used. For example, a retroviral vector can be used (see Miller, et al., *Meth Enzymol* 217:581 (1993)). These retroviral vectors contain the components necessary for the correct packaging of the viral genome and integration into the host cell DNA. The nucleic acid sequences encoding the antibody to be used in gene therapy are cloned into one or more vectors, which facilitate the delivery of the gene into a patient. More detail about retroviral vectors can be found in Boesen, et al., *Biotherapy* 6:291 (1994), which describes the use of a retroviral vector to deliver the mdrI gene to hematopoietic stem cells in order to make the stem cells more resistant to chemotherapy. Other references illustrating the use of retroviral vectors in gene therapy are: Clowes, et al., *J Clin Invest* 93:644 (1994); Kiem, et al., *Blood* 83:1467 (1994); Salmons, et al., *Human Gene Therapy* 4:129 (1993); and Grossman, et al., *Curr Opin Gen and Dev* 3:110 (1993).

Adenoviruses may also be used in the present invention. Adenoviruses are especially attractive vehicles in the present invention for delivering antibodies to respiratory epithelia. Adenoviruses naturally infect respiratory epithelia. Other targets for adenovirus-based delivery systems are liver, the central nervous system, endothelial cells, and muscle. Adenoviruses have the advantage of being capable of infecting non-dividing cells. Kozarsky, et al., *Curr Opin Gen Dev* 3:499

(1993) present a review of adenovirus-based gene therapy. Bout, et al., *Human Gene Therapy* 5:3 (1994) demonstrated the use of adenovirus vectors to transfer genes to the respiratory epithelia of rhesus monkeys. Other instances of the use of adenoviruses in gene therapy can be found in Rosenfeld, et al., *Science* 252:431 (1991); Rosenfeld, et al., *Cell* 68:143 (1992); Mastrangeli, et al., *J Clin Invest* 91:225 (1993); PCT Publication WO94/12649; Wang, et al., *Gene Therapy* 2:775 (1995). Adeno-associated virus (AAV) has also been proposed for use in gene therapy (Walsh, et al., *Proc Soc Exp Biol Med* 204:289 (1993); U.S. Pat. Nos. 5,436,146; 6,632,670; and 6,642,051).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler, et al., *Meth Enzymol* 217:599 (1993); Cohen, et al., *Meth Enzymol* 217:618 (1993); Cline, *Pharmac Ther* 29:69 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In one embodiment, the cell used for gene therapy is autologous to the patient. Nucleic acid sequences encoding an antibody of the present invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple, et al., *Cell* 71:973 (1992); Rheinwald, *Meth Cell Bio* 21A:229 (1980); Pittelkow, et al., *Mayo Clinic Proc* 61:771 (1986)).

EXAMPLES

Example 1

Generation of Immunogen: Notch3 Extracellular Domain-Fc Fusion Protein

Anti-Notch3 monoclonal antibodies that specifically bind to the LIN12/dimerization domain (herein after "LD") of human Notch3 were generated using a recombinant Notch3-Fc fusion protein as immunogen comprising Notch3 LD fused to a gamma 1 Fc region at the carboxy terminal end. Specifically, the immunogen comprised amino acid residues 1378 to 1640 of Notch3 LD (See FIG. 1) and human γ1Fc fusion protein (Notch3 LD/Fc). A control antibody was generated comprising the Notch3 EGF repeat region from amino acid residues 43 to 1377 (designated 255A-79).

Notch3 protein sequence was analyzed using an internet-based research software and service (Motif Search). Human liver and pancreatic RNAs (Ambion, Inc. Austin, Tex.) were used as templates to synthesize the first strand of cDNA using a standard commercially available cDNA synthesis kit. The cDNAs encoding the Notch3 LD and the EGF repeat region were PCR-amplified in the presence of Betaine (1-2M) and DMSO (5%). The PCR-synthesized Notch3-LD DNA fragment (~0.8 kb) and Notch3-EGF repeat DNA fragment (~4 kb) were cloned into expression vectors comprising a His-γ1Fc in the commercially available vector pSec or in the commercially available vector pCD3.1, each bearing a different antibiotic marker. This cloning resulted in two expression plasmids, one expressing a Notch3-LD/Fc fusion protein and the other expressing a Notch3-EGF/Fc fusion protein.

Figure 15:
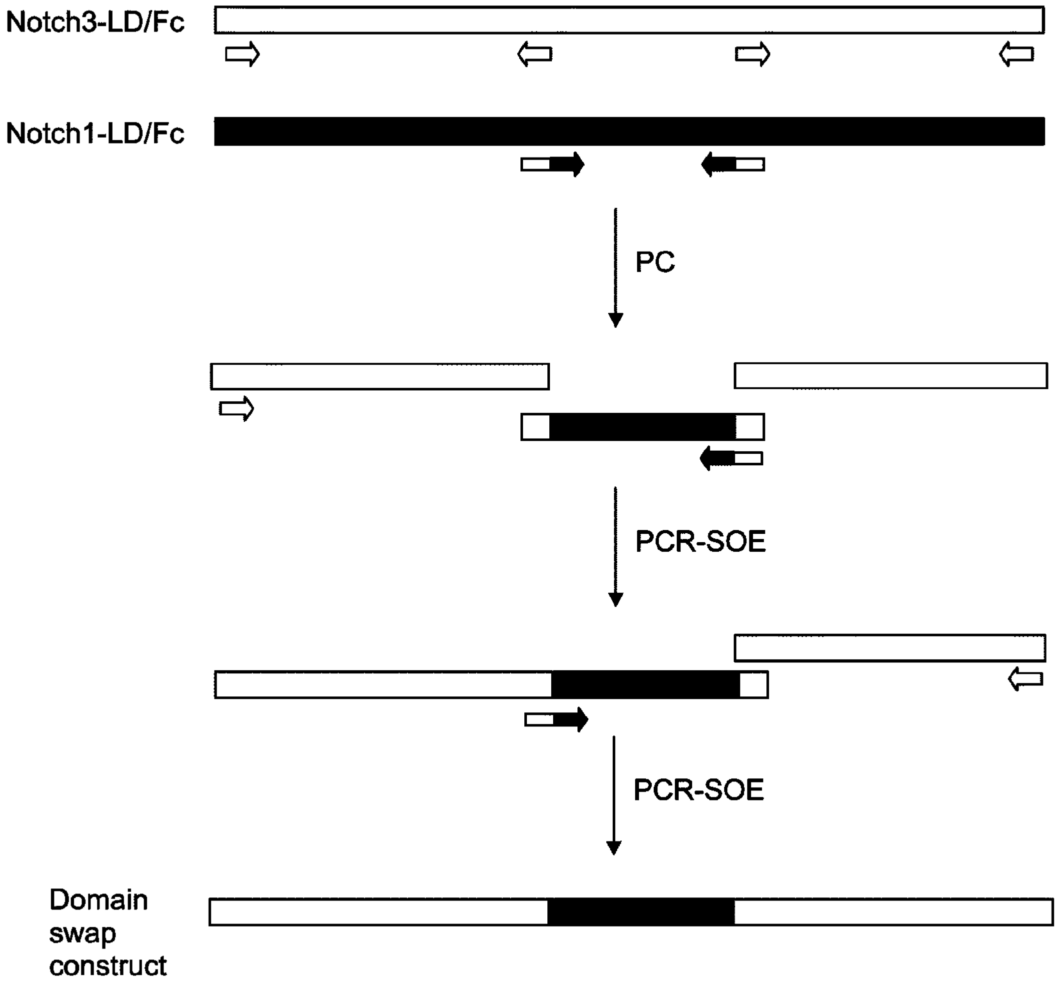
FIG. 15 depicts the generation of domain swap construct by PCR-SOE method. Arrow bars represent PCR primers. Open bar, Notch3 sequence. Filled bar, Notch1 sequence.

To facilitate the plasmid construction and to enhance the expression of the various Notch 3 recombinant proteins, oligonucleotides corresponding to the leader peptide sequence comprising the first 135 base pairs of the Notch3 nucleic acid coding sequence were generated. These oligonucleotides contained some changes in the wobble coding positions to lower the GC content. All nucleotide sequence changes were silent, i.e., no amino acid sequence changes (FIG. 14A). After annealing the oligonucleotides together, the engineered leader peptide coding sequence was linked to the rest of the coding sequence by PCR-SOE (Ho, et al., *Gene* 77:51 (1989); Horton, et al., *BioTechniques* 8:528 (1990)) (See FIG. 15). This leader peptide coding sequence was used in Notch3-LD/Fc and Notch3 expression constructs. Therefore, both of the Fc fusion proteins comprise a signal peptide linked to the N-terminus, and a human γ1Fc sequence fused to the C-terminus. The amino acid sequence of Notch3-LD, including the leader peptide, is shown in FIG. 14 and SEQ ID NO:6.

Expression of Notch3-EGF/Fc and Notch3-LD/Fc fusion proteins were verified by transient transfection of the Notch3 expression plasmids into 293T (ATCC Number CRL-11268, Manassas, Va.) and CHO cells (Invitrogen, Carlsbad, Calif.), respectively. Prior to transfection, cells were cultured in DMEM (Invitrogen, Carlsbad, Calif.) growth medium containing 10% fetal calf serum (FCS), 2 mM of glutamine, and 1× essential amino acid solution followed by seeding about $3\text{-}5\times10^5$ cells per well in 6-well plate and growing for approximately 24 hours. Three micrograms each of the Notch3 fusion protein expression plasmids were transfected into cells in each well using a LIPOFECTAMINE™ 2000 transfection system (Invitrogen, Carlsbad, Calif.) following the manufacturer's protocol. After transfection, the cells were cultured in fresh growth medium and cultured in a $CO_2$ incubator for approximately 40-48 hours before subjecting to Notch3 fusion protein expression analysis. Alternatively, after transfection, the cells were cultured in growth medium for 3-4 hours, then switched to DMEM medium containing 2% FCS and cultured for approximately 60-66 hours before drawing conditioned medium for secreted protein analysis.

Stable cell lines were generated for both Notch3-LD/Fc (His-Fcγ/pSec vector) and Notch3-EGF/Fc (His-Fcγ/pSec vector). Each plasmid was transfected into CHO cells. After transfection, the cells were cultured in DMEM growth medium overnight, then switched to growth medium with 800 μg/ml hygromycin and cultured at least two weeks until the cells not carrying Notch3 expression plasmid were eliminated by the antibiotics. Conditioned media from the stable cell lines were subjected to Western blot analysis.

Stable or transient transfected cells were assayed for expression and secretion of Notch3-LD/Fc or Notch3-EGF/Fc fusion protein. Transfected cells harvested from culture dishes were washed once with phosphate buffered saline (PBS) and resuspended in deionized water, mixed with an equal volume of 2× protein sample loading buffer (BioRad, Hercules, Calif.) and then heated at about 100° C. for 10 minutes. Secreted protein was analyzed using conditioned medium mixed with an equal volume of 2× protein sample loading buffer and heated at 100° C. for 10 minutes. The samples were separated using 4-15% gradient SDS-PAGE. The proteins were transferred from the gel to a PVDF membrane (BioRad, Hercules, Calif.), which was blocked in 5% non-fat dry milk in PBST (PBS with 0.05% TWEEN-20®) for at least one hour prior to transfer of protein.

Notch3-EGF/Fc and Notch3-LD/Fc fusion proteins were detected by incubating with γFc-specific, HRP-conjugated antibody (Sigma, St Louis, Mo.) in blocking buffer for one hour at room temperature. The membrane was washed three times in PBST and developed with a chemiluminescent substrate.

For Notch3 domain/Fc fusion protein purification, CHO stable cell lines as described above were cultured in DMEM with 2% FCS for up to 5 days. One liter of conditioned medium was collected and subjected to protein-A bead-packed column chromatography for affinity binding. The column was washed with PBS, and the bound proteins were eluted in 50 mM citrate buffer (pH 2.8), and the pH was brought to neutral by adding 1 M Tris-HCl buffer (pH 8). Purity of the protein was assessed by protein gel analysis using 4-15% gradient SDS-PAGE. Protein concentration was assayed using Coomassie blue reagent following the manufacturer's protocol (Pierce, Rockford, Ill.). Through this procedure, milligram quantities of Notch3-LD/Fc and Notch3-EGF/Fc protein were purified for immunization and ELISA binding assays.

Example 2

Generation of Anti-Notch3 MAbs

Male A/J mice (Harlan, Houston, Tex.), 8-12 weeks old, were injected subcutaneously with 25 μg of Notch3-EGF/Fc or Notch3-LD/Fc in complete Freund's adjuvant (Difco Laboratories, Detroit, Mich.) in 200 μl of PBS. Two weeks after the injections and three days prior to sacrifice, the mice were again injected intraperitoneally with 25 μg of the same antigen in PBS. For each fusion, single cell suspensions were prepared from spleen of an immunized mouse and used for fusion with Sp2/0 myeloma cells; $5\times10^8$ of Sp2/0 and $5\times10^8$ of spleen cells were fused in a medium containing 50% polyethylene glycol (M.W. 1450) (Kodak, Rochester, N.Y.) and 5% dimethylsulfoxide (Sigma, St. Louis, Mo.). The cells were then adjusted to a concentration of $1.5\times10^5$ spleen cells per 200 μl of the suspension in Iscove medium (Invitrogen, Carlsbad, Calif.), supplemented with 10% fetal bovine serum, 100 units/ml of penicillin, 100 μg/ml of streptomycin, 0.1 μM hypoxanthine, 0.4 μM aminopterin, and 16 μM thymidine. Two hundred microliters of the cell suspension were added to each well of about sixty 96-well plates. After around ten days, culture supernatants were withdrawn for screening their antibody-binding activity using ELISA.

The 96-well flat bottom IMMULON® II microtest plates (Dynatech, Laboratories, Chantilly, Va.) were coated using 100 μl of Notch3-EGF/Fc or Notch3-LD/Fc (0.1 μg/ml) in (PBS) containing 1× Phenol Red and 3-4 drops pHix/liter (Pierce, Rockford, Ill.) and incubated overnight at room temperature. After the coating solution was removed by flicking of the plate, 200 μl of blocking buffer containing 2% BSA in PBST containing 0.1% merthiolate was added to each well for one hour to block non-specific binding. The wells were then washed with PBST. Fifty microliters of culture supernatant from each fusion well was collected and mixed with 50 μl of blocking buffer and then added to the individual wells of the microtiter plates. After one hour of incubation, the wells were washed with PBST. The bound murine antibodies were then detected by reaction with horseradish peroxidase (HRP)-conjugated, Fc-specific goat anti-mouse IgG (Jackson ImmunoResearch Laboratories, West Grove, Pa.). HRP substrate solution containing 0.1% 3,3,5,5-tetramethyl benzidine and 0.0003% hydrogen peroxide was added to the wells for color development for 30 minutes. The reaction was terminated by the addition of 50 ml of 2 M $H_2SO_4$/well. The OD at 450 nm was read with an ELISA plate reader (Molecular Devices, Sunnyvale, Calif.).

Among 185 hybridomas isolated and analyzed, two hybridoma clones from mice immunized with Notch3-LD/Fc generated Notch3 antagonizing antibodies, which were further characterized. The ELISA using supernatant from the two hybridoma clones producing MAbs 256A-4 and 256A-8 showed strong binding activity to the purified Notch3 LD/FC fusion protein to which it was generated and did not bind to human Notch1-LD/Fc (LIN/dimerization domain fused to Fc region at the carboxyl terminus) or a control human Fc protein (data not shown) (Table 1). Later studies using functional assays also demonstrated that MAbs 256A-4 and 256A-8 specifically antagonize Notch3 relative to Notch1 and Notch2 (data not shown).

TABLE 1

ELISA OD readings of anti-Notch3 Mabs using hybridoma supernatant

| | Notch3-LD/Fc | | Notch1-LD/Fc | |
|---|---|---|---|---|
| | Mean | S.D. | Mean | S.D. |
| 256A-4 | 4.000 | 0.000 | 0.106 | 0.004 |
| 256A-8 | 4.000 | 0.000 | 0.115 | 0.014 |
| Control IgG1* | 0.064 | 0.006 | 0.066 | 0.006 |

*Control IgG was an irrelevant IgG1 monoclonal antibody.

The positive hybridoma clones from this primary ELISA screening were further isolated by single colony-picking and a second ELISA assay as described above was done to verify specific binding to the chosen immunogen. The confirmed hybridoma clones were expanded in larger scale cultures. The monoclonal antibodies (MAbs) were purified from the medium of these large scale cultures using a protein A affinity column. The anti-Notch3 MAbs were then characterized using cell-based binding assays, microscopy, Western blot, and FACS analysis.

Example 3

Cell-Based Binding Assays for Anti-Notch3 MAbs

The cell-based binding assays used to characterize the anti-Notch3 MAbs required cloning a full-length of human Notch3 open reading frame into a vector, in this case PCDNA™ 3.1/Hygro (Invitrogen, Carlsbad, Calif.). The Notch3-coding region was synthesized by RT-PCR using human liver tumor RNA (Ambion, Inc., Austin, Tex.) as a template. The final plasmid construct, Notch3/Hygro, expressed a full-length Notch3 protein as depicted in FIG. 1. A stable cell line expressing Notch3 was generated by transfection of Notch3/Hygro plasmid construct into 293T cells (ATCC No. CRL-11268) using a LIPOFECTAMINE™ 2000 kit following the same procedure as described in Example 1. After transfection, the cells were cultured in DMEM growth medium overnight, then reseeded in growth medium with 200 μg/ml hygromycin and cultured for 12-14 days. Well-isolated single colonies were picked and grown in separate wells until enough clonal cells were amplified. Stable 293T clones that were resistant to hygromycin selection and expressed high levels of Notch3 protein were identified by Western blot analysis, and by fluorescent electromicroscopy using polyclonal anti-Notch3 antibodies (R&D Systems, Minneapolis, Minn.).

A partial Notch3 expression plasmid containing only the Notch LIN12/dimerization (LD) domain and the transmembrane (TM) domain was also constructed by PCR and subcloned into PCDNA™ 3.1 vector (Invitrogen, Carlsbad, Calif.). This plasmid construct also contains a V5 tag at its C-terminus and was termed Notch3-LDTM/V5. A stable cell line expressing this plasmid, Notch3-LDTM/V5, was generated according to the procedure described in Example 1.

Human Sup-T1 cell line (ATCC No. CRL-1942) naturally expressing Notch3 was also confirmed by Western blot. Sup-T1 cells were grown in RPMI1640 media containing 10% fetal calf serum, 2 mM of glutamine and 1× essential amino acid solution.

Cell-based antibody-binding was assessed using FMAT™ (fluorescence macro-confocal high-throughput screening) 8100 HTS System (Applied Biosystems, Foster City, Calif.) following the protocol provided by the manufacturer. Cell lines naturally expressing Notch3 or stably transfected with Notch3 expression constructs were seeded in 96-well plates. Alternatively, transiently transfected 293T or CHO cells were seeded in the 96-well plate. The cells were seeded at a density of 30,000-50,000 cells per well. After 20-24 hours, anti-Notch3 MAbs and 1×PBS reaction buffer were added to the wells and incubated for one hour at 37° C. Cy-5-conjugated anti-mouse IgG antibody was added in the wells after removal of primary antibodies.

Cell-based antibody-binding was also assessed by fluorescence-activated cell sorter (FACS) using an internally generated 293T/Notch3-stable cell line and two cancer lines, human Sup-T1 and A2780 cell lines (UK ECACC No. Cat. No. 93112519), which both naturally express Notch3 (data not shown). Cells were first incubated with anti-Notch3 MAbs in 1×PBS. After three washes, the cells were incubated with fluorescent molecule-conjugated secondary antibody. The cells were resuspended, fixed in 1×PBS with 0.1% paraformaldehyde, and analyzed by FACS (BD Sciences, Palo Alto, Calif.). The results indicated that both MAbs bind to Notch3 receptor expressed either from recombinant plasmid constructs or as native protein in cultured cells (Table 2). However, Western blot showed that when the Notch3 receptor or the Notch3-LD/Fc fusion protein are denatured in SDS-PAGE and transferred to nylon blot membrane, the anti-Notch3 MAbs no longer bind, suggesting a conformational epitope. Transiently transfected 293T cells containing a Notch3/Hygro plasmid were also stained with immunofluorescence as described above and observed by fluorescent microscopy.

TABLE 2

Binding activity of anti-Notch3 MAbs in cell-based FACS analysis shown as mean fluorescent intensity

| Monoclonal Antibody | 293T/Notch3-stable cell line | Sup-T1 |
|---|---|---|
| 256A-4 | 195 | 43 |
| 256A-8 | 189 | 45 |
| negative control* | 21 | 23 |
| positive control** | 198 | 74 |

The cell-based FMAT™ and FACS analyses confirmed that both MAbs 256A-4 and 256A-8 indeed bind to the Notch3 receptor expressed either from recombinant plasmid constructs or as native protein in cultured cells (Table 2 and Table 3).

TABLE 3

Summary of anti-Notch3 MAbs binding activity in cell-based FMAT ™

| | mAb 256A-4 | mAb 256A-8 | mAb G3 |
|---|---|---|---|
| Notch3 (full-length)/293T | + | + | − |

G3 is a negative control human IgG1 Mab. A positive binding signal was determined based on the FMAT™ signal read-out that was significantly higher than G3 and other negative hybridoma clones ($p>0.01$). The negative signal of G3 FMAT™ binding read-out was considered background. Transiently transfected 293T cells with Notch3/Hygro plasmid were also stained with immunofluorescence as described above and observed by fluorescent microscopy.

Example 4

Western Blot Analysis of Anti-Notch3 MAb Binding Activity

Western blot was performed to assess the anti-Notch3 MAbs' binding activity to Notch3 under denaturing conditions, as well as expression levels of Notch3 and other Notch-related proteins in human cell lines. Purified Notch3-LD/Fc fusion protein was combined with protein loading buffer. Protein samples were also prepared from the transiently or stably transfected cells described in Example 1, which were harvested from culture dishes, washed once with PBS, resuspended in total cellular protein extract buffer (Pierce, Rockford, Ill.), and heated at 100° C. for 10 minutes after adding equal volume of 2× protein sample loading buffer. All samples were separated by electrophoresis in a 4-15% gradient SDS-PAGE. The proteins were transferred from gel to PVDF membrane and anti-Notch3 MAbs were applied to the Western blot membrane as the primary detection antibody. An HRP-conjugated secondary antibody was used for detection and the signal generated using a chemiluminescent substrate as described above. Positive control antibodies against human Fc, V5 tag, Notch3 and Notch1 were purchased from Invitrogen, R&D Systems, Santa Cruz Biotechnologies, and Orbigen.

Western blot analysis showed that MAbs 256A-4 and 256A-8 do not bind to Notch3-LD/Fc under denaturing conditions, which is in distinct contrast to the results observed in ELISA and FACS analyses where Notch3 LIN12/heterodimerization domains are maintained in native molecular conformation. Therefore, it is concluded that MAbs 256A-4 and 256A-8 bind to multiple epitopes in Notch3-LD that have to be maintained in their native conformation. This conclusion was confirmed by the results from epitope mapping discussed in Example 8 below.

Example 5

Assessing Functionality of Anti-Notch3 MAbs by Luciferase Reporter Assay

A. Plasmid Constructs

The full length Notch3 expression construct described in Example 3 above was confirmed by sequencing, and is identical to the published sequence depicted in FIG. 1. Human Jagged1 plasmid was obtained from OriGene (Rockville, Md.), and verified by sequencing as identical to NM_000214 (NCBI/GENBANK® accession number). Because the OriGene Jagged1 plasmid did not have an antibiotic selection marker, the Not I fragment containing Jagged1 coding sequence was transferred into PCDNA™ 3.1/Hygromycin. A 3.7 Kb subclone of human Jagged2 cDNA was generated by first strand cDNA synthesis from human T-cell leukemia cell line, HH (ATCC No. CRL-2105) and PCR-amplified. The Jagged2 cDNA was subsequently subcloned. The expression of Notch3, Jagged1, and Jagged2 was verified by transient transfection and Western blot as described in Example 4.

To generate a luciferase reporter plasmid for Notch signaling, two complementary oligonucleotide primers containing tandem repeats of CBF1 binding motif were synthesized having the following sequences:

(SEQ ID NO 7)
5'GCTCGAGCTCGTGGGAAAATACCGTGGGAAAATGAACCGTGGGAAAAT

CTCGTGG (SEQ ID NO 8)
5'GCGCGAGATTTTCCCACGAGATTTTCCCACGGTTC

These two oligoprimers were annealed at 65° C. in 100 mM of NaCl with each oligo at a concentration of 4 mM. After annealing to each other, the primers were extended by PCR. The PCR product was cloned into a commercially available vector. The insert was verified by sequencing, which contains four tandem repeats of CBF1 binding motif and two flanking Xho I sites. The insert was excised using Xho I and ligated downstream of the firefly luciferase reporter coding sequence. After luciferase reporter assay and sequencing analysis, plasmid clones with eight repeats of CBF1 binding motifs were selected and designated CBF1-Luc.

B. Stable Cell Line Generation

Two stable cell lines were generated for functional assays using human embryonic kidney cell lines (HEK293). One cell line contained the Notch3-expressing plasmid and CBF1-Luc reporter plasmid integrated into the nuclear genome. This cell line was generated by cotransfecting Notch3/hygromycin and CBF1-Luc plasmids into 293T cells using LIPOFECTAMINE™ 2000 transfection system according to the manufacturer's protocol. Stable transfection cell clones were selected against 200 μg/ml hygromycin in DMEM growth medium, and screened by luciferase reporter assay and Western blot. A cell line with relatively high level of Notch3 expression (based on Western blot) and luciferase activity was selected for use in functional assay, and designated NC85.

The second stable cell line contained a Notch ligand expression construct, such as Jagged1 or Jagged2, or PCDNA™ as negative control. Stable cell lines expressing human Jagged1 or harboring PCDNA™ 3.1 were generated by transfection into 293T cells and selection against hygromycin as described above. Jagged2 was subcloned, transfected into a 293T cell line and expected to be integrated into a specific locus in the genome. Hygromycin-resistant cells were selected as above.

C. Luciferase Reporter Assay Under Coculture Conditions

Figure 7:
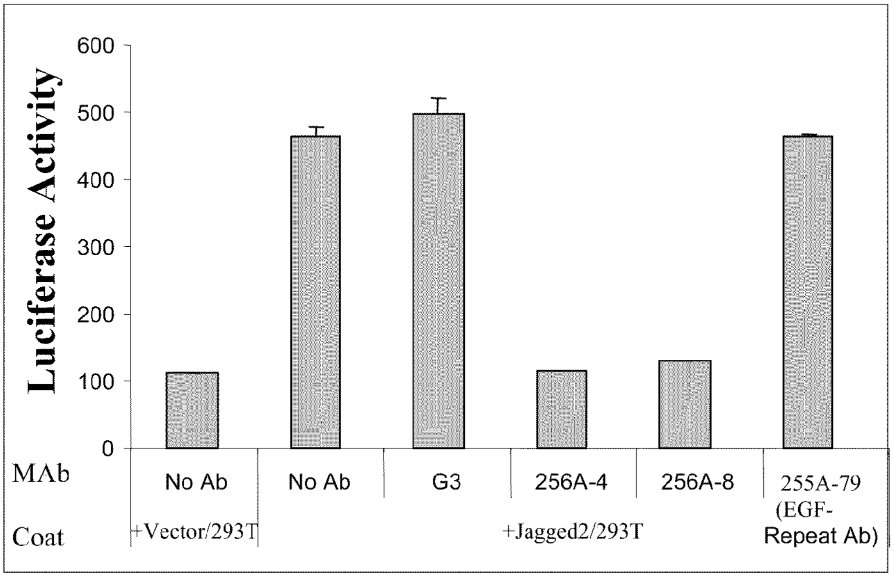
FIG. 7 depicts the luciferase reporter assay showing inhibitory effects by anti-Notch3 MAbs on the Notch3 ligand Jagged 2.

NC85 cells were mixed and cocultured with another 293T cell line stably expressing human Jagged1 (Jagged1/293T), Jagged2/293F, or PCDNA™ 3.1/293T, respectively, for 24 to 48 hours. At the end of the co-culture, the media was removed by aspiration, cells were lysed in 1× Passive Lysis Buffer (E1501, Promega, Madison, Wis.) and luciferase activities were assayed using the Luciferase Assay System following manufacturer's protocol (E1501, Promega, Madison, Wis.) in TD-20/20 luminometer (Turner Designs Instrument, Sunnyvale, Calif.). As illustrated in FIG. 6 and FIG. 7, when NC85 cells were cocultured with Jagged1/293T or with Jagged2/293F, the luciferase activity was increased 2-4 fold as compared to that of coculturing with PCDNA™ 3.1/293T cells. To assess the inhibitory effect of anti-Notch3 MAbs, the antibodies were added to the cell culture at beginning of seeding and mixing of cocultured cells. (256-A, 256A-8 and an EGF-Repeat Domain control 255A-79).

D. Luciferase Reporter Assay by Culturing Cells on Notch Ligand-Coated Plates

Figure 8:
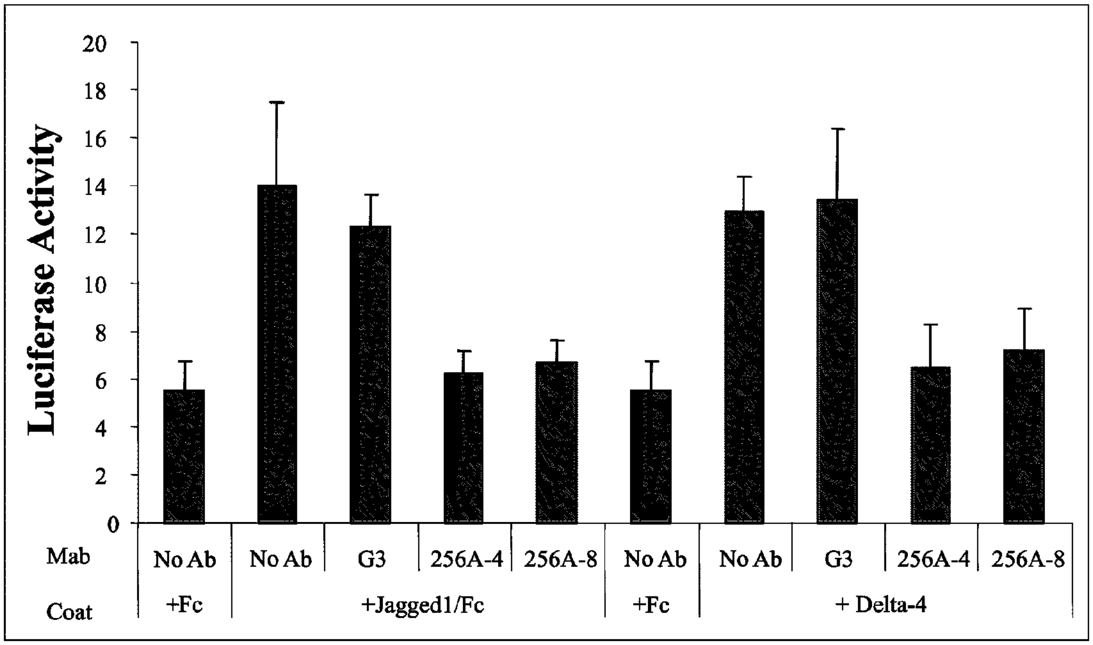
FIG. 8 depicts the luciferase reporter assay showing inhibitory effects by anti-Notch3 MAbs on the Notch3 ligand DLL4.

Regular 96-well tissue culture plates from Becton Dickinson Labware (#18779, Palo Alto, Calif.) were coated with rat Jagged1/Fc, human DLL-4 (R&D Systems, Minneapolis, Minn.) or Human Fc (Jackson ImmunoResearch, West Grove, Pa.), bovine serum albumin (Sigma, St Louis, Mo.). One hundred microliters of each protein (3 μg/ml in PBS) was distributed in a well and maintained at room temperature or 4° C. for at least 8 hours until the coating solution was removed before use. NC85 cells or cancer cells were seeded at $3\text{-}5\times10^4$ cells per well and allowed to grow for 28-48 hours. The luciferase reporter assay and antibody inhibition assay were performed as described in Section C above. The luciferase reporter assay demonstrated the two MAbs 256A-4 and 256A-8 binding to LIN12/dimerization domain almost completely blocked Jagged1 and Jagged2-induced luciferase reporter activity (FIGS. 6 and 7). In contrast, a MAb specifically binding to Notch3-EGF domain (255A-79), as a control, only inhibited Jagged1-induced luciferase reporter activity (about 60% inhibition, FIG. 6), but not Jagged2-induced luciferase reporter activity (FIG. 7). The ability of MAbs 256A-4 and 256A-8 to block DLL-4-induced luciferase reporter activity is shown in FIG. 8.

Additional functional assays demonstrated that MAbs 256A-4 and 256A-8 inhibited ligand-induced up-regulation of Notch target genes. 293T cells expressing recombinant Notch3 were cultured on Jagged-1-coated plates. In the presence of MAbs 256A-4 and 256A-8, up-regulation of HES5 and HEY2, two Notch target genes, was inhibited, as measured by quantitative RT-PCR (data not shown).

Figure 9A:
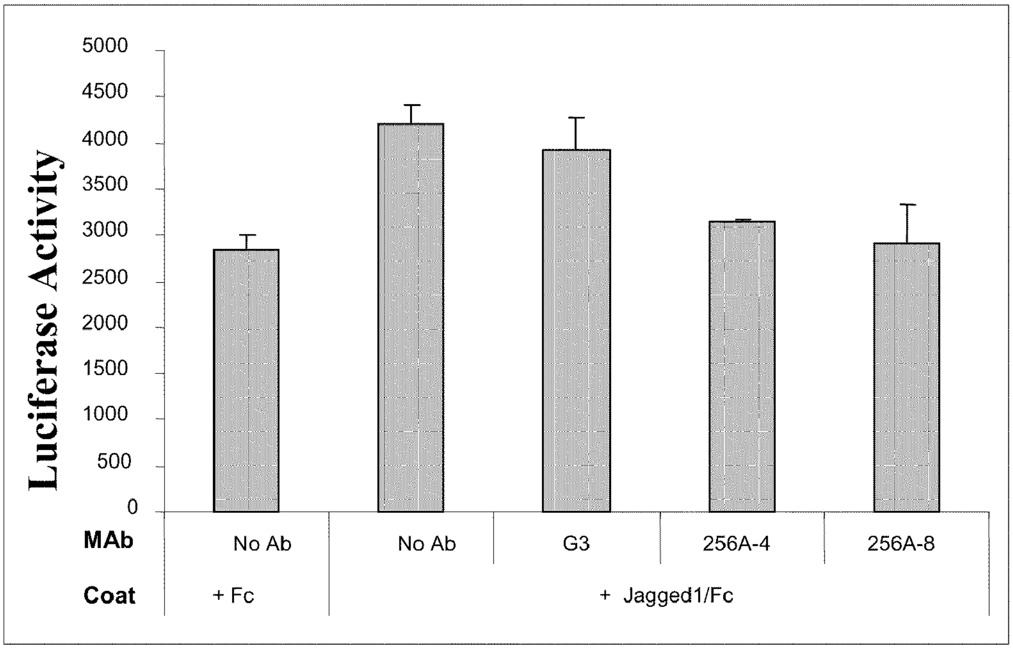
FIG. 9 depicts the luciferase reporter assay showing inhibitory effects to native Notch3 in ovarian cancer cells by anti-Notch3 MAbs. (9A) Human ovarian cancer cell line, OV/CAR3 and (9B) Human ovarian cancer cell line, A2780.
Figure 9B:
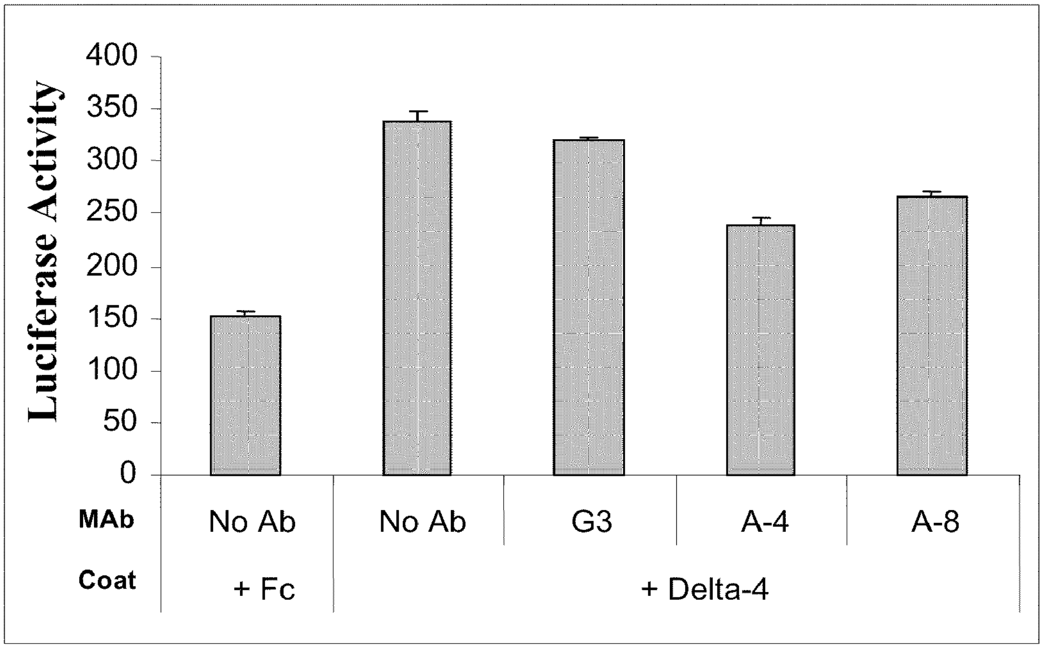

To verify whether the anti-Notch3 MAbs can bind to native Notch3 expressed in human cancer cells and block the receptor signaling, a reporter assay was performed using two ovarian cancer cell lines, OV/CAR3 and A2780. Both 256A-4 and 256A-8 significantly blocked Jagged1-induced Notch signaling mediated by native Notch3 in OV/CAR3 cells (FIG. 9*a*). Similarly, both MAbs inhibited about 50% of luciferase activity induced by D114 coated on the plate (FIG. 9*b*). The latter result is consistent with the fact that both Notch1 and Notch3 are expressed in A2780 cells. These results suggest that the anti-Notch3 MAbs can inhibit native Notch3-mediated signaling in cancer cells.

Example 6

Apoptosis Assay

Figure 10:
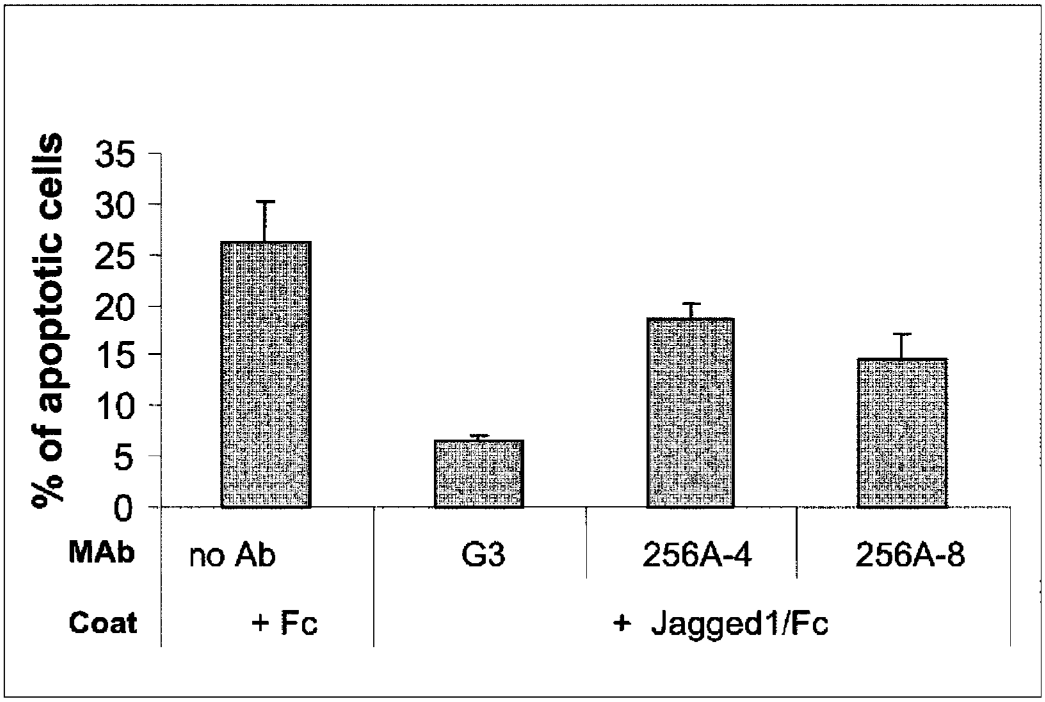
FIG. 10 depicts the apoptosis assay of Example 6 showing that cell survival effect induced by Jagged1 was inhibited by anti-Notch3 MAbs.

Annexin V is an early apoptotic marker on the cell surface, and the apoptotic cell population can be marked by fluorophore-labeled anti-Annexin V antibody and quantified by FACS analysis. NC85 cells were seeded at 5-6×$10^4$ cells per well in Fc- or Jagged1/Fc-coated 96-well plate as described above and maintained in serum-free DMEM medium for 24 hours. Apoptotic cells were stained by FITC-labeled anti-Annexin V antibody (BD Biosciences, Palo Alto, Calif.) and analyzed by FACS. Cells cultured on Jagged1/Fc-coated surface had significantly lower apoptotic cell population comparing to those cultured on Fc-coated plate (FIG. 10). To study the antibody's functional effect, anti-Notch3 MAbs were added in cell culture at the beginning of the study. As shown in FIG. 10, anti-Notch3 MAbs 256A-4 and 256A-8 blocked about 50-65% of the cell survival effect induced by Jagged1.

Example 7

Cell Migration Assays, Invasion Assays, and Morphology Assays

In vitro cell migration and invasion assays are frequently used to assess metastasis potential of cancer cells. These assays were performed to assay the inhibitory effect exerted by the anti-Notch3 MAbs on the tumorgenic 293T/Notch3-stable cell line (NC85). The invasion assay was performed using COSTAR® 48-well insert plate (Sigma-Aldrich, St. Louis, Mo.). The insert divides the well into upper and lower chambers which are separated by a porous membrane (pore diameter=8 μm) at the bottom of the insert. Notch ligands, Jagged1/Fc, DLL-4, or human Fc, were immobilized on the membrane surface as describe in above sections. NC85 cells were seeded at 100,000 cells per well and maintained in serum-free DMEM in the upper chamber and 10% FCS/DMEM in the lower chamber. After 10-24 hours, cells that remained on the top surface of the insert membrane were removed, and the cells that passed the membrane adhering on the bottom of the insert membrane were stained by 0.05% crystal velvet in PBS. The dye was extracted from the cells by 30% acetic acid and absorption readings at 590 nm were recorded. The anti-Notch3 MAbs were added to cell culture 24 hours before seeding NC85 cells in the COSTAR® assay plate and all MAbs were added to the cell culture 24 hours before seeding NC85 cells in the COSTAR® assay plate. Fresh MAbs were added to maintain the same concentration in the migration assay plate. Experimental results are shown in FIG. 11A.

The invasion assay was performed using Becton Dickinson 48-well MATRIGEL™ plate (BD Labware, Palo Alto, Calif.). The cell culture well was divided by an insert well into upper and lower chambers, which are separated by a porous membrane (pore diameter=8 μm) at the bottom of the insert well. An optimized density of MATRIGEL™ matrix was coated on the membrane top surface and fibronectin was coated on the membrane bottom surface by the manufacturer. NC85, Jagged1/293T, and pcDNA3.1/293T cells were mixed pair-wise such as indicated in FIG. 11B. A total of 6-10×$10^4$ cells were seeded in each well in the 48-well MATRIGEL™ plate and cultured in growth medium for 24 hours. The cells that remained on top of the insert membrane in the upper chamber were removed and the cells that passed the membrane adhering on the bottom of the insert membrane were stained by 0.05% crystal velvet in PBS. The dye was extracted and absorption measurements were as described in the previous section. MAbs were added at the beginning of the mixed cell culture. The results are shown in FIG. 11B.

Figure 11A:
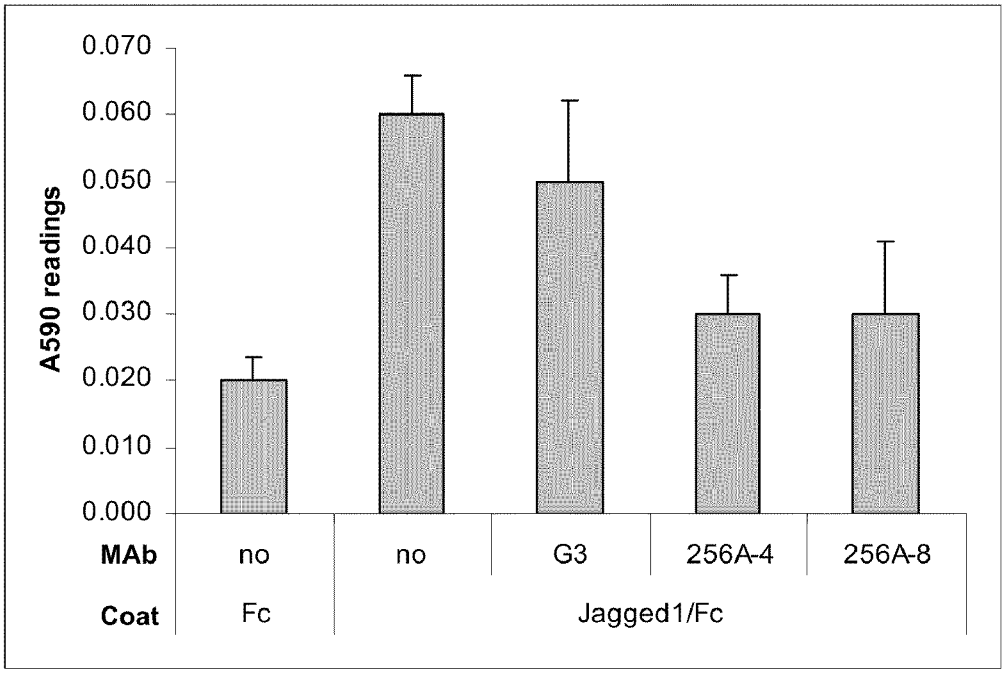
FIG. 11 depicts the inhibitory effect of anti-Notch3 MAbs on cell migration (11A) and invasion (11B) of Example 7.
Figure 11B:
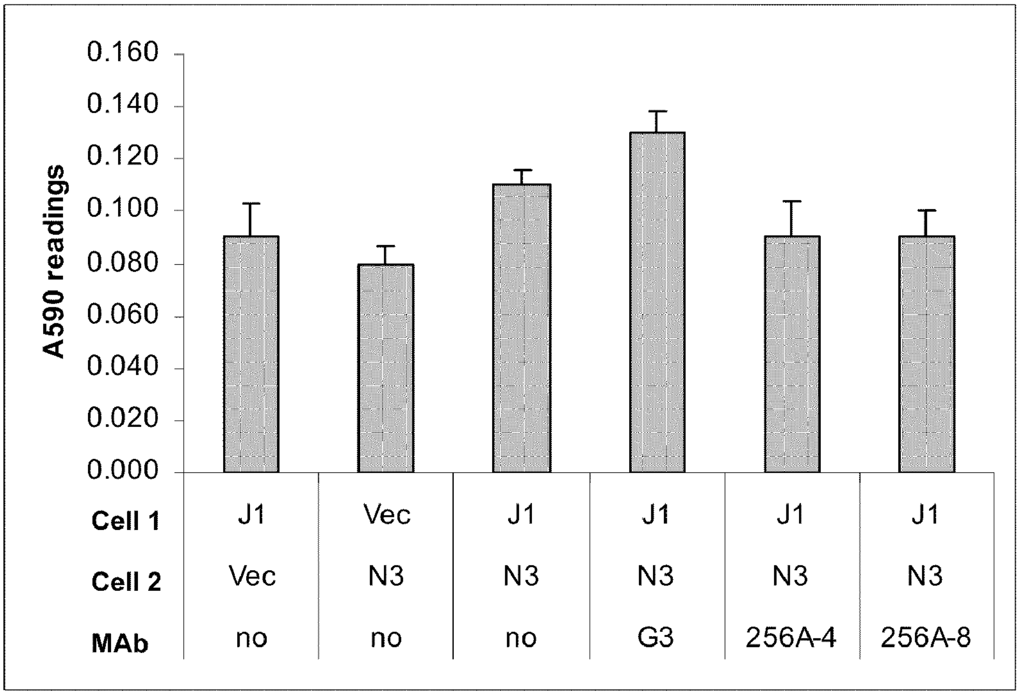

The cell migration assay results showed that when NC85 cells were cultured on Jagged1-coated membrane, the activation of Notch3 signaling significantly increased cell migration, and MAbs 256A-4 and 256A-8 clearly inhibited the migration (FIG. 11A). The invasion experiment showed a similar trend (FIG. 11B).

Additionally, the effect of MAbs 256A-4 and 256A-8 on Jagged-1-induced formation of cell "spheres" was examined. When 293T cells over-expressing Notch3 were cultured on Jagged-1-coated plates, the cells formed loosely attached "cell balls" or "spheres." In the presence of MAbs 256A-4 and 256A-8, however, formation of these cell spheres was inhibited (data not shown).

Example 8

Mapping the Binding Epitope of Anti-Notch3 MAbs

A. Domain Swap Strategy and Rationale

Figure 12:
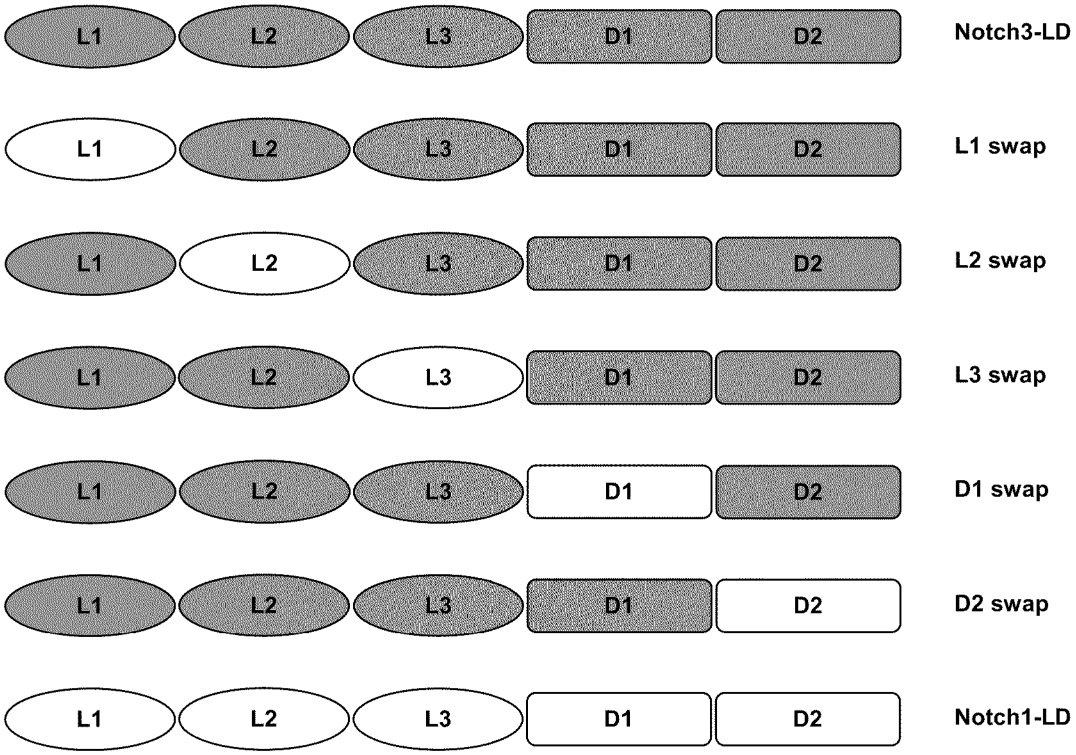
FIG. 12 depicts a schematic diagram of the Notch1-Notch3 domain-swap protein expressed as a fusion protein with human IgG/Fc linked to C-terminus.
Figure 13A:
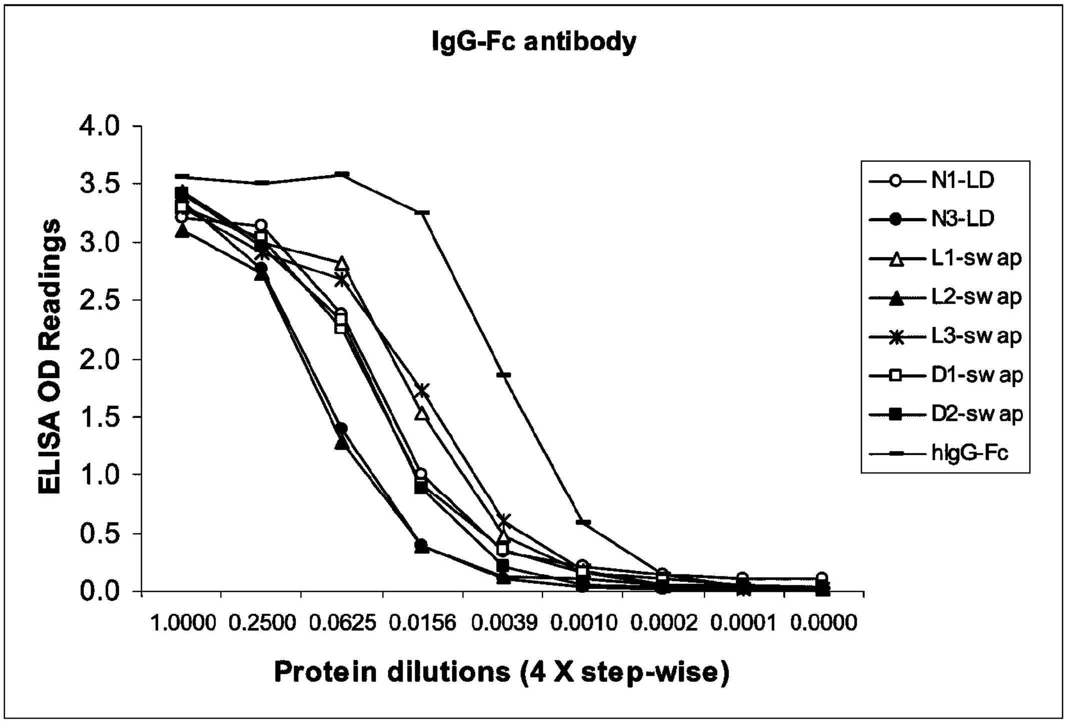
FIG. 13A depicts an ELISA using anti-human Fc control antibody as the detection antibody showing that the proteins of FIG. 12 were expressed in conditioned medium.
Figure 13B:
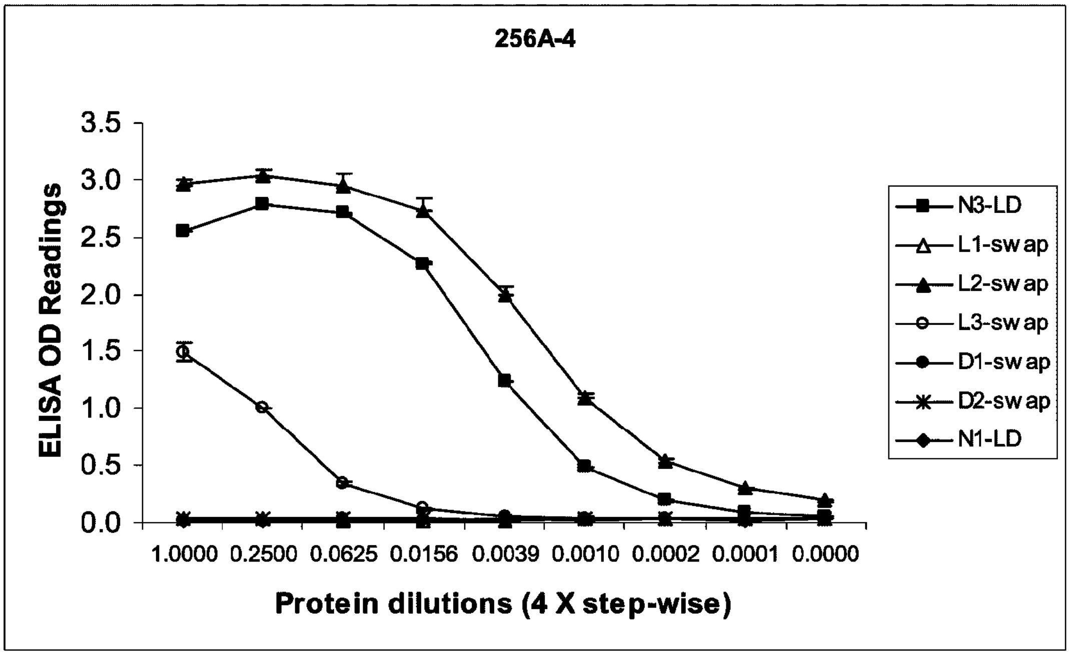
FIG. 13B depicts an ELISA using 256A-4 as the detection antibody.
Figure 13C:
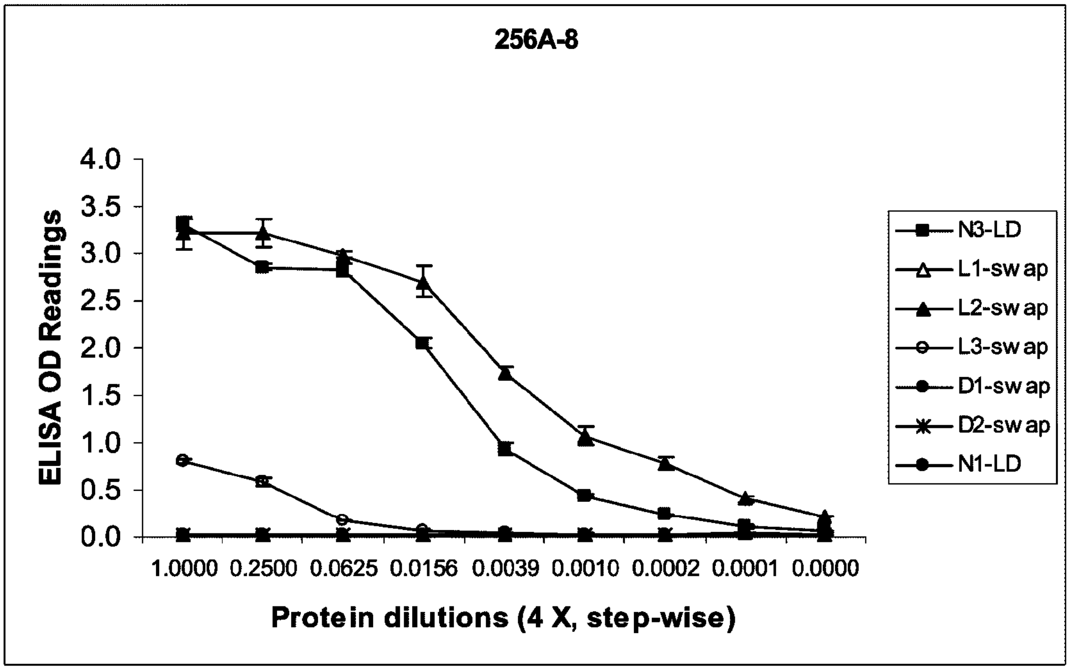
FIG. 13C depicts an ELISA using 256A-8 as the detection antibody.
Figure 13D:
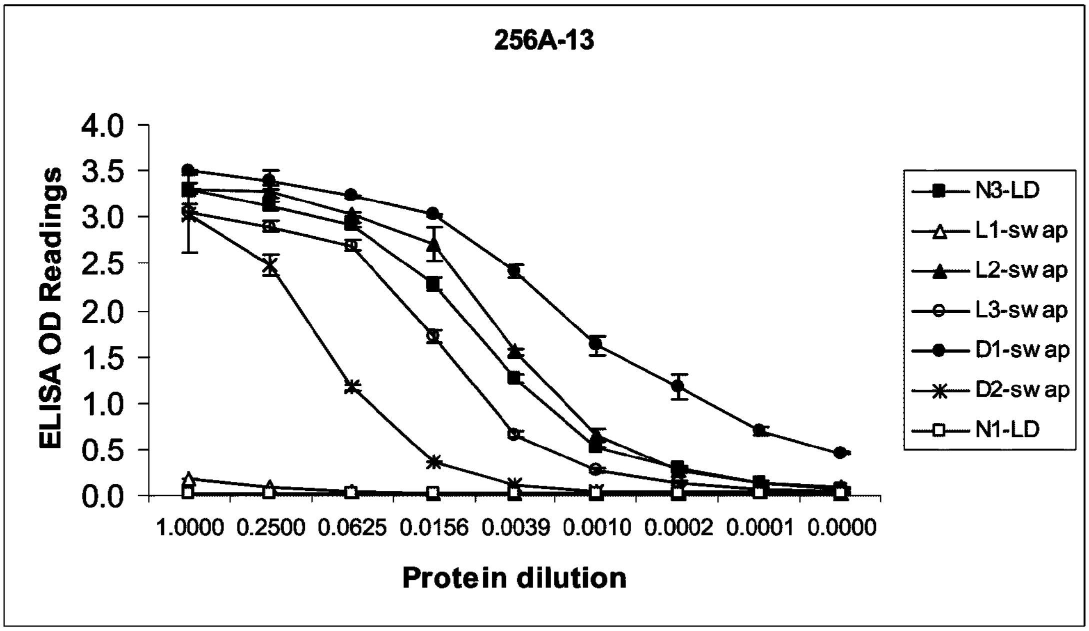
FIG. 13D depicts an ELISA using a positive control antibody 256A-13 as the detection antibody.

First, the antagonist Notch3 MAbs bind to Notch3 LIN12/dimerization domain (LD), but not to the homologous human Notch1 LIN12/dimerization domain (See FIGS. 12 and 13). Second, the anti-Notch3 MAbs do not bind to denatured Notch3 protein in Western blot as discussed in Example 4, indicating the MAbs bind to conformational epitopes. Third, Notch3 and Notch1 share approximately 55% amino acid sequence homology in the LIN12/dimerization domain, and therefore it was concluded that a domain swap between Notch3 and Notch1 within this region would not disrupt the protein conformation.

B. Generating Domain Swap Fusion Protein Constructs

Sequence analysis indicated that Notch3 has three LIN12 repeats and its dimerization domain is divided into two segments. Therefore, five domain swap protein constructs were generated with each of the three LIN12 repeats and the two dimerization segments replaced by the corresponding domains of Notch1. The domain swap constructs were generated using PCR-SOE (Ho, et al., *Gene* 77:51 (1989); Horton, et al., *BioTechniques* 8:528 (1990)) as illustrated in FIG. 12. PCR and PCR-SOE reactions were performed using PCR with 1M Betaine and 5% DMSO added to the reaction. PCR thermocycling was almost same for PCR and PCR-SOE except that the annealing step of each PCR cycle was extended one minute in PCR-SOE. The final PCR-SOE product was subcloned and verified by sequencing. The plasmid clone with the correct insert sequence was cleaved with Nhe I and Xho I to excise the insert, which was gel-purified and subcloned. The five Notch3/Notch1 domain swap constructs are illustrated in FIG. 12. To facilitate the epitope mapping, the human IgG kappa chain signaling peptide was used as leader peptide in the domain swap constructs. The amino acid sequences are shown in FIGS. 16 and 17.

Notch1-LD cDNA was PCR-amplified using PCR and methods described in the above section. The first strand cDNA template was synthesized from PA-1 cell total RNA (ATCC No. CRL-1572). The human IgG kappa chain leader peptide coding sequence was PCR-amplified, used as leader peptide to link to the 5' of Notch1-LD by PCR-SOE and subcloned in His-γ1Fc/pSec.

Based on ELISA analysis results, target domains L1, D1 and D2 were further divided into subdomains. ELISA binding analysis using the subdomain expression constructs showed that only L1 and D2 were required for the Notch3 MAb binding. The D1 domain was not required. Therefore, L1 and D2 domains were divided into clusters of amino acid mutations for further analysis of the specific binding site. Constructs containing L1 and D2 subdomain swap or clusters of amino acid mutations as shown in FIG. 16 and FIG. 17 were generated.

C. Expression of Notch3/Notch1 Domain Swap Fusion Protein

Notch3/Notch1-LD domain swap plasmids were transiently transfected in CHO cells using LIPOFECTAMINE™ 2000 transfection system. CHO cells were seeded in DMEM growth medium with 10% FCS at 0.8~$1\times10^6$ cells per well in E-well plate, maintained in $CO_2$ incubator overnight before transfection. The cells were recovered after transfection in the growth medium for about 3 hours, then switched to DMEM with 2% FCS, and cultured for three days. The conditioned media were harvested and centrifuged at 3500 rpm for 10 minutes. The supernatant containing Notch3-LD domain swap protein secreted from CHO was collected and prepared for Western blot and ELISA binding analyses. ELISA showed that all the domain-swap fusion proteins were expressed and secreted in conditioned medium (Table 4), which was further confirmed by Western blot analysis (data not shown).

The ELISA readings used anti-human Fc antibody as detection antibody showing all the proteins were expressed in conditioned medium. Human IgG/Fc was used as a control. The starting point of human IgG/Fc coated in each well is 100 ng.

TABLE 4

| | ELISA Readings | | | | | | | |
|---|---|---|---|---|---|---|---|---|
| Dilution | N1-LD | N3-LD | L1-swap | L2-swap | L3-swap | D1-swap | D2-swap | hIgG-Fc |
| | | | | Statistics: mean | | | | |
| 1 | 3.2000 | 3.3445 | 3.4380 | 3.0970 | 3.2910 | 3.2870 | 3.4110 | 3.5510 |
| 0.250000 | 3.1305 | 2.7625 | 2.9890 | 2.7390 | 2.9050 | 3.0225 | 2.9570 | 3.4995 |
| 0.062500 | 2.3785 | 1.3870 | 2.8145 | 1.2835 | 2.6855 | 2.2575 | 2.3240 | 3.5805 |
| 0.015625 | 1.0085 | 0.3960 | 1.5245 | 0.3865 | 1.7350 | 0.9110 | 0.8800 | 3.2355 |
| 0.003906 | 0.3300 | 0.1075 | 0.4755 | 0.1220 | 0.5970 | 0.3450 | 0.2130 | 1.8585 |
| 0.000977 | 0.2095 | 0.0400 | 0.1640 | 0.1105 | 0.1780 | 0.1635 | 0.0615 | 0.5865 |
| 0.000244 | 0.1340 | 0.0225 | 0.0500 | 0.0595 | 0.0575 | 0.1045 | 0.0275 | 0.1445 |
| 6.104E−05 | 0.1000 | 0.0135 | 0.0405 | 0.0505 | 0.0230 | 0.0575 | 0.0305 | 0.0315 |
| 1.526E−05 | 0.0975 | 0.0165 | 0.0205 | 0.0430 | 0.0180 | 0.0400 | 0.0155 | 0.0220 |
| 3.815E−06 | 0.0580 | 0.0140 | 0.0135 | 0.0300 | 0.0150 | 0.0425 | 0.0235 | 0.0230 |
| 9.537E−07 | 0.0540 | 0.0125 | 0.0155 | 0.0245 | 0.0215 | 0.0480 | 0.0145 | 0.0165 |
| 2.384E−07 | 0.0415 | 0.0125 | 0.0145 | 0.0305 | 0.0155 | 0.0370 | 0.0150 | 0.0190 |
| | | | | Statistics: S.D. | | | | |
| 1 | 0.0778 | 0.0290 | 0.0679 | 0.0255 | 0.0933 | 0.1018 | 0.0283 | 0.0071 |
| 0.250000 | 0.0191 | 0.0304 | 0.0354 | 0.0396 | 0.0693 | 0.1619 | 0.1202 | 0.0148 |
| 0.062500 | 0.0898 | 0.0919 | 0.0007 | 0.1096 | 0.0318 | 0.0021 | 0.0071 | 0.0290 |
| 0.015625 | 0.0474 | 0.0354 | 0.0106 | 0.0417 | 0.1075 | 0.0071 | 0.0325 | 0.1450 |
| 0.003906 | 0.0523 | 0.0177 | 0.0460 | 0.0113 | 0.0453 | 0.0339 | 0.0057 | 0.0573 |
| 0.000977 | 0.0092 | 0.0057 | 0.0042 | 0.0191 | 0.0156 | 0.0205 | 0.0007 | 0.0955 |
| 0.000244 | 0.0226 | 0.0092 | 0.0014 | 0.0106 | 0.0064 | 0.0035 | 0.0049 | 0.0276 |
| 6.104E−05 | 0.0113 | 0.0007 | 0.0064 | 0.0035 | 0.0057 | 0.0134 | 0.0064 | 0.0064 |
| 1.526E−05 | 0.0021 | 0.0035 | 0.0049 | 0.0042 | 0.0000 | 0.0028 | 0.0007 | 0.0028 |
| 3.815E−06 | 0.0113 | 0.0028 | 0.0021 | 0.0000 | 0.0042 | 0.0064 | 0.0007 | 0.0057 |
| 9.537E−07 | 0.0014 | 0.0007 | 0.0007 | 0.0007 | 0.0064 | 0.0057 | 0.0021 | 0.0078 |
| 2.384E−07 | 0.0120 | 0.0035 | 0.0049 | 0.0021 | 0.0007 | 0.0113 | 0.0014 | 0.0127 |

Abbreviations for proteins used in the ELISA binding assays of Table 4 include: N1-LD, Notch1-LD/Fc. N3-LD, Notch3-LD/Fc. L1-swap: 1st LIN12 domain swap. L2-swap: 2nd LIN12 domain swap. L3-swap: 3rd LIN12 domain swap. D1-swap: 1st dimerization domain swap. D2-swap: 2nd dimerization domain swap. hIgG-Fc, human IgG Fc.

D. Epitope Binding Analysis Using ELISA

The 96-well flat bottom IMMULON® II microtest plates (Dynatech Laboratories, Chantilly, Va.) were coated with anti-human Fc antibody (Jackson ImmunoResearch) by adding 100 μl of the antibody (0.1 μg/ml) in phosphate buffered saline (PBS) containing 1× Phenol Red and 3-4 drops pHix/liter (Pierce, Rockford, Ill.), and incubated overnight at room temperature. After the coating solution was removed by flicking of the plate, 200 μl of blocking buffer containing 2% BSA in PBST and 0.1% merthiolate was added to each well for one hour to block non-specific binding. The wells were then washed with PBST. Fifty microliters of the above conditioned medium from each transfection of Notch3/Notch1 domain swap construct were collected, mixed with 50 μl of blocking buffer, and added to the individual wells of the microtiter plates. After one hour of incubation, the Notch3/Notch1-LD domain swap protein was captured by the coated anti-Fc antibody, and the wells were washed with PBST. Anti-Notch3 MAbs and isotype-matched control MAbs were serially diluted in blocking buffer as above, and 50 μl of the diluted MAbs were added in each well to assess binding to the bound Notch3/Notch1 domain swap protein. Horseradish peroxidase (HRP)-conjugated, Fc-specific goat anti-mouse IgG was used for detection. HRP substrate solution containing 0.1% 3,3,5,5-tetramethyl benzidine and 0.0003% hydrogen peroxide was added to the wells for color development for 30 minutes. The reaction was terminated by addition of 50 ml of 2 M $H_2SO_4$/well. The OD at 450 nm was read with an ELISA reader. Subdomain swap constructs and clusters of mutations were similarly examined by ELISA analysis above.

ELISA binding experiments using MAbs 256A-4 and 256A-8 against the domain-swap proteins showed that the swap of the 1st LIN12 domain (L1) and 2nd dimerization domain (D2) completely abolished all the three MAbs binding, while the swap of 1st dimerization domain (D1) abolished binding of MAbs 256A-4 and 256A-8 (FIGS. 13 B&C). Swap of the 3rd LIN12 domain (L3) significantly weakened the binding. Nevertheless, both MAbs were still able to bind to the fusion protein. The swap of the 2nd LIN12 domain had no interference with the binding of the MAbs (FIGS. 13B and C). A positive control antibody, which was previously mapped to bind to the 1st LIN12 domain, bound to all domain swap fusion protein except L1 (FIG. 13D). In contrast, isotype control negative antibody, G3, does not bind to any of the domain swap fusion proteins in the ELISA assay (data not shown). It was concluded from the above experiments that the 1st LIN12 domain and 2nd dimerization domain were required for MAbs 256A-4 and 256A-8 binding.

To further map the epitopes in the 1st LIN12 domain (L1) to which anti-Notch3 MAbs bind, the L1 domain was further divided into three subdomains, L1-sub1, L1-sub2 and L1-sub3, and swapped with the corresponding sequences in Notch1 (FIG. 16). An ELISA binding assay showed that L1-sub1 swap has no inhibitory effects on binding activity, and L1-sub2 and L1-sub3 swap abolished binding (FIG. 16). In L1-sub2 and L1-sub3 regions, there are five clusters of amino acid residues that differ between Notch3 and Notch1. Therefore, swap fusion protein constructs were generated within these five clusters of amino acids (FIG. 16). ELISA analysis demonstrated that L1-cluster4 swap had no inhibition on all three MAbs binding. The remaining four clusters of swap partially or completely abolished the anti-Notch MAbs binding. Thus, those four clusters of amino acid residues represented four different epitopes to which the MAbs bind. L1-cluster3 (amino acids: DRE) and L1-cluster5 (amino acids: SVG) are required. L1-cluster1 (amino acids: AKR) and cluster2 (amino acids: DQR) also played a role in anti-Notch3 MAb binding, whose mutations significantly weakened the MAb binding.

To map the epitopes in the $2^{nd}$ dimerization (D2) domain of Notch3 to which anti-Notch3 MAbs bind, the D2 domain was further divided into five subdomains, D2-sub1, D2-sub2, D2-sub3, D2-sub4 and D2-sub5. The sequences in those subdomains were swapped with the corresponding sequences in Notch1 (FIG. 17). An ELISA binding assay showed that MAbs 256A-4 and 256A-8 have strong binding to D1-sub2 and D2-sub3 swap, but not to D2-sub1 and D2-sub4 swap. Both MAbs showed weak binding to D2-sub5 (FIG. 17). Therefore, the data suggested that D2-sub1 and D2-sub4 are required for the anti-Notch3 MAb binding and D2-sub5 may help the binding activity.

Both MAbs 256A-4 and 256A-8 are antagonistic antibodies binding to the conformational epitope comprising L1 and D2, while another antibody 256A-13 that binds only to L1 is agonistic (See co-pending U.S. application Ser. No. 11/874,682, filed Oct. 18, 2007). Furthermore, agonistic 256A-13 competes with antagonistic 256A-4 for an epitope within L1, and the epitope mapping studies suggest that they bind to an overlapping epitope on L1. The major difference is that the antagonistic antibodies also bind to D2, while the agonistic antibody does not. To test the hypothesis that simultaneous binding to L1 and D2 is responsible for the antagonistic activity, an antibody, 256A-2 binding to a similar epitope in D2 as 256A-4 was analyzed. MAb 256A-2 is neither antagonistic nor agonistic (data not shown). Studies showed that 256A-2 does not compete with 256A-13 and can bind to Notch3 simultaneously. Furthermore, 256A-2 and 256A-13 individually can partially compete with 256A-4, however, in combination these two antibodies completely block binding of 256A-4 to Notch3 (data not shown). Studies also showed that separate binding of two antibodies to the epitopes in L1 and D2 does not lead to the inhibition of ligand-dependent Notch3 activation, suggesting that the antagonistic antibodies form a bridge, possibly locking and stabilizing the L1 and D2 interaction, and preventing the ligand induced conformational changes. (See FIG. 18)

Example 9

Sequencing of Anti-Notch3 MAbs

Because antibody binding properties are dependent on the variable regions of both heavy chain and light chain, the variable sequences of 256A-4 and 256A-8 were subtyped and sequenced. The antibody IgG subtype was determined using an ISOSTRIP™ mouse monoclonal antibody isotyping kit (Roche Diagnostics, Indianapolis, Ind.). The results showed that both MAbs, 256A-4 and 256A-8 have an $IgG_1$ heavy chain and a kappa light chain.

The variable region sequences of heavy chain and light chain were decoded through RT-PCR and cDNA cloning. Total RNAs from hybridoma clones 256A-4 and 256A-8 were isolated using an RNeasy Mini kit following the manufacturer's protocol (QIAGEN, Valencia, Calif.). The first strand cDNA was synthesized using the RNA template and SUPERSCRIPT® III reverse transcriptase kit. The variable region of light chain and heavy chain cDNAs were PCR-amplified from the first strand cDNA using degenerative forward primers covering the 5'-end of mouse kappa chain coding region and a reverse primer matching the constant region at the juncture to the 3'-end of the variable region, or using degenerative forward primers covering the 5'-end of mouse heavy chain coding region and a constant region reverse primer in mouse heavy chain. The PCR product was cloned into a commercially available vector and sequenced by Lone Star Lab (Houston, Tex.). The nucleotide sequences were analyzed utilizing the DNASTAR® computer software program (DNASTAR, Inc., Madison, Wis.). Each anti-Notch3 MAb sequence was determined by sequences from multiple PCR clones derived from the same hybridoma clone.

MAb 256A-4 contains 123 and 116 amino acid residues, respectively, in its variable region of heavy chain and light chain (FIGS. 4A and 4B). MAb 256A-8 consists of 122 and 123 amino acid residues in heavy chain and light chain variable regions, respectively (FIGS. 5A and 5B).

Example 10

Impact of Notch3 Antagonistic Antibodies on Metalloprotease Cleavage of Notch3

Notch receptor activation involves ligand induced metalloprotease cleavage at juxtamembrane site (S2) generating an extracellular subunit. This cleavage is an essential prerequisite to S3 cleavage to release the activated Notch intracellular region. Both 256A-4 and 256A-8 were found to require the presence of at least a portion of the Notch3 L1 and D2 domains for their bindings. These two domains are not located in close proximity in the linear sequence, but rather are on two separate polypeptides, suggesting these antibodies may stabilize an inactive, autoinhibited Notch configuration. To test whether the antagonizing antibodies can inhibit sequential Notch activation events, including two proteolytic cleavages, 293T cells stably expressing a recombinant Notch3 receptor (NC85 cells) are treated with either immobilized recombinant Jagged-1 or cocultured with 293T cells expressing Jagged-1. The soluble extracellular subunits generated by proteolytic cleavage in the culture medium are detected by an ELISA assay using an antibody bound to a solid surface that recognizes the Notch3 cleavage product. Notch3 antagonistic MAbs are expected to decrease the generation of soluble Notch3 extracellular subunits in the conditioned medium, whereas non-functional Notch3 binding antibodies would not.

To directly detect the S2 cleavage fragment, an 7.5% SDS PAGE electrophoresis and Western blot with Notch3 C-terminal antibody are performed. The S2 fragment is 57 amino acids residues smaller and migrates slightly faster than the non-cleaved Notch3 small subunit (transmembrane subunit).

To examine whether Notch3 antagonistic MAbs inhibit ligand-induced metalloprotease cleavage of Notch3 at S2, 293T cells expressing recombinant Notch3 were treated with the γsecretase inhibitor compound E (1 μM) for 4 hours, which stabilizes the product of cleavage at site S2, allowing it to accumulate. In the presence of MAbs 256A-4 and 256A-8, Jagged-1-induced metalloprotease cleavage of Notch3 at S2 was inhibited (data not shown).

Example 11

Efficacy Study Using Human Cancer Models in Xenograft Mice

A. Human Cancer Cells and Tumorigenic Cells

Human cancer cell lines with Notch3 expression such as HCC2429, HCC95 may be obtained from Academic Institutes, or from the ATCC. The 293T/PCDNA™ 3.1, and 293T/Notch3 (NC85) cells are generated by transfecting 293T with related genes and selecting with hygromycin as describe in previous sections. All cells are cultured in DMEM or RPMI 1640 medium with 10% fetal bovine serum, sodium pyruvate, nonessential amino acids, L-glutamine, vitamin solution, and penicillin-streptomycin (Flow Laboratories, Rockville, Md.). Cell lines are incubated in a mixture of 5% $CO_2$ and 95% air at 37° C. in an incubator. Cultures are maintained for no longer than 3 weeks after recovery from frozen stocks. Logarithmically growing single-cell suspensions cells with ≧90% viability are used for tumor cells injection after washing with PBS.

B. Animals

Mice are obtained from, for example, the Animal Production Area of the National Cancer Institute at Frederick Cancer Research and Development Center, Frederick, Md. The animals are purpose-bred and are experimentally naïve at the outset of the study. Mice selected for use in the studies are chosen to be as uniform in age and weight as possible. They are 6-8 weeks of age and their body weights at initiation of weight range from approximately 18 to 25 grams. Records of the dates of birth for the animals used in this study are retained in the study raw data, and the weight range at the time of group assignment is specified in the report. Each animal is identified by a numbered ear tag. The animals are group housed by treatment group (4 mice/cage) in polystyrene disposable shoe-box cages containing cellulose bedding, meeting or exceeding NIH guidelines. During the course of the study, the environmental conditions in the animal room is monitored and maintained within a temperature range of 18-26° C., and the relative humidity is recorded daily. A 12-hour light/dark illumination cycle is maintained throughout the study. Animals have irradiated food. No contaminants are known to be present in the food at levels that would interfere with the results of this study. Autoclaved water is available to each animal via water bottles. No contaminants are known to be present in the water at levels that would interfere with the results of this study. Prior to assignment to the study, all study animals are acclimatized to their designated housing for at least 7 days prior to the first day of dosing.

C. Tumor Models and Efficacy Studies

Mice are anesthetized using sodium pentobarbital (50 mg/kg body weight) and placed in the right lateral decubitus position. Cancer cells, such as non-small cell lung cancer (NSCLC) cell lines, HCC2429 (Haruki, et al. *Cancer Res.* 65:3555 (2005)), HCC95 (From Dr. John Mina), and H2122 (ATCC No. CRL5985), in 50 μl Hank's containing 10% MATRIGEL™ matrix are injected into the left lobe of the lungs. After the tumor-cell injection, the mice are turned to the left lateral decubitus position and observed for 45-60 min until they recover fully. Records of tumor cell injections are maintained in the raw study data.

All animals are observed within their cages at least once daily during study and clinical findings recorded in the study raw data. Animals that show pronounced detrimental effects may be removed from the study should it be deemed necessary. Body weight is measured once each week during the treatment. Cancer tissues from each mouse, where available, are harvested and stored for potential future biological characterization.

Example 12

Assay for Notch3 Related Diseases

To identify other Notch3 related diseases, one can sequence the Notch3 gene from patient samples, perform FISH (fluorescence in situ hybridization) and CGH (comparative genomic hybridization) analysis to look for translocation and gene amplification using patient cells, or perform immunohistochemistry to check for the over-expression of Notch3 receptor using patient tissue or tumor sections. In addition, one can isolate and culture cells from a patient suspected of having a Notch3 associated disease and study the impact of an antagonistic antibody of the present invention on cell migration, invasion, survival and proliferation. Protocols for cell migration and invasion assay are described in Example 7 and the protocol for an apoptosis assay is described in Example 6. For the cell proliferation assay, cells cultured from patient samples are be seeded in 96-well plate coated with and without Notch ligands. Antagonistic antibodies are added at the beginning of the culture. Cell numbers are counted at specific time points using trypan blue staining. Notch3 FISH and CGH analysis may be performed using the published protocols of Park, et al. (Cancer Res, 66: 12 (2006)).

Those skilled in the art will recognize, or be able to ascertain using no more than routine experimentation, many equivalents to the specific embodiments of the invention described herein. Such equivalents are intended to be encompassed by the following claims.

What is claimed:

1. A monoclonal antibody that specifically binds to Notch3, wherein the antibody specifically binds to a conformational epitope of a Notch3 fragment consisting of amino acids 1378-1640 of SEQ ID NO:1, and wherein the antibody inhibits Notch3 signaling.

2. The antibody of claim 1, wherein the antibody binds to amino acid residues in the LIN12 domain (SEQ ID NO:9) and the dimerization domain (SEQ ID NO:18).

3. The antibody of claim 1, wherein the antibody comprises a variable heavy ("VH") chain region comprising CDR-H1 of SEQ ID NO:32, CDR-H2 of SEQ ID NO:33, and CDR-H3 of SEQ ID NO:34, and a variable light ("VL") chain region comprising CDR-L1 of SEQ ID NO:35, CDR-L2 of SEQ ID NO:36, and CDR-L3 of SEQ ID NO:37.

4. The antibody of claim 3, wherein the VH chain region comprises SEQ ID NO:2, and the VL chain region comprises SEQ ID NO:3.

5. A humanized form of the antibody of claim 4, wherein the humanized form specifically binds to a conformational epitope of a Notch3 fragment consisting of amino acids 1378-1640 of SEQ ID NO:1.

6. The antibody of claim 1, wherein the antibody comprises a VH chain region comprising CDR-H1 of SEQ ID NO:38; CDR-H2 of SEQ ID NO:39, and CDR-H3 of SEQ ID NO:40, and a VL chain region comprising CDR-L1 of SEQ ID NO:41; CDR-L2 of SEQ ID NO:42, and CDR-L3 of SEQ ID NO:43.

7. The antibody of claim 6, wherein the VH chain region comprises SEQ ID NO:4, and the VL chain region comprises SEQ ID NO:5.

8. A humanized form of the antibody of claim 7, wherein the humanized form specifically binds to a conformational epitope of a Notch3 fragment consisting of amino acids 1378-1640 of SEQ ID NO:1.

9. The antibody of claim 1, which is an antigen-binding antibody fragment.

10. The antibody of claim 1, which is a human, humanized, or chimeric antibody.

11. The antibody of claim 1, further comprising a label.

* * * * *